United States Patent [19]
Ellis et al.

[11] Patent Number: 5,686,241
[45] Date of Patent: *Nov. 11, 1997

[54] PROBES AND ASSAYS FOR CALCIUM CHANNEL $\alpha_2$ SUBUNIT-ENCODING NUCLEIC ACIDS

[75] Inventors: Steven Bradley Ellis, San Diego; Mark E. Williams, Carlsbad; Michael Miller Harpold, San Diego, all of Calif.; Arnold Schwartz, Cincinnati, Ohio; Robert Brenner, Austin, Tex.

[73] Assignee: Sibia Neurosciences, Inc., La Jolla, Calif.

[*] Notice: The term of this patent shall not extend beyond the expiration date of Pat. No. 5,407,820.

[21] Appl. No.: 314,083

[22] Filed: Sep. 28, 1994

Related U.S. Application Data

[62] Division of Ser. No. 914,231, Jul. 13, 1992, Pat. No. 5,407,820, which is a continuation of Ser. No. 603,751, filed as PCT/US89/01408, Apr. 4, 1989, abandoned, which is a continuation-in-part of Ser. No. 176,899, Apr. 4, 1988, abandoned.

[51] Int. Cl.[6] ............................. C12N 15/12; C12Q 1/68
[52] U.S. Cl. ...................... 435/56; 536/24.31; 536/23.5; 536/24.33; 935/78
[58] Field of Search .................... 435/69.1, 6; 536/24.31, 536/24.33, 23.5

[56] References Cited

U.S. PATENT DOCUMENTS

| | | | |
|---|---|---|---|
| 4,788,135 | 11/1988 | Davis et al. | 435/6 |
| 4,906,564 | 3/1990 | Lyon et al. | 435/7.22 |
| 4,912,202 | 3/1990 | Campbell et al. | 530/388.22 |
| 4,950,739 | 8/1990 | Cherksey et al. | 530/350 |
| 4,954,436 | 9/1990 | Froehner et al. | 424/1.49 |
| 5,051,403 | 9/1991 | Miljanich et al. | 514/12 |
| 5,189,020 | 2/1993 | Miljanich et al. | 514/12 |
| 5,256,536 | 10/1993 | Miyada et al. | 435/6 |
| 5,264,371 | 11/1993 | Miljanich et al. | 436/503 |
| 5,424,218 | 6/1995 | Miljanich et al. | 436/503 |

FOREIGN PATENT DOCUMENTS

| | | |
|---|---|---|
| 2085502 | 2/1993 | Canada . |
| 0507170 | 3/1992 | European Pat. Off. . |
| 9113077 | 9/1991 | WIPO . |
| 9202639 | 2/1992 | WIPO . |
| 9308469 | 4/1993 | WIPO . |
| 9314098 | 7/1993 | WIPO . |
| 9402511 | 2/1994 | WIPO . |
| 9504144 | 2/1995 | WIPO . |

OTHER PUBLICATIONS

Mes–Masson, A.–M., et al. (1986) *Proc. Natl. Acad. Sci USA* 83: 9768–72.

Emori, Y., et al. (1986) *J. Biol. Chem.* 261: 9472–76.

Hackett, R. W., et al. (1981) *Proc. Natl. Acad. Sci. USA* 78: 6116–200.

Borsotto et al. (1985) "The 1,4–dihydropyridine receptor associated with the sekeletal muscle voltage–dependent $Ca^{2+}$ channel," *J.Biol.Chem.*, 260(26): 14255–14263.

Claudio et al. (1987) "Genetic reconstitution of functional acetylcholine receptor channels in mouse fibroblasts," *Science*, 238: 1688–1694.

Claudio et al. (1987) "Stable expression of transfected *Torpedo acetylcholine* receptor $\alpha$ subunits in mouse fibroblast L cells," *Proc.Natl.Acad.Sci.*, 84: 5967–5971.

Cooper et al. (1987) "Purification and characterization of the dihydropyridine–sensitive voltage–dependent calcium channel from cardiac tissue," *J.Biol.Chem.*, 262(2): 509–512.

Curtis et al. (1984) "Purification of the calcium antagonist receptor of the voltage–sensitive calcium channel from skeletal muscle transverse tubules," *Biochemistry*, 23(10): 2113–2118.

Dascal et al. (1986) "Expression of modulation of voltage–gated calcium channels after RNA injection in *Xenopus oocytes,*" *Science*, 231: 1147–1150.

Leung, et al. "Structural characterization of the 1,4–dihydropyridine receptor of the voltage–dependent $Ca^{2+}$ channel from rabbit skeletal muscle," *J.Biol.Chem.*, 262(17): 7943–7946 (1987).

Leung et al. (1988) "Monoclonal antibody characterization of the 1,4–dihydropyridine receptor of rabbit skeletal muscle," *Ann.N.Y.Acad.Sci.*, 522: 43–46.

Nakayama et al. (1987) "Purification of a putative $Ca^{2+}$ channel protein from rabbit skeletal muscle," *J.Biol.Chem.*, 262: 6572–6576.

Schmid et al. (1986), "Immunochemical analysis of subunit structure of 1,4–dihydropyridine receptors asociated with voltage–dependent $Ca^{2+}$ channels in skeletal, cardiac, and smooth muscles," *Biochemistry*, 25: 3492–3495.

Seager, et al., *Ann. N.Y. Acad. Sci.* 522:43–46 (1988).

Takahashi et al. (1987) "Dihydropyridine–sensitive calcium channels in cardiac and skeletal muscle membranes: studies with antibodies against the $\alpha$–subunits," *Biochemistry*, 26(17): 1518–1526.

Vaghy et al. (1988)"Mechanism of action of calcium channel modulator drugs," *Ann.N.Y.Acad.Sci.*, 522: 176–186.

Williams (1992) "Structure and functional expression of $\alpha_1$, $\alpha_2$ and $\beta$ subunits of a novel human neuronal calcium channel subtype," *Neuron*, 8:71–84.

Wood (1987) Wood, "Gene cloning based on long oligonucleotide probes," *Methods in Enzymology*, 152: 443–447.

Leung, et al., "Biochemical and ultrastructural characterization of the 1,4–dihydropyridine receptor from rabbit skeletal muscle," *J. Biol. Chem.* 263(2):994–1101 (1988).

Imagawa, et al., "Phosphorylation of the 1,4–dihydropyridine receptor of the voltage–dependent $Ca^{2+}$ channel by an intrinsic protein kinase in isolated triads from rabbit skeletal muscle," *J. Biol. Science* 262(17):8333–8339 (1987).

(List continued on next page.)

*Primary Examiner*—David L. Fitzgerald
*Attorney, Agent, or Firm*—Stephanie L. Seidman; Brown, Martin, Haller & McClain

[57] ABSTRACT

Calcium channel (alpha)$_1$-subunit and (alpha)$_2$-subunit-encoding DNA, and related compositions and methods, are provided.

18 Claims, 20 Drawing Sheets

OTHER PUBLICATIONS

Miller, "Multiple calcium channels and neuronal function," *Science* 234:46–52 (1987)Miller (1987) Multiple calcium channels and neuronal function, *Science*, 235: 46–52.

Kozak, "An analysis of 5'–noncoding sequences from 699 vertebrate messenger RNAs," *Nucleic Acids Research* 15(20):8125–8148 (1987).

von Heijne, "Signal sequences: the limits of variation," *J. Mol. Biol.* 184:99–105 (1985).

Hubbard, et al., "Synthesis and processing of asparagine–linked oligosaccharides[1,2]," *Ann. Rev. Biochem.* 50:555–583 (1981).

Faramisco, et al., "Optimal spatial requirements for the location of basic residues in peptide substrates for the cyclic AMP–dependent protein kinase," *J. Biol. Chem.* 225(9):4240–4245 (1980).

Takahashi & Catterall, "Identification of an $\alpha$ subunit of dihydropyridine–sensitive brain calcium channels," *Science* 236:88–91 (1987).

Hofmann, et al., "Regulation of the L–type calcium channels," *TIPS* 8:393–398 (1987).

Curtis, et al., "Reconstitution of the voltage–sensitive calcium channel purified from skeletal muscle transverse tubules," *Biochemistry* 25:3077–3083 (1986).

Smith, et al., "Calcium channel activity in a purified dihydropyridine–receptor preparation of skeletal muscle," *Biochemistry* 26:7182–7188 (1987).

Ellis, et al, "Sequence and expresion of mRNAs encoding the $\alpha_1$ and $\alpha_2$ subunits of DHP–sensitive calcium channel," *Science* 241:1661–1664 (1988).

Vaghy, et al., "Identification of a Novel 1,4–Dihydropyridine– and Phenylalkylamine–binding Polypeptide in Calcium Channel Preparations," *J. Biol. Chem.* 262:14337–14342 (1987).

Meshi, et al., "Nucleotide sequence of the 30K protein cistron of cowpea strain of tobacco mosaic virus," *Nucleic Acids Research* 10:6111–6117 (1982).

Nikaido, et al., "Molecular cloning of cDNA encoding human interleukin–2 receptor," *Nature* 311:631–636 (1984).

Noda, et al., "Existence of distinct sodium channel messenger RNAs in rat brain," *Nature* 320:188–192 (1986).

Noda, et al., "Expression of functional sodium channels from cloned cDNA," *Nature* 322:826–828 (1986).

Mierendorf, et al., "Gene Isolation by Screening λgt11 Libraries with Antibodies," *Methods in Enzymology* 152:458–469 (1986).

Gustin, et al., "Ion Channels in Yeast," *Science* 233:1195–1197 (1986).

Striessnig, et al., "Photoaffinity labelling of the phenylalkylamine receptor of the skeletal muscle transverse–tubule calcium channel," *FEBS Letters* 212:247–253 (1987).

Curran and Morgan, "Barium Modulates c–fos Expression and Post–Translational Modification," *Proc. Natl. Acad. Sci. USA* 83:8521–8524 (1986).

Fisch, et al., "c–fos Sequences Necessary for Basal Expression and Induction by Epidermal Growth Factor, 12–O–Tetradecanoyl Phorbol–13–Acetate, and the Calcium Ionophore," *Mol. Cell. Biol.* 7:3490–3502 (1987).

Barhanin, et al., "The Calcium Channel Antagonists Receptor from Rabbit Skeletal Muscle: Reconsititution after Purification and Subunit Characterization," *Eur. J. Biochem.* 164:525–531 (1987).

Sieber, et al., "The 165–KDa Peptide of the Purified Skeletal Muscle Dihydropyridine REceptor Contains the Known Regulatory Sites of the Calcium Channel," *Eur. J. Biochem.* 167:117–122 (1987).

Lang, et al., "The Effect of Myasthenic Syndrome Antibody on Presynaptic Channels in the Mouse," *J. Physiol.* 390:257–270 (1987).

Catterall, et al., "Molecular Properties of Dihydropyridine–sensitive Calcium Channels in Skeletal Muscle," *J. Biol. Chem.* 263:3535–3538 (1988).

Takahashi and Catterall, "Dihydropyridine–sensitive Calcium Channels in Cardiac and Skeletal Muscle Membranes: Studies with Antibodies against the Alpha Subunits," *Biochemistry* 26:5518–5526 (1987).

Morton and Froehner, "Monoclonal Antibody Identifies a 200–kDA Subunit of the Dihydropyridine–sensitive Calcium Channel," *J. Biol. Chem.* 262:11904–11907 (1987).

Sharp, et al., "Identification and Characterization of the Dihydropyridine–binding Subunit of the Skeletal Muscle Dihydropyridine Receptor," *J. Biol. Chem.* 62:12309–12315 (1987).

Takahashi, et al., "Subunit Structure of Dihydropyridine–sensitive Calcium Channels from Skeletal Muscle," *Proc. Natl. Acad. Sci. USA* 84:5478–5482 (1987).

Tanabe, et al., "Primary Structure of the Receptor for Calcium Channel Blockers from Skeletal Muscle," *Nature* 328:313–318 (1987).

Nakayama, et al., "Purification of a Putative $Ca^{+2}$ Channel Protein from Rabbit Skeletal Muscle," *J. Biol. Chem.* 262:6572–6576 (1987).

Williams et al., "Structure and Functioal Expression of an ω–Conotoxin–Sensitive Human N–Type Calcium Channel", *Science* 257:389–395 (1992).

Williams, et al., "Structure and functional charcterization of neuronal $\alpha_{1E}$ calcium channel subtypes," *J. Biol. Chem.* 269(35):22347–22357 (1994).

Brust, et al., "Human Neuronal Voltage–Dependent Calcium Channels: Studies on Subunit Structure and Role in Channel Assembly", *Neuropharmacology* 32(11):1089–1102 (1993).

FIGURE 1a

```
                                                    GCGGGGAA CACTGGGGAC-61
GCAGGGAAGA GAGGGCCGCG GGGTGGGGGA GCAGCAGGAA GCGCCGTGGC CAGGGAAGCC-1
```

| ATG | GAG | CCA | TCC | TCA | CCC | CAG | GAT | GAG | GGC | CTG | AGG | AAG | AAA | CAG | CCC | 48 |
|---|---|---|---|---|---|---|---|---|---|---|---|---|---|---|---|---|
| MET | GLU | PRO | SER | SER | PRO | GLN | ASP | GLU | GLY | LEU | ARG | LYS | LYS | GLN | PRO | |
| | | | | 5 | | | | 10 | | | | | | 15 | | |

| AAG | AAG | CCC | CTG | CCC | GAG | GTC | CTG | CCC | AGG | CCG | CCG | CGG | GCT | CTG | TTC | 96 |
|---|---|---|---|---|---|---|---|---|---|---|---|---|---|---|---|---|
| LYS | LYS | PRO | LEU | PRO | GLU | VAL | LEU | PRO | ARG | PRO | PRO | ARG | ALA | LEU | PHE | |
| | | | 20 | | | | | 25 | | | | | 30 | | | |

| TGC | CTG | ACC | CTG | CAG | AAC | CCG | CTG | AGG | AAG | GCG | TGC | ATC | AGC | ATC | GTG | 144 |
|---|---|---|---|---|---|---|---|---|---|---|---|---|---|---|---|---|
| CYS | LEU | THR | LEU | GLN | ASN | PRO | LEU | ARG | LYS | ALA | CYS | ILE | SER | ILE | VAL | |
| 35 | | | | 40 | | | | | 45 | | | | | | | |

| GAA | TGG | AAA | CCC | TTC | GAG | ACC | ATC | ATC | CTG | CTC | ACC | ATC | TTT | GCC | AAC | 192 |
|---|---|---|---|---|---|---|---|---|---|---|---|---|---|---|---|---|
| GLU | TRP | LYS | PRO | PHE | GLU | THR | ILE | ILE | LEU | LEU | THR | ILE | PHE | ALA | ASN | |
| | 50 | | | | 55 | | | | | 60 | | | | | | |

| TGT | GTG | GCC | CTG | GCC | GTG | TAC | CTG | CCC | ATG | CCC | GAG | GAT | GAC | AAC | AAC | 240 |
|---|---|---|---|---|---|---|---|---|---|---|---|---|---|---|---|---|
| CYS | VAL | ALA | LEU | ALA | VAL | TYR | LEU | PRO | MET | PRO | GLU | ASP | ASP | ASN | ASN | |
| 65 | | | | 70 | | | | | 75 | | | | * | 80 | | |

| TCC | CTG | AAC | CTG | GGC | CTG | GAG | AAG | CTG | GAG | TAC | TTC | TTC | CTC | ACC | GTC | 288 |
|---|---|---|---|---|---|---|---|---|---|---|---|---|---|---|---|---|
| SER | LEU | ASN | LEU | GLY | LEU | GLU | LYS | LEU | GLU | TYR | PHE | PHE | LEU | THR | VAL | |
| | | | | 85 | | | | | 90 | | | | | 95 | | |

| TTC | TCC | ATC | GAA | GCC | GCC | ATG | AAG | ATC | ATC | GCC | TAC | GGC | TTC | CTG | TTC | 336 |
|---|---|---|---|---|---|---|---|---|---|---|---|---|---|---|---|---|
| PHE | SER | ILE | GLU | ALA | ALA | MET | LYS | ILE | ILE | ALA | TYR | GLY | PHE | LEU | PHE | |
| | | | 100 | | | | | 105 | | | | | 110 | | | |

| CAC | CAG | GAC | GCC | TAC | CTG | CGC | AGC | GGC | TGG | AAC | GTG | CTG | GAC | TTC | ATC | 384 |
|---|---|---|---|---|---|---|---|---|---|---|---|---|---|---|---|---|
| HIS | GLN | ASP | ALA | TYR | LEU | ARG | SER | GLY | TRP | ASN | VAL | LEU | ASP | PHE | ILE | |
| | | | 115 | | | | | 120 | | | | | 125 | | | |

| ATC | GTC | TTC | CTG | GGG | GTC | TTC | ACG | GCG | ATT | CTG | GAA | CAG | GTC | AAC | GTC | 432 |
|---|---|---|---|---|---|---|---|---|---|---|---|---|---|---|---|---|
| ILE | VAL | PHE | LEU | GLY | VAL | PHE | THR | ALA | ILE | LEU | GLU | GLN | VAL | ASN | VAL | |
| | | 130 | | | | | 135 | | | | | 140 | | | | |

| ATC | CAG | AGC | AAC | ACG | GCC | CCG | ATG | AGC | AGC | AAA | GGA | GCC | GGC | CTG | GAC | 480 |
|---|---|---|---|---|---|---|---|---|---|---|---|---|---|---|---|---|
| ILE | GLN | SER | ASN | THR | ALA | PRO | MET | SER | SER | LYS | GLY | ALA | GLY | LEU | ASP | |
| 145 | | | | 150 | | | | | 155 | | | | | | 160 | |

| GTC | AAG | GCC | CTG | AGG | GCC | TTC | CGT | GTG | CTC | AGA | CCC | CTC | CGG | CTG | GTG | 528 |
|---|---|---|---|---|---|---|---|---|---|---|---|---|---|---|---|---|
| VAL | LYS | ALA | LEU | ARG | ALA | PHE | ARG | VAL | LEU | ARG | PRO | LEU | ARG | LEU | VAL | |
| | | | 165 | | | | | 170 | | | | | 175 | | | |

FIGURE 1b

| TCG | GGG | GTG | CCT | AGT | TTG | CAG | GTG | GTC | CTC | AAC | TCC | ATC | TTC | AAG | GCC | 576 |
| SER | GLY | VAL | PRO | SER | LEU | GLN | VAL | VAL | LEU | ASN | SER | ILE | PHE | LYS | ALA | |
| | | | 180 | | | | 185 | | | | | | 190 | | | |

| ATG | CTC | CCC | CTG | TTC | CAC | ATC | GCC | CTG | CTC | GTC | CTC | TTC | ATG | GTC | ATC | 624 |
| MET | LEU | PRO | LEU | PHE | HIS | ILE | ALA | LEU | LEU | VAL | LEU | PHE | MET | VAL | ILE | |
| | | 195 | | | | | 200 | | | | | 205 | | | | |

| ATC | TAC | GCC | ATC | ATC | GGG | CTG | GAG | CTC | TTC | AAG | GGC | AAG | ATG | CAC | AAG | 672 |
| ILE | TYR | ALA | ILE | ILE | GLY | LEU | GLU | LEU | PHE | LYS | GLY | LYS | MET | HIS | LYS | |
| | | 210 | | | | 215 | | | | | 220 | | | | | |

| ACC | TGC | TAC | TAC | ATC | GGG | ACA | GAC | ATC | GTG | GCC | ACA | GTG | GAG | AAT | GAG | 720 |
| THR | CYS | TYR | TYR | ILE | GLY | THR | ASP | ILE | VAL | ALA | THR | VAL | GLU | ASN | GLU | |
| 225 | | | | | 230 | | | | | 235 | | | | | 240 | |

| AAG | CCC | TCG | CCC | TGC | GCT | AGG | ACG | GGC | TCG | GGG | CGC | CCC | TGC | ACC | ATC | 768 |
| LYS | PRO | SER | PRO | CYS | ALA | ARG | THR | GLY | SER | GLY | ARG | PRO | CYS | THR | ILE | |
| | | | | 245 | | | | | 250 | | | | | 255 | | |

| AAC | GGC | AGC | GAG | TGC | CGG | GGC | GGC | TGG | CCG | GGG | CCC | AAC | CAC | GGC | ATC | 816 |
| ASN | GLY | SER | GLU | CYS | ARG | GLY | GLY | TRP | PRO | GLY | PRO | ASN | HIS | GLY | ILE | |
| * | | | 260 | | | | | 265 | | | | | 270 | | | |

| ACG | CAC | TTC | GAC | AAC | TTC | GGC | TTC | TCC | ATG | CTC | ACC | GTG | TAC | CAG | TGC | 864 |
| THR | HIS | PHE | ASP | ASN | PHE | GLY | PHE | SER | MET | LEU | THR | VAL | TYR | GLN | CYS | |
| | | 275 | | | | | 280 | | | | | 285 | | | | |

| ATC | ACC | ATG | GAG | GGC | TGG | ACA | GAT | GTC | CTC | TAC | TGG | GTC | AAC | GAT | GCC | 912 |
| ILE | THR | MET | GLU | GLY | TRP | THR | ASP | VAL | LEU | TYR | TRP | VAL | ASN | ASP | ALA | |
| | | 290 | | | | 295 | | | | | 300 | | | | | |

| ATC | GGG | AAC | GAG | TGG | CCC | TGG | ATC | TAC | TTT | GTC | ACT | CTC | ATC | CTG | CTG | 960 |
| ILE | GLY | ASN | GLU | TRP | PRO | TRP | ILE | TYR | PHE | VAL | THR | LEU | ILE | LEU | LEU | |
| 305 | | | | | 310 | | | | | 315 | | | | | 320 | |

| GGG | TCC | TTC | TTC | ATC | CTC | AAC | CTG | GTG | CTG | GGC | GTC | CTG | AGT | GGG | GAA | 1008 |
| GLY | SER | PHE | PHE | ILE | LEU | ASN | LEU | VAL | LEU | GLY | VAL | LEU | SER | GLY | GLU | |
| | | | | 325 | | | | | 330 | | | | | 335 | | |

| TTC | ACC | AAG | GAG | CGG | GAG | AAG | GCC | AAG | TCC | AGG | GGA | ACC | TTC | CAG | AAG | 1056 |
| PHE | THR | LYS | GLU | ARG | GLU | LYS | ALA | LYS | SER | ARG | GLY | THR | PHE | GLN | LYS | |
| | | | 340 | | | | | 345 | | | | | 350 | | | |

| CTG | CGG | GAG | AAG | CAG | CAG | CTG | GAG | GAG | GAC | CTT | CGG | GGC | TAC | ATG | AGC | 1104 |
| LEU | ARG | GLU | LYS | GLN | GLN | LEU | GLU | GLU | ASP | LEU | ARG | GLY | TYR | MET | SER | |
| | | | 355 | | | | | 360 | | | | | 365 | | | |

FIGURE 1c

```
TGG ATC ACG CAG GGC GAG GTC ATG GAC GTG GAG GAC CTG AGA GAA GGA 1152
TRP ILE THR GLN GLY GLU VAL MET ASP VAL GLU ASP LEU ARG GLU GLY
    370                 375                 380

AAG CTG TCC TTG GAA GAG GGA GGC TCC GAC ACG GAA AGC CTG TAC GAA 1200
LYS LEU SER LEU GLU GLU GLY GLY SER ASP THR GLU SER LEU TYR GLU
385                 390                 395                 400

ATC GAG GGC TTG AAC AAA ATC ATC CAG TTC ATC CGA CAC TGG AGG CAG 1248
ILE GLU GLY LEU ASN LYS ILE ILE GLN PHE ILE ARG HIS TRP ARG GLN
                405                 410                 415

TGG AAC CGT GTC TTT CGC TGG AAG TGC CAT GAC CTG GTG AAG TCG AGA 1296
TRP ASN ARG VAL PHE ARG TRP LYS CYS HIS ASP LEU VAL LYS SER ARG
            420                 425                 430

GTC TTC TAC TGG CTG GTC ATC CTG ATC GTG GCC CTC AAC ACC CTG TCC 1344
VAL PHE TYR TRP LEU VAL ILE LEU ILE VAL ALA LEU ASN THR LEU SER
        435                 440                 445

ATC GCC TCG GAG CAC CAC AAC CAG CCG CTC TGG CTG ACC CAC TTG CAA 1392
ILE ALA SER GLU HIS HIS ASN GLN PRO LEU TRP LEU THR HIS LEU GLN
        450                 455                 460

GAC ATC GCC AAT CGA GTG CTG CTG TCA CTC TTC ACC ATC GAG ATG CTG 1440
ASP ILE ALA ASN ARG VAL LEU LEU SER LEU PHE THR ILE GLU MET LEU
465         470                 475                 480

CTG AAG ATG TAC GGG CTG GGC CTG CGC CAG TAC TTC ATG TCC ATC TTC 1488
LEU LYS MET TYR GLY LEU GLY LEU ARG GLN TYR PHE MET SER ILE PHE
                485                 490                 495

AAC CGC TTC GAC TGC TTC GTG GTG TGC AGC GGC ATC CTG GAG CTG CTG 1536
ASN ARG PHE ASP CYS PHE VAL VAL CYS SER GLY ILE LEU GLU LEU LEU
            500                 505                 510

CTG GTG GAG TCG GGC GCC ATG ACG CCG CTG GGC ATC TCC GTG TTG CGC 1584
LEU VAL GLU SER GLY ALA MET THR PRO LEU GLY ILE SER VAL LEU ARG
            515                 520                 525

TGC ATC CGC CTC CTG AGG CTC TTC AAG ATC ACC AAG TAC TGG ACG TCG 1632
CYS ILE ARG LEU LEU ARG LEU PHE LYS ILE THR LYS TYR TRP THR SER
        530                 535                 540
```

FIGURE 1d

```
CTC AGC AAC CTG GTG GCC TCC CTG CTC AAC TCC ATC CGC TCC ATC GCC  1680
LEU SER ASN LEU VAL ALA SER LEU LEU ASN SER ILE ARG SER ILE ALA
545                 550                 555                 560

TCG CTG CTG CTG CTG CTC TTC CTC TTC ATC ATC ATC TTC GCC CTG CTG  1728
SER LEU LEU LEU LEU LEU PHE LEU PHE ILE ILE ILE PHE ALA LEU LEU
            565                 570                 575

GGC ATG CAG CTC TTC GGG GGG CGG TAC GAC TTC GAG GAC ACG GAA GTG  1766
GLY MET GLN LEU PHE GLY GLY ARG TYR ASP PHE GLU ASP THR GLU VAL
            580                 585                 590

CGA CGC AGC AAC TTC GAC AAC TTC CCC CAG GCC CTC ATC AGC GTC TTC  1824
ARG ARG SER ASN PHE ASP ASN PHE PRO GLN ALA LEU ILE SER VAL PHE
            595                 600                 605

CAG GTG CTG ACG GGT GAG GAC TGG AAC TCC GTG ATG TAC AAC GGG ATC  1872
GLN VAL LEU THR GLY GLU ASP TRP ASN SER VAL MET TYR ASN GLY ILE
    610                 615                 620

ATG GCC TAC GGA GGC CCG TCC TAC CCG GGC GTT CTC GTG TGC ATC TAT  1920
MET ALA TYR GLY GLY PRO SER TYR PRO GLY VAL LEU VAL CYS ILE TYR
625                 630                 635                 640

TTC ATC ATC CTT TTT GTC TGC GGC AAC TAT ATC CTG CTG AAT GTC TTC  1968
PHE ILE ILE LEU PHE VAL CYS GLY ASN TYR ILE LEU LEU ASN VAL PHE
            645                 650                 655

CTG GCC ATC GCC GTG GAC AAC CTG GCC GAG GCC GAG AGC CTG ACT TCC  2016
LEU ALA ILE ALA VAL ASP ASN LEU ALA GLU ALA GLU SER LEU THR SER
            660                 665                 670

GCG CAA AAG GCC AAG GCC GAG GAG AGG AAA CGT AGG AAG ATG TCC AGG  2064
ALA GLN LYS ALA LYS ALA GLU GLU ARG LYS ARG ARG LYS MET SER ARG
            675                 680                 685     P

GGT CTC CCT GAC AAG ACG GAG GAG GAG AAG TCT GTG ATG GCC AAG AAG  2112
GLY LEU PRO ASP LYS THR GLU GLU GLU LYS SER VAL MET ALA LYS LYS
    690                 695                 700

CTG GAG CAG AAG CCC AAG GGG GAG GGC ATC CCC ACC ACT GCC AAG CTC  2160
LEU GLU GLN LYS PRO LYS GLY GLU GLY ILE PRO THR THR ALA LYS LEU
705                 710                 715                 720

AAG GTC GAT GAG TTC GAA TCT AAC GTC AAC GAG GTG AAG GAC CCC TAC  2208
LYS VAL ASP GLU PHE GLU SER ASN VAL ASN GLU VAL LYS ASP PRO TYR
            725                 730                 735
```

FIGURE 1e

```
CCT TCA GCT GAC TTC CCA GGG GAT GAT GAG GAG GAC GAG CCT GAG ATC 2256
PRO SER ALA ASP PHE PRO GLY ASP ASP GLU GLU ASP GLU PRO GLU ILE
        740             745                 750

CCA GTG AGC CCC CGA CCG CGC CCG CTG GCC GAG CTG CAG CTC AAA GAG 2304
PRO VAL SER PRO ARG PRO ARG PRO LEU ALA GLU LEU GLN LEU LYS GLU
        755             760                 765

AAG GCA GTG CCC ATC CCG GAA GCC AGC TCC TTC TTC ATC TTC AGT CCC 2352
LYS ALA VAL PRO ILE PRO GLU ALA SER SER PHE PHE ILE PHE SER PRO
        770             775                 780

ACC AAT AAG GTC CGT GTC CTG TGT CAC CGC ATC GTC AAC GCC ACC TGG 2400
THR ASN LYS VAL ARG VAL LEU CYS HIS ARG ILE VAL ASN ALA THR TRP
785             790                 795     *           800

TTC ACC AAC TTC ATC CTG CTC TTC ATC CTG CTC AGC AGT GCT GCG CTG 2448
PHE THR ASN PHE ILE LEU LEU PHE ILE LEU LEU SER SER ALA ALA LEU
                805             810                 815

GCC GCC GAG GAC CCC ATC CGG GCG GAG TCC GTG AGG AAT CAG ATC CTT 2496
ALA ALA GLU ASP PRO ILE ARG ALA GLU SER VAL ARG ASN GLN ILE LEU
            820             825                 830

GGA TAT TTT GAT ATT GCC TTC ACC TCT GTC TTC ACT GTG GAG ATT GTC 2544
GLY TYR PHE ASP ILE ALA PHE THR SER VAL PHE THR VAL GLU ILE VAL
        835             840                 845

CTC AAG ATG ACA ACC TAC GGC GCC TTC CTG CAC AAG GGC TCC TTC TGC 2592
LEU LYS MET THR THR TYR GLY ALA PHE LEU HIS LYS GLY SER PHE CYS
        850             855                 860

CGC AAC TAC TTC AAC ATC CTG GAC CTG CTG GTG GTG GCC GTG TCT CTC 2640
ARG ASN TYR PHE ASN ILE LEU ASP LEU LEU VAL VAL ALA VAL SER LEU
865         870             875                 880

ATC TCC ATG GGT CTC GAG TCC AGC ACC ATC TCC GTG GTA AAG ATC CTG 2688
ILE SER MET GLY LEU GLU SER SER THR ILE SER VAL VAL LYS ILE LEU
                885             890             895

AGA GTG CTA AGG GTG CTC CGG CCC CTG CGA GCC ATC AAC AGA GCC AAA 2736
ARG VAL LEU ARG VAL LEU ARG PRO LEU ARG ALA ILE ASN ARG ALA LYS
            900             905                 910
```

FIGURE 1f

```
GGG TTG AAG CAC GTG GTC CAG TGC GTG TTC GTG GCC ATC CGC ACC ATC 2784
GLY LEU LYS HIS VAL VAL GLN CYS VAL PHE VAL ALA ILE ARG THR ILE
        915                 920                 925

GGG AAC|ATC GTC CTG GTC ACC ACG CTC CTG CAG TTC ATG TTC GCC TGC 2832
GLY ASN|ILE VAL LEU VAL THR THR LEU LEU GLN PHE MET PHE ALA CYS
    930             935                 940

ATC GGT GTC CAG CTC TTC|AAG GGC AAG TTC TTC AGC TGC AAT GAC CTA 2880
ILE GLY VAL GLN LEU PHE|LYS GLY LYS PHE PHE SER CYS ASN ASP LEU
945             950                 955                 960

TCC AAG ATG ACA GAA GAG GAG TGC AGG GGC TAC TAC TAT GTG TAC AAG 2928
SER LYS MET THR GLU GLU GLU CYS ARG GLY TYR TYR TYR VAL TYR LYS
                965                 970                 975

GAC GGG GAC CCC ACG CAG ATG GAG CTG CGC CCC CGC CAG TGG ATA CAC 2976
ASP GLY ASP PRO THR GLN MET GLU LEU ARG PRO ARG GLN TRP ILE HIS
            980                 985                 990

AAT GAC TTC CAC TTT GAC AAC GTG CTG TCG GCC ATG ATG TCG CTC TTC 3024
ASN ASP PHE HIS PHE ASP ASN VAL LEU SER ALA MET MET SER LEU PHE
        995                 1000                1005

ACG GTG TCC ACC TTC GAG GGA TGG CCC CAG CTG CTG TAC AGG GCC ATA 3072
THR VAL SER THR PHE GLU GLY TRP PRO GLN LEU LEU TYR ARG ALA ILE
    1010                1015                1020

GAC TCC AAC GAG GAG GAC ATG GGC CCC GTT TAC AAC AAC CGA GTG GAG 3120
ASP SER ASN GLU GLU ASP MET GLY PRO VAL TYR ASN ASN ARG VAL GLU
1025                1030                1035                1040

|ATG GCC ATC TTC TTC ATC ATC TAC ATC ATC CTC ATT GCC TTC TTC ATG 3168
|MET ALA ILE PHE PHE ILE ILE TYR ILE ILE LEU ILE ALA PHE PHE MET
            1045                1050                1055

ATG AAC ATC TTT GTG GGC TTT GTC ATC|GTC ACC TTC CAG GAG CAG GGG 3216
MET ASN ILE PHE VAL GLY PHE VAL ILE|VAL THR PHE GLN GLU GLN GLY
            1060                1065                1070

GAG ACG GAG TAC AAG AAC TGC GAG CTG GAC AAG AAC CAG CGC CAG TGT 3264
GLU THR GLU TYR LYS ASN CYS GLU LEU ASP LYS ASN GLN ARG GLN CYS
        1075                1080                1085

GTG CAG TAT GCC CTG AAG GCC CGC CCA CTT CGG TGC TAC ATC CCC AAG 3312
VAL GLN TYR ALA LEU LYS ALA ARG PRO LEU ARG CYS TYR ILE PRO LYS
    1090                1095                1100
```

FIGURE 1g

```
AAC CCA TAC CAG TAC CAG GTG TGG TAC GTC GTC ACC TCC TCC TAC TTT  3360
ASN PRO TYR GLN TYR GLN VAL TRP TYR VAL VAL THR SER SER TYR PHE
1105                1110                1115                1120

GAA TAC CTG ATG TTC GCC CTC ATC ATG CTC AAC ACC ATC TGC CTG GGC  3408
GLU TYR LEU MET PHE ALA LEU ILE MET LEU ASN THR ILE CYS LEU GLY
                    1125                1130                1135

ATG CAG CAC TAC CAC CAG TCG GAG GAG ATG AAC CAC ATC TCA GAC ATC  3456
MET GLN HIS TYR HIS GLN SER GLU GLU MET ASN HIS ILE SER ASP ILE
                1140                1145                1150

CTC AAT GTG GCC TTC ACC ATC ATC TTC ACG CTG GAG ATG ATT CTC AAG  3504
LEU ASN VAL ALA PHE THR ILE ILE PHE THR LEU GLU MET ILE LEU LYS
        1155                1160                1165

CTC TTG GCG TTC AAG GCC AGG GGC TAT TTC GGA GAC CCC TGG AAT GTG  3552
LEU LEU ALA PHE LYS ALA ARG GLY TYR PHE GLY ASP PRO TRP ASN VAL
        1170                1175                1180

TTC GAC TTC CTG ATC GTC ATC GGC AGC ATC ATT GAC GTC ATC CTC AGC  3600
PHE ASP PHE LEU ILE VAL ILE GLY SER ILE ILE ASP VAL ILE LEU SER
1185                1190                1195                1200

GAG ATC GAC ACT TTC CTG GCC TCC AGC GGG GGA CTG TAT TGC CTG GGT  3648
GLU ILE ASP THR PHE LEU ALA SER SER GLY GLY LEU TYR CYS LEU GLY
                    1205                1210                1215

GGC GGC TGC GGG AAC GTT GAC CCA GAC GAG AGC GCC CGC ATC TCC AGT  3696
GLY GLY CYS GLY ASN VAL ASP PRO ASP GLU SER ALA ARG ILE SER SER
                1220                1225                1230

GCC TTC TTC CGC CTG TTC CGG GTT ATG AGG CTG ATC AAG CTG CTG AGT  3744
ALA PHE PHE ARG LEU PHE ARG VAL MET ARG LEU ILE LYS LEU LEU SER
        1235                1240                1245

CGG GCC GAG GGC GTG CGC ACG CTG CTG TGG ACG TTC ATC AAG TCC TTC  3792
ARG ALA GLU GLY VAL ARG THR LEU LEU TRP THR PHE ILE LYS SER PHE
    1250                1255                1260

CAG GCC CTG CCC TAC GTG GCC CTG CTC ATC GTC ATG CTG TTC TTC ATC  3840
GLN ALA LEU PRO TYR VAL ALA LEU LEU ILE VAL MET LEU PHE PHE ILE
1265                1270                1275                1280
```

FIGURE 1h

```
TAC GCC GTC ATC GGC ATG CAG ATG TTT|GGA AAG ATC GCC CTG GTG GAC  3888
TYR ALA VAL ILE GLY MET GLN MET PHE|GLY LYS ILE ALA LEU VAL ASP
                1285                 1290            1295

GGG ACC CAG ATC AAC CGC AAC AAC AAC TTC CAG ACC TTC CCG CAG GCC  3936
GLY THR GLN ILE ASN ARG ASN ASN ASN PHE GLN THR PHE PRO GLN ALA
            1300                1305                1310

GTG CTG CTG CTC TTC AGG TGT GCG ACA GGG GAG GCG TGG CAA GAG ATC  3984
VAL LEU LEU LEU PHE ARG CYS ALA THR GLY GLU ALA TRP GLN GLU ILE
        1315                1320                1325

CTG CTG GCC TGC AGC TAC GGG AAG TTG TGC GAC CCA GAG TCA GAC TAC  4032
LEU LEU ALA CYS SER TYR GLY LYS LEU CYS ASP PRO GLU SER ASP TYR
    1330                1335                1340

GCC CCG GGC GAG GAG TAC ACG TGT GGC ACC AAC TTC |GCC TAC TAC TAC  4080
ALA PRO GLY GLU GLU TYR THR CYS GLY THR ASN PHE |ALA TYR TYR TYR
1345                1350                1355                1360

TTC ATC AGC TTC TAC ATG CTC TGC GCC TTC CTG ATC ATC AAC CTC TTC  4128
PHE ILE SER PHE TYR MET LEU CYS ALA PHE LEU ILE ILE ASN LEU PHE
                1365                1370                1375

GTG GCT GTC ATC ATG|GAC AAC TTT GAC TAC CTG ACA CGC GAC TGG TCC  4176
VAL ALA VAL ILE MET|ASP ASN PHE ASP TYR LEU THR ARG ASP TRP SER
            1380                1385                1390

ATC CTG GGC CCT CAC CAC CTG GAC GAG TTC AAG GCC ATC TGG GCA GAG  4224
ILE LEU GLY PRO HIS HIS LEU ASP GLU PHE LYS ALA ILE TRP ALA GLU
        1395                1400                1405

TAT GAC CCA GAG GCC AAG GGG CGA ATC AAG CAC CTG GAC GTG GTG ACC  4272
TYR ASP PRO GLU ALA LYS GLY ARG ILE LYS HIS LEU ASP VAL VAL THR
    1410                1415                1420

CTG CTG AGA AGG ATC CAG CCC CCT CTG GGC TTC GGG AAG TTC TGT CCA  4320
LEU LEU ARG ARG ILE GLN PRO PRO LEU GLY PHE GLY LYS PHE CYS PRO
1425                1430                1435                1440

CAC CGG GTG GCC TGT AAG CGC CTG GTG GGC ATG AAC ATG CCC CTG AAC  4368
HIS ARG VAL ALA CYS LYS ARG LEU VAL GLY MET ASN MET PRO LEU ASN
            1445                1450                1455

AGT GAC GGC ACG GTC ACC TTC AAT GCC ACG CTC TTT GCC CTG GTG CGC  4416
SER ASP GLY THR VAL THR PHE ASN ALA THR LEU PHE ALA LEU VAL ARG
        1460                *   1465                1470

ACG GCC CTC AAG ATC AAG ACA GAA GGT AAC TTC GAG CAG GCC AAC GAG  4464
THR ALA LEU LYS ILE LYS THR GLU GLY ASN PHE GLU GLN ALA ASN GLU
            1475                1480                1485
```

FIGURE 1i

```
GAG CTG AGG GCC ATC ATC AAG AAG ATC TGG AAG AGA ACC AGC ATG AAG  4512
GLU LEU ARG ALA ILE ILE LYS LYS ILE TRP LYS ARG THR SER MET LYS
        1490            1495                1500       P

CTA CTG GAC CAG GTC ATC CCT CCC ATA GGA GAT GAC GAG GTG ACC GTG  4560
LEU LEU ASP GLN VAL ILE PRO PRO ILE GLY ASP ASP GLU VAL THR VAL
1505                1510                1515                1520

GGG AAG TTC TAC GCC ACA TTC CTC ATC CAG GAG CAC TTC CGG AAG TTC  4608
GLY LYS PHE TYR ALA THR PHE LEU ILE GLN GLU HIS PHE ARG LYS PHE
                1525                1530                1535

ATG AAG CGC CAG GAG GAA TAT TAT GGG TAT CGG CCC AAG AAG GAC ACC  4656
MET LYS ARG GLN GLU GLU TYR TYR GLY TYR ARG PRO LYS LYS ASP THR
        1540                1545                1550

GTG CAG ATC CAG GCT GGG CTG CGG ACC ATA GAG GAG GAG GCG GCC CCT  4704
VAL GLN ILE GLN ALA GLY LEU ARG THR ILE GLU GLU GLU ALA ALA PRO
        1555                1560                1565

GAG ATC CGC CGC ACC ATC TCA GGA GAC CTG ACC GCC GAG GAG GAG CTG  4752
GLU ILE ARG ARG THR ILE SER GLY ASP LEU THR ALA GLU GLU GLU LEU
        1570                1575                1580
                            P

GAG AGA GCC ATG GTG GAG GCT GCG ATG GAG GAG AGG ATC TTC CGG AGG  4800
GLU ARG ALA MET VAL GLU ALA ALA MET GLU GLU ARG ILE PHE ARG ARG
1585                1590                1595                1600

ACC GGA GGC CTG TTT GGC CAG GTG GAC ACC TTC CTG GAA AGG ACC AAC  4848
THR GLY GLY LEU PHE GLY GLN VAL ASP THR PHE LEU GLU ARG THR ASN
                1605                1610                1615

TCC CTA CCC CCG GTG ATG GCC AAC CAA AGA CCG CTC CAG TTT GCT GAG  4896
SER LEU PRO PRO VAL MET ALA ASN GLN ARG PRO LEU GLN PHE ALA GLU
        1620                1625                1630

ATA GAA ATG GAA GAG CTT GAG TCG CCT GTC TTC TTG GAG GAC TTC CCT  4944
ILE GLU MET GLU GLU LEU GLU SER PRO VAL PHE LEU GLU ASP PHE PRO
        1635                1640                1645

CAA GAC GCA AGA ACC AAC CCT CTC GCT CGT GCC AAT ACC AAC AAC GCC  4992
GLN ASP ALA ARG THR ASN PRO LEU ALA ARG ALA ASN THR ASN ASN ALA
        1650                1655                1660

AAT GCC AAT GTT GCC TAT GGC AAC AGC AAC CAT AGC AAC AAC CAG ATG  5040
ASN ALA ASN VAL ALA TYR GLY ASN SER ASN HIS SER ASN ASN GLN MET
1665                1670            *   1675                1680

TTT TCC AGC GTC CAC TGT GAA AGG GAG TTC CCG GGA GAG GCG GAG ACA  5088
PHE SER SER VAL HIS CYS GLU ARG GLU PHE PRO GLY GLU ALA GLU THR
                1685                1690                1695
```

FIGURE 1j

```
CCG GCT GCC GGA CGA GGA GCC CTC AGC CAC TCC CAC AGG GCC CTG GGA  5136
PRO ALA ALA GLY ARG GLY ALA LEU SER HIS SER HIS ARG ALA LEU GLY
            1700                1705                1710

CCT CAC AGC AAG CCC TGT GCT GGA AAA CTG AAT GGG CAG CTG GTC CAG  5184
PRO HIS SER LYS PRO CYS ALA GLY LYS LEU ASN GLY GLN LEU VAL GLN
            1715                1720                1725

CCG GGA ATG CCC ATC AAC CAG GCA CCT CCT GCC CCC TGC CAG CAG CCT  5232
PRO GLY MET PRO ILE ASN GLN ALA PRO PRO ALA PRO CYS GLN GLN PRO
        1730                1735                1740

AGC ACA GAT CCC CCA GAG CGC GGG CAG AGG AGG ACC TCC CTG ACA GGG  5280
SER THR ASP PRO PRO GLU ARG GLY GLN ARG ARG THR SER LEU THR GLY
1745                    1750                1755    P       1760

TCT CTG CAA GAC GAA GCA CCC AGG AGG AGC TCC GAG GGG AGC ACC      5328
SER LEU GLN ASP GLU ALA PRO GLN ARG ARG SER SER GLU GLY SER THR
                    1765                1770  P         1775

CCC AGG CGC CCG GCT CCT GCT ACA GCT CTG CTG ATC CAA GAG GCT CTG  5376
PRO ARG ARG PRO ALA PRO ALA THR ALA LEU LEU ILE GLN GLU ALA LEU
                1780                1785                1790

GTT CGA GGG GGC CTG GAC ACC TTG GCA GCT GAT GCT GGC TTC GTC ATG  5424
VAL ARG GLY GLY LEU ASP THR LEU ALA ALA ASP ALA GLY PHE VAL MET
            1795                1800                1805

GCA ACA AGC CAG GCC CTG GTA GAC GCC TGT CAG ATG GAA CCG GAG GAA  5472
ALA THR SER GLN ALA LEU VAL ASP ALA CYS GLN MET GLU PRO GLU GLU
            1810                1815                1820

GTA GAG GTC GCA GCC ACA GAG CTA CTG AAA GAG CGA GAG TCC GTC CAG  5520
VAL GLU VAL ALA ALA THR GLU LEU LEU LYS GLU ARG GLU SER VAL GLN
1825                1830                1835                1840

GGC ATG GCC AGT GTC CCG GGA AGC CTG AGC CGC AGG TCC TCC CTG GGC  5568
GLY MET ALA SER VAL PRO GLY SER LEU SER ARG ARG SER SER LEU GLY
            1845                1850            P   1855

AGC CTT GAC CAG GTC CAG GGC TCC CAG GAA ACC CTT ATT CCT CCC AGG  5616
SER LEU ASP GLN VAL GLN GLY SER GLN GLU THR LEU ILE PRO PRO ARG
            1860                1865                1870

CCG TGA TGGCTGTGCA GTGTCCACAT GACCAAGGCG AGGGGACAG TGCGTGCAGA    5672
PRO

AGCTCAGCCC TGCATGGCAG CCTCCCTCTG TCTCAGCCCT CCTGCTGAGC           5722
TGGGGCGGTC TGGAACCGAC CAGGAAGCCA GGAGCCTCCC CTGGCCAGCA           5772
AGAGGCATGA TTCTAAAGCA TCCAGAAAGG CCTGGTCAGT GCCACTCCCC           5822
AGCAGGACAT TAAAGTCTCT AGGTCTGTGG CAAAAAAAA AAAAAAAAA             5872
AAAAAAAAAA AAAAAAAAAA AAAA                                      5897
```

FIGURE 2a

```
5'                                                         AGAAGGGA  -301
GGGCGAGCGT GGTGTGTGCG CGCTCGGGCG CCGGCGGCAC CGCCGAGGTC TGTTGGCAAA  -241
AGTCGCCCTT GATGGCGGCG GAGGCGAGGC AGCCGCGGCG CCGAACAGCC GACGCGCGCT  -181
AGCGGGGTCC GCCCGCCCCT TTCCCAGAGC CCAGCGCCGC CGTTCGCCGC CGCCGCCGCC  -121
CGCCCGCGCG CCGTTCGCCG CCGCCGCCGC CCGCGGGTGG CAGCGCCGCT CGGTCCCCGG   -61
CCCCGGGGCC GGCTGGGGGG CGGTCGGGGC GTGTGAGGGG CTTGCTCCCA GCTCGCGAAG    -1
```

| | | | | | | | | | | | | | | | | |
|---|---|---|---|---|---|---|---|---|---|---|---|---|---|---|---|---|
| ATG | GCT | GCG | GGC | CGC | CCG | CTG | GCC | TGG | ACG | CTG | ACA | CTT | TGG | CAG | GCG | 48 |
| MET | ALA | ALA | GLY | ARG | PRO | LEU | ALA | TRP | THR | LEU | THR | LEU | TRP | GLN | ALA | |
| | -25 | | | | -20 | | | | | -15 | | | | | | |

| | | | | | | | | | | | | | | | | |
|---|---|---|---|---|---|---|---|---|---|---|---|---|---|---|---|---|
| TGG | CTG | ATC | CTG | ATC | GGG | CCC | TCG | TCG | GAG | GAG | CCG | TTC | CCT | TCA | GCC | 96 |
| TRP | LEU | ILE | LEU | ILE | GLY | PRO | SER | SER | GLU | GLU | PRO | PHE | PRO | SER | ALA | |
| -10 | | | | | -5 | | | | -1 | +1 | | | | 5 | | |

| | | | | | | | | | | | | | | | | |
|---|---|---|---|---|---|---|---|---|---|---|---|---|---|---|---|---|
| GTC | ACT | ATC | AAG | TCA | TGG | GTG | GAT | AAG | ATG | CAA | GAA | GAC | CTG | GTC | ACA | 144 |
| VAL | THR | ILE | LYS | SER | TRP | VAL | ASP | LYS | MET | GLN | GLU | ASP | LEU | VAL | THR | |
| | | | 10 | | | | | 15 | | | | | 20 | | | |

| | | | | | | | | | | | | | | | | |
|---|---|---|---|---|---|---|---|---|---|---|---|---|---|---|---|---|
| CTG | GCA | AAA | ACA | GCA | AGT | GGA | GTC | AAT | CAG | CTT | GTT | GAT | ATT | TAT | GAG | 192 |
| LEU | ALA | LYS | THR | ALA | SER | GLY | VAL | ASN | GLN | LEU | VAL | ASP | ILE | TYR | GLU | |
| | | 25 | | | | 30 | | | | | 35 | | | | | |

| | | | | | | | | | | | | | | | | |
|---|---|---|---|---|---|---|---|---|---|---|---|---|---|---|---|---|
| AAA | TAT | CAA | GAT | TTG | TAT | ACT | GTG | GAA | CCA | AAT | AAT | GCA | CGT | CAG | CTG | 240 |
| LYS | TYR | GLN | ASP | LEU | TYR | THR | VAL | GLU | PRO | ASN | ASN | ALA | ARG | GLN | LEU | |
| | 40 | | | | | 45 | | | | | 50 | | | | | |

| | | | | | | | | | | | | | | | | |
|---|---|---|---|---|---|---|---|---|---|---|---|---|---|---|---|---|
| GTG | GAA | ATT | GCA | GCC | AGA | GAC | ATT | GAG | AAG | CTT | CTC | AGC | AAC | AGA | TCT | 288 |
| VAL | GLU | ILE | ALA | ALA | ARG | ASP | ILE | GLU | LYS | LEU | LEU | SER | ASN | ARG | SER | |
| 55 | | | | | 60 | | | | | 65 | | | * | | 70 | |

| | | | | | | | | | | | | | | | | |
|---|---|---|---|---|---|---|---|---|---|---|---|---|---|---|---|---|
| AAA | GCC | CTG | GTG | CGC | CTG | GCT | TTG | GAA | GCA | GAG | AAA | GTT | CAA | GCA | GCC | 336 |
| LYS | ALA | LEU | VAL | ARG | LEU | ALA | LEU | GLU | ALA | GLU | LYS | VAL | GLN | ALA | ALA | |
| | | | | 75 | | | | | 80 | | | | | 85 | | |

| | | | | | | | | | | | | | | | | |
|---|---|---|---|---|---|---|---|---|---|---|---|---|---|---|---|---|
| CAC | CAA | TGG | AGG | GAA | GAT | TTT | GCA | AGC | AAT | GAA | GTT | GTC | TAC | TAT | AAC | 384 |
| HIS | GLN | TRP | ARG | GLU | ASP | PHE | ALA | SER | ASN | GLU | VAL | VAL | TYR | TYR | ASN | |
| | | | 90 | | | | | 95 | | | | | 100 | | | |

| | | | | | | | | | | | | | | | | |
|---|---|---|---|---|---|---|---|---|---|---|---|---|---|---|---|---|
| GCG | AAG | GAT | GAT | CTT | GAT | CCT | GAA | AAA | AAT | GAC | AGT | GAA | CCA | GGC | AGC | 432 |
| ALA | LYS | ASP | ASP | LEU | ASP | PRO | GLU | LYS | ASN | ASP | SER | GLU | PRO | GLY | SER | |
| | | 105 | | | | | 110 | | * | | | 115 | | | | |

| | | | | | | | | | | | | | | | | |
|---|---|---|---|---|---|---|---|---|---|---|---|---|---|---|---|---|
| CAG | AGG | ATC | AAA | CCT | GTT | TTC | ATT | GAC | GAT | GCT | AAC | TTT | AGA | AGA | CAA | 480 |
| GLN | ARG | ILE | LYS | PRO | VAL | PHE | ILE | ASP | ASP | ALA | ASN | PHE | ARG | ARG | GLN | |
| | | 120 | | | | 125 | | | | | 130 | | | | | |

| | | | | | | | | | | | | | | | | |
|---|---|---|---|---|---|---|---|---|---|---|---|---|---|---|---|---|
| GTA | TCC | TAT | CAG | CAC | GCA | GCT | GTC | CAT | ATC | CCC | ACT | GAC | ATC | TAT | GAA | 528 |
| VAL | SER | TYR | GLN | HIS | ALA | ALA | VAL | HIS | ILE | PRO | THR | ASP | ILE | TYR | GLU | |
| 135 | | | | 140 | | | | | 145 | | | | | 150 | | |

FIGURE 2b

```
GGA TCG ACA ATC GTG TTA AAC GAA CTC AAC TGG ACA AGT GCC TTA GAT    576
GLY SER THR ILE VAL LEU ASN GLU LEU ASN TRP THR SER ALA LEU ASP
            155                 160                 165
                                 *

GAC GTT TTC AAA AAA AAT CGA GAG GAA GAC CCT TCA CTG TTG TGG CAG    624
ASP VAL PHE LYS LYS ASN ARG GLU GLU ASP PRO SER LEU LEU TRP GLN
            170                 175                 180

GTG TTT GGC AGT GCC ACT GGC CTG GCC CGG TAT TAC CCA GCT TCT CCA    672
VAL PHE GLY SER ALA THR GLY LEU ALA ARG TYR TYR PRO ALA SER PRO
            185                 190                 195

TGG GTT GAT AAT AGC CGA ACC CCA AAC AAG ATT GAT CTT TAT GAT GTA    720
TRP VAL ASP ASN SER ARG THR PRO ASN LYS ILE ASP LEU TYR ASP VAL
        200                 205                 210

CGC AGA AGA CCA TGG TAC ATC CAA GGT GCT GCA TCC CCT AAA GAT ATG    768
ARG ARG ARG PRO TRP TYR ILE GLN GLY ALA ALA SER PRO LYS ASP MET
215                 220                 225                 230

CTT ATT CTG GTG GAT GTG AGT GGA AGC GTT AGT GGA CTG ACA CTC AAA    816
LEU ILE LEU VAL ASP VAL SER GLY SER VAL SER GLY LEU THR LEU LYS
                235                 240                 245

CTC ATC CGG ACA TCC GTC TCC GAA ATG TTG GAA ACC CTC TCA GAT GAT    864
LEU ILE ARG THR SER VAL SER GLU MET LEU GLU THR LEU SER ASP ASP
            250                 255                 260

GAT TTT GTG AAC GTG GCT TCA TTT AAC AGC AAT GCT CAG GAT GTA AGC    912
ASP PHE VAL ASN VAL ALA SER PHE ASN SER ASN ALA GLN ASP VAL SER
            265                 270                 275

TGC TTT CAG CAC CTT GTC CAA GCA AAT GTA AGA AAT AAG AAA GTG TTG    960
CYS PHE GLN HIS LEU VAL GLN ALA ASN VAL ARG ASN LYS LYS VAL LEU
            280                 285                 290

AAA GAT GCA GTG AAT AAT ATC ACA GCA AAA GGA ATC ACA GAT TAT AAG   1008
LYS ASP ALA VAL ASN ASN ILE THR ALA LYS GLY ILE THR ASP TYR LYS
295                 300                 305                 310
                     *

AAG GGC TTT AGT TTT GCT TTT GAG CAG CTG CTT AAT TAT AAT GTA TCC   1056
LYS GLY PHE SER PHE ALA PHE GLU GLN LEU LEU ASN TYR ASN VAL SER
            315                 320             *   325

AGA GCC AAC TGC AAT AAG ATT ATC ATG TTG TTC ACG GAC GGA GGA GAA   1104
ARG ALA ASN CYS ASN LYS ILE ILE MET LEU PHE THR ASP GLY GLY GLU
            330                 335                 340
```

FIGURE 2c

```
GAG AGA GCC CAG GAG ATA TTT GCC AAA TAC AAT AAA GAC AAG AAA GTA   1152
GLU ARG ALA GLN GLU ILE PHE ALA LYS TYR ASN LYS ASP LYS LYS VAL
        345             350                 355

CGT GTA TTC ACA TTC TCA GTT GGC CAA CAT AAT TAC GAC AGA GGA CCT   1200
ARG VAL PHE THR PHE SER VAL GLY GLN HIS ASN TYR ASP ARG GLY PRO
        360             365                 370

ATT CAG TGG ATG GCT TGC GAA AAT AAA GGT TAT TAT TAT GAA ATT CCA   1248
ILE GLN TRP MET ALA CYS GLU ASN LYS GLY TYR TYR TYR GLU ILE PRO
375             380                 385                     390

TCC ATT GGA GCC ATA AGA ATT AAT ACT CAG GAA TAC CTA GAT GTT CTG   1296
SER ILE GLY ALA ILE ARG ILE ASN THR GLN GLU TYR LEU ASP VAL LEU
                395                 400                 405

GGA AGA CCG ATG GTT TTA GCA GGA GAC AAA GCT AAG CAA GTC CAA TGG   1344
GLY ARG PRO MET VAL LEU ALA GLY ASP LYS ALA LYS GLN VAL GLN TRP
            410                 415                 420

ACA AAT GTG TAC CTG GAT GCA CTG GAA CTG GGA CTT GTC ATT ACT GGA   1392
THR ASN VAL TYR LEU ASP ALA LEU GLU LEU GLY LEU VAL ILE THR GLY
                425                 430                 435

ACT CTT CCG GTC TTC AAC ATA ACT GGC CAA TTT GAA AAT AAG ACA AAC   1440
THR LEU PRO VAL PHE ASN ILE THR GLY GLN PHE GLU ASN LYS THR ASN
        440         *   445                 450  *

TTA AAG AAC CAG CTG ATT CTT GGA GTG ATG GGA GTT GAT GTG TCT TTG   1488
LEU LYS ASN GLN LEU ILE LEU GLY VAL MET GLY VAL ASP VAL SER LEU
455             460                 465                 470

GAA GAT ATT AAA AGA CTG ACA CCA CGT TTT ACA CTC TGC CCC AAT GGC   1536
GLU ASP ILE LYS ARG LEU THR PRO ARG PHE THR LEU CYS PRO ASN GLY
                475                 480                 485

TAC TAT TTT GCA ATT GAT CCT AAT GGT TAT GTG TTA TTA CAT CCA AAT   1584
TYR TYR PHE ALA ILE ASP PRO ASN GLY TYR VAL LEU LEU HIS PRO ASN
            490                 495                 500

CTT CAG CCA AAG CCT ATT GGT GTA GGT ATA CCA ACA ATT AAT TTG AGA   1632
LEU GLN PRO LYS PRO ILE GLY VAL GLY ILE PRO THR ILE ASN LEU ARG
        505                 510                 515

AAA AGG AGA CCC AAT GTT CAG AAC CCC AAA TCT CAG GAG CCA GTG ACA   1680
LYS ARG ARG PRO ASN VAL GLN ASN PRO LYS SER GLN GLU PRO VAL THR
        520                 525                 530

TTG GAT TTC CTC GAT GCA GAG TTG GAG AAT GAC ATT AAA GTG GAG ATT   1728
LEU ASP PHE LEU ASP ALA GLU LEU GLU ASN ASP ILE LYS VAL GLU ILE
535             540                 545                     550
```

FIGURE 2d

| | | | | | | | | | | | | | | | | |
|---|---|---|---|---|---|---|---|---|---|---|---|---|---|---|---|---|
| CGA | AAT | AAA | ATG | ATC | GAT | GGA | GAA | AGT | GGA | GAA | AAA | ACA | TTC | AGA | ACT | 1766 |
| ARG | ASN | LYS | MET | ILE | ASP | GLY | GLU | SER | GLY | GLU | LYS | THR | PHE | ARG | THR | |
| | | | 555 | | | | | 560 | | | | | | 565 | | |

| | | | | | | | | | | | | | | | | |
|---|---|---|---|---|---|---|---|---|---|---|---|---|---|---|---|---|
| CTG | GTT | AAA | TCT | CAA | GAT | GAG | AGA | TAT | ATT | GAC | AAA | GGA | AAC | AGG | ACA | 1824 |
| LEU | VAL | LYS | SER | GLN | ASP | GLU | ARG | TYR | ILE | ASP | LYS | GLY | ASN | ARG | THR | |
| | | | 570 | | | | | 575 | | | | | * | | | |
| | | | | | | | | | | | | | 580 | | | |

| | | | | | | | | | | | | | | | | |
|---|---|---|---|---|---|---|---|---|---|---|---|---|---|---|---|---|
| TAC | ACG | TGG | ACT | CCT | GTC | AAC | GGC | ACA | GAT | TAT | AGC | AGT | TTG | GCC | TTG | 1872 |
| TYR | THR | TRP | THR | PRO | VAL | ASN | GLY | THR | ASP | TYR | SER | SER | LEU | ALA | LEU | |
| | | | 585 | | | * | 590 | | | | | 595 | | | | |

| | | | | | | | | | | | | | | | | |
|---|---|---|---|---|---|---|---|---|---|---|---|---|---|---|---|---|
| GTA | TTA | CCA | ACC | TAC | AGT | TTT | TAC | TAT | ATA | AAA | GCC | AAA | ATA | GAA | GAG | 1920 |
| VAL | LEU | PRO | THR | TYR | SER | PHE | TYR | TYR | ILE | LYS | ALA | LYS | ILE | GLU | GLU | |
| | | 600 | | | | 605 | | | | | 610 | | | | | |

| | | | | | | | | | | | | | | | | |
|---|---|---|---|---|---|---|---|---|---|---|---|---|---|---|---|---|
| ACA | ATA | ACT | CAG | GCC | AGA | TAT | TCA | GAA | ACA | CTG | AAA | CCG | GAT | AAT | TTT | 1968 |
| THR | ILE | THR | GLN | ALA | ARG | TYR | SER | GLU | THR | LEU | LYS | PRO | ASP | ASN | PHE | |
| 615 | | | | | 620 | | | | | 625 | | | | | 630 | |

| | | | | | | | | | | | | | | | | |
|---|---|---|---|---|---|---|---|---|---|---|---|---|---|---|---|---|
| GAA | GAA | TCT | GGC | TAC | ACA | TTC | CTA | GCA | CCA | AGA | GAT | TAC | TGC | AGT | GAC | 2016 |
| GLU | GLU | SER | GLY | TYR | THR | PHE | LEU | ALA | PRO | ARG | ASP | TYR | CYS | SER | ASP | |
| | | | | 635 | | | | | 640 | | | | | 645 | | |

| | | | | | | | | | | | | | | | | |
|---|---|---|---|---|---|---|---|---|---|---|---|---|---|---|---|---|
| CTT | AAA | CCT | TCA | GAT | AAT | AAC | ACT | GAA | TTT | CTT | TTA | AAT | TTC | AAT | GAG | 2064 |
| LEU | LYS | PRO | SER | ASP | ASN | ASN | THR | GLU | PHE | LEU | LEU | ASN | PHE | ASN | GLU | |
| | | | 650 | | * | | | 655 | | | | | 660 | | | |

| | | | | | | | | | | | | | | | | |
|---|---|---|---|---|---|---|---|---|---|---|---|---|---|---|---|---|
| TTT | ATT | GAT | AGA | AAA | ACT | CCA | AAC | AAC | CCA | TCC | TGT | AAT | ACA | GAC | TTG | 2112 |
| PHE | ILE | ASP | ARG | LYS | THR | PRO | ASN | ASN | PRO | SER | CYS | ASN | THR | ASP | LEU | |
| | | | 665 | | | | 670 | * | | | | 675 | | | | |

| | | | | | | | | | | | | | | | | |
|---|---|---|---|---|---|---|---|---|---|---|---|---|---|---|---|---|
| ATT | AAT | AGA | GTC | TTG | CTG | GAT | GCA | GGC | TTT | ACA | AAT | GAA | CTT | GTT | CAA | 2160 |
| ILE | ASN | ARG | VAL | LEU | LEU | ASP | ALA | GLY | PHE | THR | ASN | GLU | LEU | VAL | GLN | |
| | | | 680 | | | | 685 | | | | | 690 | | | | |

| | | | | | | | | | | | | | | | | |
|---|---|---|---|---|---|---|---|---|---|---|---|---|---|---|---|---|
| AAT | TAC | TGG | AGT | AAG | CAG | AAG | AAT | ATC | AAG | GGA | GTG | AAA | GCA | CGG | TTT | 2208 |
| ASN | TYR | TRP | SER | LYS | GLN | LYS | ASN | ILE | LYS | GLY | VAL | LYS | ALA | ARG | PHE | |
| 695 | | | | | 700 | | | | | 705 | | | | | 710 | |

| | | | | | | | | | | | | | | | | |
|---|---|---|---|---|---|---|---|---|---|---|---|---|---|---|---|---|
| GTT | GTG | ACT | GAT | GGT | GGG | ATT | ACC | AGA | GTT | TAT | CCC | AAA | GAG | GCT | GGA | 2256 |
| VAL | VAL | THR | ASP | GLY | GLY | ILE | THR | ARG | VAL | TYR | PRO | LYS | GLU | ALA | GLY | |
| | | | | 715 | | | | | 720 | | | | | 725 | | |

| | | | | | | | | | | | | | | | | |
|---|---|---|---|---|---|---|---|---|---|---|---|---|---|---|---|---|
| GAA | AAT | TGG | CAG | GAA | AAC | CCA | GAG | ACA | TAT | GAA | GAC | AGC | TTC | TAT | AAA | 2304 |
| GLU | ASN | TRP | GLN | GLU | ASN | PRO | GLU | THR | TYR | GLU | ASP | SER | PHE | TYR | LYS | |
| | | | 730 | | | | | 735 | | | | | 740 | | | |

| | | | | | | | | | | | | | | | | |
|---|---|---|---|---|---|---|---|---|---|---|---|---|---|---|---|---|
| AGG | AGC | CTC | GAT | AAT | GAT | AAC | TAC | GTT | TTC | ACT | GCT | CCC | TAC | TTT | AAC | 2352 |
| ARG | SER | LEU | ASP | ASN | ASP | ASN | TYR | VAL | PHE | THR | ALA | PRO | TYR | PHE | ASN | |
| | | | 745 | | | | | 750 | | | | | 755 | | * | |

FIGURE 2e

```
AAA AGT GGA CCT GGG GCC TAT GAG TCA GGC ATT ATG GTA AGC AAA GCT    2400
LYS SER GLY PRO GLY ALA TYR GLU SER GLY ILE MET VAL SER LYS ALA
    760                 765                 770

GTA GAA ATA TAT ATC CAA GGA AAA CTT CTT AAA CCT GCA GTT GTT GGA    2448
VAL GLU ILE TYR ILE GLN GLY LYS LEU LEU LYS PRO ALA VAL VAL GLY
775                 780                 785                 790

ATT AAA ATT GAT GTA AAT TCT TGG ATA GAG AAT TTC ACC AAA ACT TCA    2496
ILE LYS ILE ASP VAL ASN SER TRP ILE GLU ASN PHE THR LYS THR SER
                795                 800  *              805

ATC AGG GAT CCG TGT GCT GGT CCA GTT TGT GAC TGC AAA CGA AAC AGT    2544
ILE ARG ASP PRO CYS ALA GLY PRO VAL CYS ASP CYS LYS ARG ASN SER
            810                 815                 820
                                                         P

GAT GTA ATG GAT TGT GTG ATT CTA GAT GAC GGT GGG TTT CTT TTG ATG    2592
ASP VAL MET ASP CYS VAL ILE LEU ASP ASP GLY GLY PHE LEU LEU MET
            825                 830                 835

GCC AAC CAT GAT GAT TAT ACC AAT CAG ATT GGA AGA TTC TTT GGA GAG    2640
ALA ASN HIS ASP ASP TYR THR ASN GLN ILE GLY ARG PHE PHE GLY GLU
    840                 845                 850

ATT GAT CCA AGC TTG ATG AGA CAC CTG GTC AAT ATA TCA GTT TAT GCC    2688
ILE ASP PRO SER LEU MET ARG HIS LEU VAL ASN ILE SER VAL TYR ALA
855                 860                 865                 870
                                         *

TTT AAC AAA TCT TAT GAT TAT CAG TCG GTG TGT GAA CCT GGT GCT GCG    2736
PHE ASN LYS SER TYR ASP TYR GLN SER VAL CYS GLU PRO GLY ALA ALA
    *           875                 880                 885

CCA AAG CAG GGA GCA GGG CAC CGC|TCG GCT TAT GTG CCA TCA ATA GCA    2784
PRO LYS GLN GLY ALA GLY HIS ARG|SER ALA TYR VAL PRO SER ILE ALA
            890                 895                 900

GAC ATA CTG CAG ATT GGA TGG TGG GCC ACT GCT GCT GCC TGG TCT ATT    2832
ASP ILE LEU GLN ILE GLY TRP TRP ALA THR ALA ALA ALA TRP SER ILE
            905                 910                 915

CTT|CAG CAG TTT CTG TTG AGT TTG ACT TTT CCA CGG CTC CTT GAG GCA    2880
LEU|GLN GLN PHE LEU LEU SER LEU THR PHE PRO ARG LEU LEU GLU ALA
        920                 925                 930

GCT GAT ATG GAG GAT GAC GAC TTC ACT GCC TCC ATG TCA AAG CAG AGC    2928
ALA ASP MET GLU ASP ASP ASP PHE THR ALA SER MET SER LYS GLN SER
935                 940                 945                 950
```

FIGURE 2f

```
TGC ATC ACT GAG CAA ACC CAG TAT TTC TTC GAT AAT GAC AGC AAA TCG   2976
CYS ILE THR GLU GLN THR GLN TYR PHE PHE ASP ASN ASP SER LYS SER
            955                 960    *            965

TTC AGT GGG GTA TTA GAC TGT GGG AAT TGT TCC AGA ATC TTT CAT GTA   3024
PHE SER GLY VAL LEU ASP CYS GLY ASN CYS SER ARG ILE PHE HIS VAL
            970                 975                 980
                                 *
GAA AAG CTC ATG AAC ACC AAT TTA ATA TTC ATA ATG GTA GAG AGC AAG   3072
GLU LYS LEU MET ASN THR ASN LEU ILE PHE ILE MET VAL GLU SER LYS
        985                 990                 995

GGG ACA TGT CCC TGT GAC ACA CGG CTG CTC ATA CAA GCA GAG CAA ACT   3120
GLY THR CYS PRO CYS ASP THR ARG LEU LEU ILE GLN ALA GLU GLN THR
    1000                1005                1010

TCT GAT GGA CCA GAT CCT TGT GAT ATG GTT AAG CAA CCC AGA TAT CGA   3168
SER ASP GLY PRO ASP PRO CYS ASP MET VAL LYS GLN PRO ARG TYR ARG
1015                1020                1025                1030

AAA GGG CCA GAT GTC TGC TTT GAC AAC AAT GTC CTG GAG GAT TAT ACT   3218
LYS GLY PRO ASP VAL CYS PHE ASP ASN ASN VAL LEU GLU ASP TYR THR
                1035                1040                1045

GAC TGC GGT GGG GTC TCT GGA TTA AAT|CCT TCC CTG TGG TCC ATC ATC   3264
ASP CYS GLY GLY VAL SER GLY LEU ASN|PRO SER LEU TRP SER ILE ILE
            1050                1055                1060
                                 *
GGG ATA CAG TTT GTA CTG CTT TGG CTG GTT TCT GGC AGC|AGA CAC TGC   3312
GLY ILE GLN PHE VAL LEU LEU TRP LEU VAL SER GLY SER|ARG HIS CYS
        1065                1070                1075

CTG TTA TGA CCTTCTAAAA CCAAATCTCC ATAATTAAAC TCCAGACCCT           3361
LEU LEU
    1080

GCCACAACAT GATCCCTCCG TTATGTTAAA GTAGGGTCAA CTGTTAAATC             3411
AGAACATTAG CTGGGCCTCT GCCATGGCAG AGCCCTAAGG CGCAGACTCA             3461
TCAGGCACCC ACTGGCTGCA TGTCAGGGTG TCC ...... 3'                    3494
```

FIGURE 3a

```
         Human Neuronalα2
........................GGGCGGGGGAGGGGGATTGATCTTC    25
Rabbit Skeletal Muscleα2 ||||| | ||||||| |     |
CCCGGGGCCGGCTGGGGGGCGGTCGGGGCGTGTGAGGGGCTTGCTCCCAG   299
            Start
GATCGCAAGATGGCTGCTGGCTGCCTGCTGGCCTTGACTCTGACACTTTT    75
       |||||||||||  |||  |||  ||||||||  |||  |||||||||||
CTCGCGAAGATGGCTGCGGGCCGCCCGCTGGCCTGGACGCTGACACTTTG   349

CCAATCTT......TGCTCATCGGCCCCTCGTCGGAGGAGCCGTTCCCTT   119
  ||  |  |      |  ||  |||||  ||||||||||||||||||||||||||||
Gcaggcgtggctgatcctgatcgggccctcgtcggaggagccgttccctt   399

CGGCCGTCACTATCAAATCATGGGTGGATAAGATGCAAGAAGACCTTGTC   169
| |||||||||||||||  ||||||||||||||||||||||||||||||  |||
cagccgtcactatcaagtcatgggtggataagatgcaagaagacctggtc   449

ACACTGGCAAAAACAGCAAGTGGAGTCAATCAGCTTGTTGATATTTATGA   219
||||||||||||||||||||||||||||||||||||||||||||||||||
acactggcaaaaacagcaagtggagtcaatcagcttgttgatatttatga   499

GAAATATCAAGATTTGTATACTGTGGAACCAAATAATGCACGCCAGCTGG   269
||||||||||||||||||||||||||||||||||||||||||  |||||||
gaaatatcaagatttgtatactgtggaaccaaataatgcacgtcagctgg   549

TAGAAATTGCAGCCAGGGATATTGAGAAACTTCTGAGCAACAGATCTAAA   319
| ||||||||||||||  ||  |||||||||  |||||  ||||||||||||||
tggaaattgcagccagagacattgagaagcttctcagcaACAGATCTAAA   599

GCCCTGGTGAGCCTGGCATTGGAAGCGGAGAAAGTTCAAGCAGCTCACCA   369
||||||||  |||||||  |||||||||  ||||||||||||||||||  |||||
GCCCTGGTGCGCCTGGCTTTGGAAGCAGAGAAAGTTCAAGCAGCCCACCA   649
```

FIGURE 3b

```
GTGGAGAGAAGATTTTGCAAGCAATGAAGTTGTCTACTACAATGCAAAGG  419
|||||  |||||||||||||||||||||||||||||||||| || || ||||
ATGGAGGGAAGATTTTGCAAGCAATGAAGTTGTCTACTATAACGCGAAGG  699

ATGATCTCGATCCTGAGAAAAATGACAGTGAGCCAGGCAGCCAGAGGATA  469
|||||||  |||||||| ||||||||||||||  ||||||||||||||||
ATGATCTTGATCCTGAAAAAAATGACAGTGAACCAGGCAGCCAGAGGATC  749

AAACCTGTTTTCATTGAAGATGCTAATTTTGGACGACAAATATCTTATCA  519
|||||||||||||||||| ||||||||| || |||||| ||||| |||||
AAACCTGTTTTCATTGACGATGCTAACTTTAGAAGACAAGTATCCTATCA  799

GCACGCAGCAGTCCATATTCCTACTGACATCTATGAGGGCTCAACAATTG  569
|||||||| ||||||||| || ||||||||||||||| ||  ||||| |
GCACGCAGCTGTCCATATCCCCACTGACATCTATGAAGGATCGACAATCG  849

TGTTAAATGAACTCAACTGGACAAGTGCCTTAGATGAAGTTTTCAAAAAG  619
|||||| |||||||||||||||||||||||||||||| |||||||||||
TGTTAAACGAACTCAACTGGACAAGTGCCTTAGATGACGTTTTCAAAAAA  899

AATCGCGAGGAAGACCCTTCATTATTGTGGCAGGTTTTTGGCAGTGCCAC  669
||||| ||||||||||||||||| | ||||||||||| |||||||||||||
AATCGAGAGGAAGACCCTTCACTGTTGTGGCAGGTGTTTGGCAGTGCCAC  949

TGGCCTAGCTCGATATTATCCAGCTTCACCATGGGTTGATAATGGTAGAA  719
||||| || || |||||| |||||||| ||||||||||||||||| |||
TGGCCTGGCCCGGTATTACCCAGCTTCTCCATGGGTTGATAATAGCCGAA  999

CTCCAAATATGATTGACCTTTATGATGTACGCAGAAGACCATGGTACATC  769
| |||||| ||||||| |||||||||||||||||||||||||||||||||
CCCCAAACAAGATTGATCTTTATGATGTACGCAGAAGACCATGGTACATC  1049

CAAGGAGCTGCATCTCCTAAAGACATGCTTATTCTGGTGGATGTGAGTGG  819
||||| ||||||||| ||||||| ||||||||||||||||||||||||||
CAAGGTGCTGCATCCCCTAAAGATATGCTTATTCTGGTGGATGTGAGTGG  1099
```

FIGURE 3c

```
AAGTGTTAGTGGATTGACACTTAAACTGATCCGAACATCTGTCTCCGAAA  869
||| ||||||||| |||||| ||||| ||||| ||||| |||||||||||
AAGCGTTAGTGGACTGACACTCAAACTCATCCGGACATCCGTCTCCGAAA  1149

TGTTAGAAACCCTCTCAGATGATGATTTCGTGAATGTAGCTTCATTTAAC  919
|||| ||||||||||||||||||||||| ||||| || ||||||||||||
TGTTGGAAACCCTCTCAGATGATGATTTTGTAACGTGGCTTCATTTAAC   1199

AGCAATGCTCAGGATGTAAGCTGTTTTCAGCACCTTGTCCAAGCAAATGT  969
||||||||||||||||||||||| |||||||||||||||||||||||||
AGCAATGCTCAGGATGTAAGCTGCTTTCAGCACCTTGTCCAAGCAAATGT  1249

AAGAAATAAAAAGTGTTGAAAGACGCGGTGAATAATATCACAGCCAAAG   1019
|||||||||  |||||||||||| | ||||||||||||||||| ||||
AAGAAATAAGAAAGTGTTGAAAGATGCAGTGAATAATATCACAGCAAAAG  1299

GAATTACAGATTATAAGAAGGGCTTTAGTTTTGCTTTTGAACAGCTGCTT  1069
|||| ||||||||||||||||||||||||||||||||| |||||||||
GAATCACAGATTATAAGAAGGGCTTTAGTTTTGCTTTTGAGCAGCTGCTT  1349

AATTATAATGTTTCCAGAGCAAACTGCAATAAGATTATTATGCTATTCAC  1119
||||||||||  |||||||| |||||||||||||||| ||| | |||||
AATTATAATGTATCCAGAGCCAACTGCAATAAGATTATCATGTTGTTCAC  1399

GGA...TGGAGAAGAGAGAGCCCAGGAGATATTTAACAAATACAATAAAG  1166
|||       ||||||||||||||||||||||||||| ||||||||||||
GGACGGAGGAGAAGAGAGAGCCCAGGAGATATTTGCCAAATACAATAAAG  1449

ATAAAAACTACCTGTATTCACCTTCTCAGTTGGTCAACACAATTATGAC   1216
| || ||| ||| ||||||||| |||||||||| ||||| ||||| |||
ACAAGAAAGTACGTGTATTCACATTCTCAGTTGGCCAACATAATTACGAC  1499
```

FIGURE 3d

```
AGAGGACCTATTCAGTGGATGGCCTGTGAAAACAAAGGTTATTATTATGA   1266
||||||||||||||||||||||||  ||||||| ||||||||||||||||
AGAGGACCTATTCAGTGGATGGCTTGCGAAAATAAAGGTTATTATTATGA   1549

AATTCCTTCCATTGGTGCAATAAGAATCAATACTCAGGAATATTTGGATG   1316
||||||  ||||||||| || ||||||||| |||||||||||||  ||||
AATTCCATCCATTGGAGCCATAAGAATTAATACTCAGGAATACCTAGATG   1599

TTTTGGGAAGACCAATGGTTTTAGCAGGAGACAAAGCTAAGCAAGTCCAA   1366
|| ||||||||||| |||||||||||||||||||||||||||||||||||
TTCTGGGAAGACCGATGGTTTTAGCAGGAGACAAAGCTAAGCAAGTCCAA   1649

TGGACAAATGTGTACCTGGATGCATTGGAACTGGGACTTGTCATTACTGG   1416
|||||||||||||||||||||||| |||||||||||||||||||||||||
TGGACAAATGTGTACCTGGATGCACTGGAACTGGGACTTGTCATTACTGG   1699

AACTCTTCCGGTCTTCAACATAACCGGCCAATTTGAAAATAAGACAAACT   1466
|||||||||||||||||||||||| |||||||||||||||||||||||||
AACTCTTCCGGTCTTCAACATAACTGGCCAATTTGAAAATAAGACAAACT   1749

TAAAGAACCAGCTGATTCTTGGTGTGATGGGAGTAGATGTGTCTTTGGAA   1516
||||||||||||||||||||| ||||||||||||| ||||||||||||||
TAAAGAACCAGCTGATTCTTGGAGTGATGGGAGTTGATGTGTCTTTGGAA   1799

GATATTAAAAGACTGACACCACGTTTTACACTGTGCCCCAATGG......   1560
||||||||||||||||||||||||||||||||| ||||||||||
GATATTAAAAGACTGACACCACGTTTTACACTCTGCCCCAATGGCTACTA   1849
```

PROBES AND ASSAYS FOR CALCIUM CHANNEL $\alpha_2$ SUBUNIT-ENCODING NUCLEIC ACIDS This application is a divisional of U.S. application Ser. No. 07/914,231, filed Jul. 13, 1992, now U.S. Pat. No. 5,407,820, which is a continuation of U.S. application Ser. No. 07/603,751, filed Nov. 8, 1990, now abandoned, which is a continuation-in-part of U.S. application Ser. No. 07/176,899, filed Apr. 4, 1988, now abandoned. U.S. application Ser. No. 07/603,751 was filed as International PCT Application PCT/US89/01408, on Apr. 4, 1989.

TECHNICAL FIELD

The present invention relates to molecular biology and pharmacology.

More particularly, the invention relates to calcium channel compositions and methods of making and using same.

BACKGROUND OF THE INVENTION

Calcium channels are membrane-spanning, multisubunit proteins that allow controlled entry of $Ca^{+2}$ ions into cells from the extracellular fluid. All cells throughout the animal kingdom, and at least some bacterial, fungal and plant cells, possess one or more types of calcium channel.

The most common type of calcium channel is voltage-dependent. In a voltage-dependent channel, the "opening," to allow an influx of $Ca^{+2}$ ions into the cells to begin, requires a depolarization to a certain level of the potential difference between the inside of the cell bearing the channel and the extracellular medium bathing the cell and the rate of influx of $Ca^{+2}$ into the cell depends on this potential difference. All "excitable" cells in animals, such as neurons of the central nervous systems, peripheral nerve cells, and muscle cells, including those of skeletal muscles, cardiac muscles, and venous and arterial smooth muscles, have voltage-dependent calcium channels.

Calcium channels are physiologically important because the channels have a central role in regulating intracellular $Ca^{+2}$ levels and these levels are important for cell viability and function. Thus, intracellular $Ca^{+2}$ concentrations are implicated in a number of vital processes in animals, such as neurotransmitter release, muscle contraction, pacemaker activity, and secretion of hormones and other substances.

A number of compounds useful in treating various diseases in animals, including humans, are thought to exert their beneficial effects by modulating functions of voltage-dependent calcium channels. Many of these compounds bind to calcium channels and block, or reduce the rate of, influx of $Ca^{+2}$ into cells in response to depolarization of the inside and outside of the cells.

An understanding of the pharmacology of compounds that interact with calcium channels, and the ability to rationally design compounds that will interact with calcium channels to have desired therapeutic effects, have been hampered by a lack of understanding of the structure of channel subunits and the genes that code for them. Thus, it has not been possible to obtain the large amounts of highly purified channel subunits that are required to understand, at the molecular level, the nature of the subunits and their interactions with one another, with the cell membranes across which the channels allow $Ca^{+2}$ ions to pass, with $Ca^{+2}$ and other ions, and with low molecular weight compounds that affect channel function. For example, with the availability of large amounts of purified calcium channel subunits, functional channels could be prepared and used to screen the effects of compounds on channel function, thereby providing a basis for the design of therapeutic agents which affect the calcium channel, or various combinations of channel subunits could be crystallized and have their structures determined to high resolution employing X-ray or neutron diffraction techniques, providing yet another basis for rational design of therapeutic agents that affect channel function.

Certain diseases, such as Lambert-Eaton Syndrome, involve autoimmune interactions with calcium channels. The ready availability of calcium channel subunits would make possible immunoassays for the diagnosis of such diseases and an understanding of them at the molecular level that could lead to effective methods for treating them.

The lack of information on genes that code for calcium channel subunits has prevented the understanding of the molecular properties of the mature calcium channel subunits and their precursor proteins (i.e., the mature subunits with signal peptides appended to the amino-terminus) and the regulation of expression of calcium channel subunits. An understanding of these properties, and of how expression of calcium channel subunit genes is regulated, may provide the basis for designing therapeutic agents which have beneficial effects through affecting calcium channel function or concentration. Furthermore, the availability of sequences of genes coding for calcium channel subunits would make possible the diagnosis of defects, which might underlie a number of diseases, in genes coding for such subunits.

The availability of a DNA with the sequence of a segment, of at least about 12, and more preferably at least about 30, nucleotides of a cDNA encoding a subunit of a calcium channel from the cells of a tissue of an animal would make possible the isolation and cloning of cDNA's, and possibly genomic DNA's, coding for the corresponding subunit of different calcium channels from the same or different tissues and animals of the same or different species. The availability of the sequences of numerous full-length cDNA's coding for corresponding subunits of calcium channels from a variety of tissues and animal species would contribute to elucidating structure-function relationships in the subunits and this knowledge, in turn, would be useful in the design of therapeutic agents whose activities are exerted through binding to calcium channels.

Voltage-dependent calcium channels are thought to consist of two large subunits, of between about 130 and about 200 kilodaltons ("kD") in molecular weight, and a number (generally thought to be one or three) of different smaller subunits, of less than about 60 kD in molecular weight. At least one of the larger subunits and possibly some of the smaller are glycosylated. Some of the subunits are capable of being phosphorylated. There is confusion in the art concerning the naming of the various subunits of voltage-dependent calcium channels.

The two large subunits of voltage-dependent calcium channels are designated herein the "(alpha)$_1$-subunit" and the "(alpha)$_2$-subunit".

The (alpha)$_1$-subunit is not detectably changed in molecular weight when treated with dithiothreitol ("DTT") or with enzymes which catalyze removal of N-linked sugar groups from glycosylated proteins. The (alpha)$_1$-subunit has a molecular weight of about 150 to about 170 kD when analyzed by sodium dodecylsulfate ("SDS")-polyacrylamide gel electrophresis ("PAGE") after isolation from mammalian muscle tissue and has specific binding sites for various 1,4-dihydropyridines ("DHPs") and phenylalkylamines.

The (alpha)$_2$-subunit is somewhat less well characterized than the (alpha)$_1$-subunit. The molecular weight of the (alpha)$_2$-subunit As at least about 130–150 kD, as determined by SDS-PAGE analysis in the presence of DTT after isolation from mammalian muscle tissue. However, in SDS-PAGE under non-reducing conditions (in the presence of N-ethylmaleimide), the (alpha)$_2$-subunit migrates with a band of about 160–190 kD. It is not known in the art whether the smaller fragment (of about 30 kD), which appears to be released upon reduction, is the product of a gene different from the gene which encodes the 130–150 kD fragment (and, consequently, the two fragments are different subunits of the calcium channel) or whether both fragments are products of the same genes (and, consequently, the (alpha)$_2$-subunit is about 160–190 kD and is split into (at least) two fragments upon reduction). There is evidence that the (alpha)$_2$-subunit, whatever its size, and the corresponding fragment produced under reducing conditions, whether part of the (alpha)$_2$-subunit or not, are glycosylated with at least N-linked sugars and do not have specified binding sites for 1,4-dihydropyridines and phenylalkylamines that are known to bind to the (alpha)$_1$-subunit.

Reference herein to the precursor of an (alpha)$_1$-subunit means the protein with the amino acid sequence corresponding to the sequence of the full-length mRNA which, upon translation, results, ultimately, in (alpha)$_1$-subunit resident as part of a calcium channel in a cell membrane. The precursor protein is convened by various processing steps into the (alpha)$_1$-subunit. The details of the processing between the precursor and the mature (alpha)$_1$-subunit are not clear, but the processing possibly involves phosphorylation and also cleavage of the primary translation product to yield the mature (alpha)$_1$-subunit of the calcium channel.

Similarly, reference herein to the precursor of an (alpha)$_2$-subunit means the protein with the amino acid sequence corresponding to the sequence of the full-length mRNA which, upon translation, results, ultimately, in (alpha)$_2$-subunit resident as part of a calcium channel in a cell membrane. The precursor protein is converted by various processing steps into the (alpha)$_2$-subunit. As with the (alpha)$_1$-subunit, the details of the processing between the precursor and the mature (alpha)$_2$-subunit are not clear, but the processing presumably involves at least removal of a leader sequence (i.e., a signal peptide), glycosylation, and, possibly, cleavage to yield what are now thought to be other subunits of the calcium channel.

The cDNA and corresponding amino acid sequence of the (alpha)$_1$-subunit precursor of a rabbit back skeletal muscle calcium channel has been reported. Tanabe et al., Nature 328, 313–318 (1987).

Calcium channel activity, measured electrophysiologically by voltage-clamp techniques, has been induced in Xenopus laevis oocytes when total mRNA isolated from mammalian brain and cardiac muscle is injected into the oocytes. Also, it has been reported that calcium channel-containing preparations, when reconstituted into lipid bilayers, confer voltage-dependent calcium channel activity on the bilayers.

However, there is no evidence that the (alpha)$_1$-subunit alone or the (alpha)$_2$-subunit alone provides a functional calcium channel in oocytes, lipid bilayers or any other situation. It has been recently reported by Hofmann, et al., Trends in Pharmacolog. Sci. 8, 393–398 (1987) that mRNA prepared using the cDNA of (alpha)$_1$-subunit obtained by Tanabe, et al. was unable to induce calcium channel activity in Xenopus laevis oocytes.

BRIEF DESCRIPTION OF THE FIGURES

FIGS. 1a–1j set forth the nucleotide sequence of the cDNA encoding the (alpha)$_1$-subunit of the rabbit skeletal calcium channel (SEQ ID NO: 1) and the amino acid sequence encoded by the 5,619 nucleotide open reading frame, which encodes a sequence of 1,873 amino acids. The 3' non-coding sequence of the cDNA is 234 nucleotides in length, excluding the poly (dA) tract, and contains a consensus polyadenylation signal ATTAAA (nucleotides 5832–5837) 17 nucleotides upstream from the poly (dA) tract.

FIGS. 2a–2f set forth the 3,802 nucleotide and amino acid sequences of the rabbit skeletal calcium channel (alpha)$_2$-subunit (SEQ ID NO: 2). The figure includes the nucleotides of the cDNA that encodes the (alpha)$_2$-subunit precursor, including the 308 nucleotides of the 5' untranslated sequence, the 3,318 nucleotide open reading frame and 176 nucleotides of 3' untranslated sequence. The signal peptide of the (alpha)$_2$-subunit is shown as the first 26 negatively numbered amino acids.

FIGS. 3a–3d compare the sequences of the DNA encoding the human neuronal $\alpha_2$-subunit (SEQ 10 NO: 3) with that encoding the rabbit skeletal $\alpha_2$-subunit.

The boxes in the figures enclose transmembrane regions. The symbol, P, denotes a phosphorylation site and the symbol, *, indicates a N-glycosylation site.

DETAILED DESCRIPTION OF THE INVENTION

In short, we have discovered a cDNA which codes for the (alpha)$_1$-subunit of an animal calcium channel (see FIGS. 1a–1j) and a cDNA which codes for the (alpha)$_2$-subunit of an animal calcium channel (see FIGS. 2a–2f and Example 4).

Thus in one of its aspects, the invention is a DNA which comprises a cDNA which codes for the (alpha)$_2$-subunit of an animal calcium channel, and the RNA, coding for such a subunit, made upon transcription of such a DNA according to the invention.

In another of its aspects, the invention is a substantially pure (alpha)$_2$-subunit of an animal calcium channel.

By a "substantially pure" subunit or protein is meant a subunit or protein that is sufficiently free of other polypeptide contaminants to be considered homogeneous by SDS-PAGE or to be unambiguously sequenced.

In another of its aspects, the invention entails an eukaryotic cell with an heterologous calcium channel, said cell made by a process comprising administering to said cell a first composition, which consists essentially of a first RNA which is translatable in said cell into the precursor of the (alpha)$_1$-subunit of a calcium channel of an animal of a first species, and a second composition which consists essentially of a second RNA which is translatable in said cell into the precursor of the (alpha)$_2$-subunit of a calcium channel of an animal of a second species, said first and second species being the same or different, provided that at least one of said precursor of said (alpha)$_1$-subunit and said precursor of said (alpha)$_2$-subunit is foreign to said cell. Preferred cells for this purpose are Xenopus laevis oocytes.

In another of its aspects, the invention entails a method for assaying a compound for calcium channel agonist or antagonist activity which comprises electrophysiologically measuring the calcium channel activity of a cell described in the immediately preceeding paragraph when such cell is exposed to a solution of the compound being tested for such activity. For similar methods applied with Xenopus laevis oocytes and acetylcholine receptors, see e.g., Mishina et al. Nature 313, 364 (1985) and, with such oocytes and sodium channels, see Noda et al., Nature 322, 826–828 (1986).

In a further of its aspects, the invention is an eukaryotic cell containing a DNA which comprises a cDNA which can be expressed to make the (alpha)$_2$-subunit of a calcium channel. Such a cell according to the invention can also contain a DNA which comprises a cDNA which can be expressed to make the (alpha)$_1$-subunit of a calcium channel. Preferably, the (alpha)$_2$-subunit or the (alpha)$_1$-subunit made from such a cDNA in such a cell will be foreign to the cell, i.e., will have an amino acid sequence which differs from that of any calcium channel (alpha)$_1$-subunit or (alpha)$_2$-subunit which occurs in a cell of the same type which does not contain a DNA from which the (alpha)$_1$-subunit or the (alpha)$_2$-subunit encoded by such a cDNA is expressed. Preferred among such cells are those of mammalian origin, such as COS cells, NIH3T3 cells, mouse L cells or the like, or those of yeast such as S. cerevisiae or P. pastoris. Methods of making such cells of the invention, by transforming cells with suitable heterologous DNAs, to be maintained in the cell as episomes or (preferably) integrated into chromosomal DNA of the cell, and then culturing transformants or sub-culturing (or passaging, in the case of mammalian cells) from such a culture or a subculture thereof, are well known to those of ordinary skill.

Among such cells of the invention, the invention entails also an eukaryotic cell with an heterologous calcium channel, said calcium channel made by a process comprising expression of a first cDNA, which codes for the precursor of the (alpha)$_1$-subunit of a calcium channel of an animal of a first species, and a second cDNA, which codes for the precursor of the (alpha)$_2$-subunit of a calcium channel of a second species, said first and second species being the same or different. Usually at least one of said precursor of said (alpha)$_1$-subunit and said precursor of said (alpha)$_2$-subunit is foreign to said cell. Again, preferred among such cells are those of mammalian origin or those of yeast such as S. cerevisiae cells or P. pastoris. In a preferred embodiment, such a cell will also contain another heterologous gene, which comprises a transcriptional control element (e.g., a promoter or promoter/enhancer combination), which is active in said cell and the transcriptional activity of which responds to an ion or molecule capable of entering said cell through a functional calcium channel (e.g., Ca$^{++}$, Ba$^{++}$, Ca$^{++}$ ionophores), linked operatively for expression to a structural gene for an indicator protien, such a chloramphenicol acetyltransferase, luciferase or β-galactosidase.

These cells of the invention, which have functional, foreign calcium channels (i.e., functional calcium channels wherein at least one of the (alpha)$_1$-subunit and the (alpha)$_2$-subunit is foreign to the cell) will be useful for, among other purposes, assaying a compound for calcium channel agohist'or antagonist activity. First, such a cell can be employed to measure the affinity of such a compound for the functional calcium channel. Secondly, such a cell can be employed to measure electrophysiologically the calcium channel activity in the presence of the compound being tested as well as a ion or molecule, such as Ca$^{++}$ or Ba$^{++}$, which is known to be capable of entering the cell through the functional channel. For similar studies which have been carried out with the acetylcholine receptor, see Claudio et al. Science 238 1688–1694 (1987). These methods for assaying a compound for calcium channel agohist or antagonist activity are also part of the present invention.

Such cells according to the invention, in the preferred embodiment, wherein the cell also contains an heterologous gene with a transcriptional control element, which is active in the cell and responsive to an ion or molecule capable of entering the cell through a functional calcium channel and is linked operatively for expression to a structural gene for an indicator protein, can also be employed, in another method according to the invention for assaying a compound for calcium channel agohist or antagonist activity. This method comprises exposing a culture of such cells to a solution of a compound being tested for such activity, together with an ion or molecule, which is capable of entering the cells through a functional calcium channel and affecting the activity of the transcriptional control element controlling transcription of the gene for the indicator protein, and comparing the level of expression, in the cells of the culture, of the gene for the indicator protein with the level of such expression in the cells of another, control culture of such cells.

A "control culture," as clearly understood by the skilled, will be a culture that is, and is treated, substantially the same as the culture exposed to the compound being assayed except that the control culture is not exposed to the compound being assayed. Levels of expression of the genes for the indicator proteins are ascertained readily by the skilled by known methods, which involve measurements of the concentration of indicator protein via assays for detectable compounds produced in reactions catalyzed by the indicator protein.

As indicated above, indicator proteins are enzymes which are active in the cells of the invention and catalyze production of readily detectable compounds (e.g., chromogens, fluorescent compounds).

In a still further aspect, the invention is a method for diagnosing Lambert-Eaton Syndrome in a person by immunoassay which method comprises combining serum from the person with (alpha)$_1$-subunit of a first animal species and (alpha)$_2$-subunit of a second animal species (the same as or different from the first species) and ascertaining whether antibodies in the serum react with one or both of the subunits to a greater extent than antibodies in control serum (e.g., from a person or group of persons known to be free of the Syndrome). Any immunoassay procedure known in the art for detecting antibodies in serum against a given antigen can be employed in the method. Preferably, in the method, both of the (alpha) subunits are from a mammalian calcium channel, most preferably human.

The invention entails also a labeled (e.g., $^{32}$P or a biotinylated) RNA or single-stranded DNA of at least 12 (preferably at least 30) bases in length in a sequence which comprises a sequence of at least 12 (preferably at least 30) contiguous bases between bases −238 and 3495, inclusive, in FIGS. 2a–2f, or such a labeled RNA or single-stranded DNA with a sequence taken from the cDNA, described in Example 4, which encodes an human neuronal (alpha)$_2$-subunit. The use of such DNAs and RNAs as probes, to identify and isolate cDNAs coding calcium channel (alpha)$_2$- subunits or to identify tissue in which (alpha)$_2$-subunit mRNA is made, is clear to the skilled. In this regard, see, e.g., Example 4.

The primary strategy for cloning cDNAs encoding the (alpha)$_1$ and the (alpha)$_2$ polypeptide subunits of the DHP-sensitive calcium channels from rabbit skeletal muscle was to screen rabbit back skeletal muscle lambda gt11 cDNA expression libraries with antibody probes specific to each of the proteins. See generally Ausubel et al. Current Protocols in Molecular Biology, Wiley-interscience, New York (1987); Davis et al. Basic Methods in Molecular Biology, Elsevier Science Publishing Co., New York (1986). Monoclonal antibodies capable of immunoprecipitating the $M_r$ 155K–170K DHP receptor (alpha)$_1$ protein from rabbit skeletal muscle triads have been described previously by Leung, et al. J. Biol Chem. 262, 7943–7946 (1987). Polyclonal antisera specific for the (alpha)$_2$ polypeptide subunit was prepared in guinea pigs using SDS polyacrylamide gel purified (alpha)$_2$ protein as described by Nakayama, et al. J. Biol. Chem. 262, 6572–6576 (1987). One of the (alpha)$_1$-specific monoclonal antibodies, designated as IIF7 by Leung, et al. supra, and the (alpha)$_2$-specific polyclonal antisera were used for screening of 1.0×10$^6$ recombinant phages of an oligo-dT primed lambda gt11 cDNA library. Probes based on the Tanabe et al. (alpha)$_1$-subunit cDNA sequence (Nature 328, 313–318 (1987)) could also be used to identify clones with fragments of the (alpha)$_1$-subunit cDNA.

Once a positive clone was found using an antibody-screening method, the clone was used to screen further for overlapping clones. A sequential series of overlapping clones was thus generated. These clones were sequenced and fragments were subcloned into either pIBI 24/25 (IBI, New Haven, Conn.) or M13 mp18/19. In cloning the (alpha)$_1$-subunit, the DNA sequence was compared to the primary sequence of the DHP receptor (alpha)$_1$-subunit reported by Tanabe et al. Nucleotide differences resulting in amino acid differences were confirmed by sequencing in both directions.

As pertains to the (alpha)$_1$-subunit, initially, two cDNA clones which reacted positively with the IIF7 monoclonal antibody were isolated and found to be related by cross-hybridization.

DNA sequencing of one of these clones revealed the presence of a cDNA insert of 453 base pairs (bp). Significantly, this insert coded for a 151 amino acid open reading frame with 28% homology to a region for the Electrophorus electroplax sodium channel sequence. The cDNA insert derived from this clone was used to rescreen the lambda gt11 cDNA library and a rabbit back skeletal muscle Okayama-Berg cDNA library (MacLennan, et al., Nature 316, 696–700 (1985)) to isolate overlapping cDNA clones. The cDNA clones were analyzed using the dideoxy chain-termination method of Sanger to determine the entire coding sequence of the (alpha)$_1$ subunit of the calcium channel and a restriction map was made for comparison and orientation of DNA sequences.

An oligo-dT-primed expression cDNA library was constructed in lambda gt11, using young adult rabbit back skeletal muscle poly (A+) RNA (kindly provided by J. Robbins, University of Cincinnati) isolated in guanidine isothiocyanate (see Gubler, et al., Gene 25, 263–269 (1983); Lapeyre, et al., Gene 37, 215–220 (1985); Huynh et. al, DNA Cloning: A Practical Approach, Vol. I 49–78 (IRE, Oxford, 1985)). Double-strand cDNA was synthesized and EcoRI adapters were added. After the addition of the adapters, the double-strand cDNA was size-selected on a Sepharose CL-4B or Bio-Gel A-50 m column. Fragments>1500 bp were ligated into EcoRI digested, dephosphorylated lambda gt11. The library was packaged in vitro with Gigapack-plus, (Stratagene, San Diego, Calif.) and an efficiency of >95% recombinants was determined by plating in the presence of X-gal and IPTG. Two clones of a total 1×10$^6$ recombinants were identified by screening the expression library with monoclonal Ab IIF7 reactive with the $M_r$ 170,000 (alpha)$_1$ subunit of the rabbit skeletal muscle calcium channel. Positive plaques were visualized by binding HRP-goat anti-mouse IgG followed by color development with 4-chloro-1-naphthol. Each clone contained a ~500 bp insert and was related by cross-hybridization. One clone was DNA sequenced to identify an open reading frame (nts 2847–3300) and was used to identify a 6.5 Kb transcript by Northern analysis The 453 bp insert noted above was used to rescreen the lambda gt11 library and 8 of 1×10$^6$ clones were positive. One clone (1700 bp) extended the farthest 5' to nt 2237; its 522 bp PstI fragment, nts 2294–2816, was used to screen 1×10$^6$ transformants of a rabbit back skeletal muscle cDNA library constructed according to the method of Okayama and Berg (see MacLannan, et. al., Nature 316, 696–700 (1985)). Three positive clones were isolated, of which the largest (5.0 Kb) extended 5' to nt ~750. The Okayama-Berg cDNA library was rescreened with a 5' 250 bp (PstI)-EcoRI fragment (the PstI site is donated by the Okayama-Berg vector) (nts ~750–1006). The longest clone isolated, of 5 positives, was 5.3 Kb, extending 5' to nt ~450. To clone the 5' end of (alpha)$_1$, a random primed rabbit back skeletal muscle lambda gt11 cDNA library was synthesized as described above with the following modifications: (1) pd(N)$_6$ hexamers (Pharmacia, Inc. Piscathaway, N.J.) were used to random prime the first strand cDNA reaction, (2) Adapters containing NcoI, KpnI, and EcoRI sites:

5'-CCATGGTACCTTCGTTGACG-3'
3'-GGTACCATGGAAGCAACTGCTTAA-5' were ligated to the double-strand cDNA as described above, and (3) the double-strand cDNA was size-selected on a 1 ml Bio-Gel A50 m column. Fragments>600 bp were ligated into lambda gt11. 1×10$^6$ recombinants of this library were screened in duplicate with the 1,648 bp EcoRI/XhoI fragment corresponding to nt 1006–2653 and an oligonucleotide probe spanning the initiating methionine 5'-GGGAAGCCATGGAGCCATCCTCACCCCAGG-3'. Forty clones were positive with both probes, of which one (1.55 Kb) extended 78 nts 5' of the start codon and ~450 bp 3' of the EcoRI site.

FIGS. 1a–1j shows the 5,975 nucleotide sequence of the cDNA encoding the (alpha)$_1$-subunit. There is a 5,619 nucleotide sequence reading frame which encodes a sequence of 1,873 amino acids (FIGS. 1a–1j). The sequence context of the designated initiation codon is consistent with the proposed consensus sequence of Kozak, Nucleic Acids Res. 15, 8125–8132 (1987). The 3' non-coding sequence of the cDNA is 234 nucleotides in length, excluding the poly (dA) tract, and contains a consensus polyadenylation signal ATTAAA (nucleotides 5832–5837) 17 nucleotides upstream from the poly (dA) tract. This cDNA sequence is consistent with an ~6,500 nucleotide DHP receptor (alpha)$_1$ mRNA. Furthermore, the DNA sequence is 99.4% identical to the cDNA sequence encoding the DHP receptor reported by Tanabe, et. al., supra. Nucleotide differences were identified at 33 positions, of which three, nucleotides 5423, 5444 and 5504 also result in amino acid changes.

FIGS. 2a–2f also show the signal peptide of the (alpha)$_2$-subunit, shown as the first 26 negatively numbered amino acids. An arrow identifies the cleavage site between the signal peptide and the mature (alpha)$_2$-subunit. The N-terminal amino acid sequence previously determined is shown in bold sequence (Thr(+8), Trp(+12), and Asp(+14) were not previously determined.) The nucleotide sequence shown was determined from two clones which overlapped to span the coding sequence of the (alpha)$_2$-subunit. Five nucleotide differences among individual clones were observed resulting in four amino acid changes. Differences occurred in the sequence at positions 169, 347, 348, 984, and a deletion of nts 1858–1860. The amino acids were finally determined to be as follows: Asn at residue 31, Lys at residue 90, and a deletion of Set at residue 594. An in-frame upstream stop codon is underlined as well as the start and stop codons of an upstream short open reading frame. Three putative transmembrane regions are enclosed in boxes. Potential N-glycosylation and phosphorylation sites are indicated as described for FIGS. 1a–1j.

The open reading frame encodes a sequence of 1,106 amino acids (FIGS. 2a–2f). The previously determined $NH_2$-terminal amino acid sequence of the (alpha)$_2$ protein is encoded by nucleotides 79–129 in the same open reading frame (amino acid residues 1–17, FIGS. 2a–2f). The nucleotide sequence adjacent to the designated initiating codon agrees with the proposed consensus sequence. An in-frame termination codon is present upstream beginning at nucleotide –27. In addition, an out-of-frame potential initiation codon is located beginning at nucleotide –229 and is followed by a nonsense codon at nucleotides –179 to –181. The 5' untranslated sequence of the (alpha)$_2$ cDNA, 308 nucleotides clone and sequenced thus far, is unusually long. This region is extremely G+C rich, approximately 80% G+C, which is similar to other relatively long 5' non-coding sequences which have been reported.

FIGS. 1a–1j show the 1,873 amino acid sequence deduced from the cDNA (SEQ. ID NO. 1) of the (alpha)$_1$ subunit of the rabbit skeletal muscle calcium channel. Based on the identification of a clone using the (alpha)$_1$-specific IIF7 monoclonal antibody, we have determined that the protein sequence encoded by the 453 bp cDNA insert (amino acid residues 950–1,100) contains the epitope recognized by this monoclonal antibody. The complete sequence yields a calculated Mr of 212,143 for the (alpha)$_1$ protein, in contrast to the observed Mr 155K–170K, previously reported by others using SDS polyacrylamide gel electrophoresis. The amino acid sequence determined and reported here is 99.8% identical to that recently described by Tanabe et al., supra, showing three amino acid differences at residues 1,808 (Thr to Met), 1,815 (Ala to Val), and 1,835 (Ala to Glu). The calcium channel (alpha)$_1$-subunit protein contains five potential N-glycosylation sites at Ash residues 79, 257, 797, 1,464, and 1,674 and seven potential cAMP-dependent phosphorylation sites at Ser residues 687, 1,502, 1,575, 1,757, 1,772, and 1,854, and Thr 1,552. Analogous to the (alpha)-subunit of the sodium channel, the (alpha)$_1$-subunit of the skeletal muscle calcium channel contains four internal repeated sequence regions. An analysis of the hydropathy profile of the (alpha)$_1$-protein sequence reveals that each repeat contains five hydrophobic segments and one segment with strong positive charge. Since the (alpha)$_1$-protein sequence lacks an hydrophobic amino-terminal sequence characteristic of a signal peptide, it has been proposed that the segments of the four internally repeated regions represent twenty-four transmembrane segments and that the amino-and carboxy-termini extend intracellularly. That model is consistent with two of the potential glycosylation sites (Asn residues 79 and 257) being localized extracellularly and all of the potential phosphorylation cites being localized intracellularly. This generally agrees with previous biochemical studies suggesting that the (alpha)$_1$-subunit (which has been identified as the putative 1,4-dihydropyridine receptor) is not glycosylated but is phosphorylated.

FIGS. 2a–2f shows the 1,106 amino acid sequence deduced from the cDNA (SEQ ID NO: 2) of the (alpha)$_2$-subunit of the rabbit skeletal muscle calcium channel. The sequence yields a calculated $M_r$ of 125,018 for this protein, in contrast to the observed $M_r$ 165K–175K (under non-reducing conditions $M_r$ 135K–150K under reducing conditions) determined previously by SDS polyacrylamide gel electrophoresis. The (alpha)$_2$ amino acid sequence deduced here from the cDNA confirms the sequence of 17 amino acids reported earlier as supposedly that of the amino terminal 17 amino acids of the (alpha)$_2$-subunit. The (alpha)$_2$- subunit precursor has a 26 amino acid (residues –1 to –26) signal peptide. While this proposed signal peptide is hydrophobic and of an appropriate length characteristic of signal sequences, it is somewhat unusual in that the peptide has Glu at position-1 and the Gln at position-12 defines a rather short central hydrophic region. The (alpha)$_2$ protein contains 18 potential N-glycosylation sites (Ash residues 68, 112, 160, 300, 324, 444, 451, 580, 589, 652, 671, 758, 801, 865, 872, 962, 975, and 1,005) and two potential cAMP-dependent phosphorylation sites at Thr 477 and Ser 822 (FIGS. 2a–2f).

An analysis of the (alpha)$_2$ protein sequence for regional hydropathy reveals that, in distinct contrast to similar analysis of the (alpha)$_1$ protein, this protein is substantially hydrophilic, although it does contain a number of hydrophobic regions. Further characterization of the hydrophobic regions of polarity index and hydrophobic moment analyses indicates that three segments may represent transmembrane domains of the (alpha)$_2$ protein. The topography of the (alpha)$_2$ protein is not, however, easily predicted from the deduced primary amino acid sequence. This problem is further compounded by the determination that the (alpha)$_2$ protein lacks significant homology with any protein in the Dayhoff protein sequence database or with other known ion channel and receptor proteins. If the proposed (alpha)$_2$ signal sequence is, in fact, cleaved between the Glu-residue at position –1 and the Glu residue at position, then the amino terminus of the mature protein would be extracellular. Furthermore, assuming that the three hydrophobic segments function as transmembrane domains, and that there are only three such domains, the carboxyl-terminus of the (alpha)$_2$ protein would be intracellular. Such a transmembrane topography would be consistent with 8 out of the 18 potential N-glycosylation sites being localized extracellularly and the single potential phosphorylation site being localized intracellularly. Previous biochemical studies indicate that the (alpha)$_2$-subunit of the skeletal muscle calcium channel is not phosphorylated but is extensively glycosylated.

Rabbit and human genomic DNAs were digested with various restriction enzymes and Southern blots of these DNAs were hybridized with radiolabeled cDNA clones specific for the (alpha)$_1$-subunit or the (alpha)$_2$-subunit. Under conditions of high stringency, very few hybridizing bands were observed in rabbit genomic DNA with either the (alpha)$_1$- or (alpha)$_2$-specific probes. This result is consistent with a low-copy number, perhaps only a single-copy, of each of the (alpha)$_1$- and (alpha)$_2$-subunit genes in the rabbit genome. Southern blot of the same DNA preparations were also probed under conditions of low stringency with the same (alpha)$_1$- and (alpha)$_2$-specific probes. While additional hybridizing bands were observed in rabbit genomic DNA under low stringency conditions with both the (alpha)$_1$- and (alpha)$_2$-specific probes, substantially greater hybridization was observed with the (alpha)$_1$-specific cDNA probes. These results suggest that the (alpha)$_1$- and (alpha)$_2$-subunits of the skeletal muscle DHP-sensitive calcium channel may share significant homology with genes encoding other voltage-dependent DHP-sensitive calcium channels, voltage-dependent calcium channels which are not DHP-sensitive (e.g., T- and N-types), and possibly ligand-gated calcium channels (e.g., glutamate receptor). Interestingly, hybridization bands were observed in human genomic DNA with the (alpha)$_1$-specific cDNA probes under both high and low stringency conditions, whereas significant hybridization of (alpha)$_2$-specific cDNA probes were observed only under low stringency conditions. Thus, while there are human genes homologous to the rabbit (alpha)$_1$- and (alpha)$_2$-subunit genes, greater evolutionary sequence divergence may have occurred in the (alpha)$_2$ gene relative to the (alpha)$_1$ gene.

A further aspect of the invention provides for a diagnostic assay for Lambert Eaton Syndrome (LES). LES is an autoimmune disease characterized by an insufficient release of acetylcholine from motor nerve terminals which normally are responsive to nerve impulses. A recent publication (Kim and Neher, Science 239, 405–408 (1988)) demonstrates that IgG from LES patients block individual voltage-dependent calcium channels and thus prevent function. A diagnostic assay for LES based on immunological reactivity of LES IgG with calcium channel (alpha)$_2$-subunit alone or in combination with (alpha)$_1$-subunit is thus provided for. For example, such an assay may be based on immunoprecipitation of LES IgG by the calcium channels subunits of the invention.

EXAMPLE 1

Isolation of RNA for cDNA Library

On the day before RNA is isolated, prepare the following. As a precaution, all glassware should be baked and all stock solutions in the list immediately below should be sterilized by autoclaving.

200 ml of 0.1 NaOAc, pH 5.2, 1 mM EDTA
50 ml of 0.2M Na$_2$ EDTA, pH 8.0.
50 ml of 1M Tris, pH 7.5
50 ml of 3.2 Tris, pH 7.2
50 ml of 0.01M Tris (pH 8.0), 1 mM EDTA
50 ml PK buffer (0.1M Tris, pH 7.2, 50 mM NaCl, 10 mM EDTA)
50 ml of 10% SDS,
4 l of ultrapure H$_2$O On the morning of the RNA isolation, combine:
100 ml H$_2$O
100 g guanidine isothiocyanate (IBI)
10.6 ml 1M Tris, pH 7.5
10.6 ml 0.2M EDTA Stir, but do not heat above 65° C. to dissolve guanidine isothiocyanate.

Dissect young adult rabbit a cl skeletal muscle on a clean glass plate and add about 10 g of muscle tissue (cut in ~4 mm pieces) to 50 ml of the guanidine isothiocyanate solution in e.g., a 100 ml Wheaton bottle.

Homogenize using "tissuemizer" from Tekman (large blade) for 10–20 sec., or until small pieces are no longer visible.

Place in 60° H$_2$O bath, add 30 ml of redistilled phenol which has been made 0.1% in 8-OH quinoline, 0.2% β-ME. Solution should be clear and homogenous after this addition.

Add 30 ml of a 1:1 solution of chloroform:acetate buffer.

Shake vigorously at 60° for 10 minutes the solutions should appear opaque; if not, add sufficient chloroform:acetate until it turns milky.

Cool on ice, spin to separate phases (7000×g, 10–20 minutes)

Take off and pass it vigorously through a 22 gauge needle.

Treat with phenol:chloroform (1:1) saturated with acetate buffer. Extract aqueous layer with 3×volume of chloroform. Add 2 vol of −20° EtOH, and ppt for 1–2 hours, but no longer.

Collect precipitate; dry briefly (<5 minutes) under vacuum. Resuspend in 7 ml of PK buffer made 0.2% with respect to SDS. If precipitate develops, heat at 65° until solution clears. Add 1.5 mg of proteinase K.

Incubate 20 minutes at 37° (if you have dried for too long, RNA will be very difficult to get into solution and vigorous pipetting will be necessary throughout the incubation).

Extract reaction with 1:1 phenol:chloroform (made 0.1% in 8-OH quinoline, 0.2% β-ME, saturate with 100 mM Tris, pH 8.5 or PK buffer pH 7.7), 2×with chloroform, ppt by addition of 1/10 volume of 3.2M Tris, pH 7.5 and 2 vol. of EtOH. Poly A$^+$ RNA may then be isolated from the RNA mixture by well-known hybridization methods utilizing matrix-immobilized oligo (dT).

EXAMPLE 2 cDNA Cloning Procedure

1. First Strand Synthesis a. The following reagents and compositions are combined together and incubated on ice for 5 minutes:

| Reagent | Volume | Final Concentration |
| --- | --- | --- |
| ~5 µg poly A+ RNA, plus water | to 10.5 µl | |
| 5X reverse transcriptase buffer | 10 µl | 1X |
| 0.5M DTT | 1 µl | 10 mM |
| RNasin (24 U/µl) | 2 µl | ~1U/µl |
| 5X dNTPs | 10 µl | 1X |
| oligo dT (250 µg/ml) | 5 µl | 25 µg/ml | b. Next, the following three reagents are added to (a) and the mixture is incubated at 37° C. for 60 minutes:

| | | |
| --- | --- | --- |
| actinomycin D (600 µg/ml) | 4 µl | ~50 µg/ml |
| $^{32}$P-gammadCTP (3200 Ci/mmol) | 2.5 µl | — |
| MMLV-reverse transcriptase | 5 µl | 200 U/µg RNA |
| (BRL-200 U/µl) | 50 µl | (total a + b) | c. The following reagents are added to (b) and the mixture is incubated at 37° C. for 30 minutes:

| | |
| --- | --- |
| RNasin (24 U/µl) | 1 µl |
| MMLV-reverse transcriptase (BRL-200 U/µl) | 3 µl | d. Take aliquots for analysis:

1 µl at time 0 for TCA

1 µl at 90 minutes for TCA 0.5 µl at 90 minutes for gel e. The reaction is stopped after 30 minutes adding 2 µl of 0.5M EDTA and performing one phenol/chloroform extraction, followed by one chloroform extraction. Then 10 µl of 10M NH$_4$OAc plus two volumes of ethanol are added to precipitate the first strand.

f. To analyze the synthesis, 0.5 µl of the reaction are run on a 1.5% agarose mini-gel, the gel is photographed, dried, and placed under film (generally an overnight exposure with an intensifying screen is adequate).

g. Calculate the mass of cDNA from the percent incorporation of label above background. 1 µg ss cDNA=1.4% incorporation.

2. Second Strand Synthesis a. The cDNA-RNA is spun down by centrifugation in a benchtop microfuge for 15 minutes. The pellet is washed in 95% ethanol and dried.

b. The following mixture is assembled and incubated at 12° C. for 60 minutes.

|  | Volume | Final Concentration |
|---|---|---|
| cDNA RNA, plus water | to 68 μl |  |
| 5X 2nd strand buffer | 20 μl | 1X |
| 10 mM β-NAD | 1.5 μl | 0.15 mM |
| 4 mM dNTPs | 5 μl | 200 μM/ml |
| DNA polymerase I (10 U/μl) | 2.5 μl | 250 U/ml |
| E. coli DNA ligase (2 U/μl) | 2 μl | 40 U/ml |
| RNase H (2.3 U/μl) | 1 μl | 23 U/ml |
|  | 100 μl |  | c. To this mix is added the following, and incubation continues at 22° C. for 60 minutes:

| DNA polymerase I (10 U/μl) | 1.5 μl |
|---|---|
| E. coli DNA ligase (2 U/μl) | 1.5 μl | d. The reaction is stopped after 60 minutes by adding 4 μl of 0.5M EDTA and performing one phenol/chloroform extraction and one chloroform extraction.

e. The aqueous phase is run over a G-50 column in a short Pasteur pipet and 100 μl fractions are collected. The 500 μls containing the cDNA is collected and pooled, and butanol extracted doom to a volume of ~50 μl . The cDNA is precipitated by adding 10 μl of 10M NH$_4$OAc plus two volumes of ethanol.

3. T4 Polymerase Reaction a. The cDNA is spun down in a microfuge for 15 minutes. A 95% ethanol wash is performed and the cDNA pellet is dried. The dry pellet is counted in a scintillation counter. Assume 100% efficiency of the 2nd strand reaction, and calculate mass of double-stranded cDNA from the first strand calculation.

b. To the cDNA is added the following, and the mixture is incubated at 37° C. for 20 minutes.

| cDNA | + |
|---|---|
| 10X T4 buffer | 5 μl |
| H$_2$O | 40.75 μl |
| 4 mM dNTPs | 1.25 μl |
| 0.1 mM DTT | 2.5 μl |
| T4 polymerase (10 U/μl) | 0.5 μl |
|  | 50 μl | c. Aliquots are taken:
0.5 μl for gel at time 0
0.5 μl for gel at 20 minutes d. The reaction is stopped after 20 minutes by adding 2 μl of 0.5M EDTA, followed by a phenol/chloroform extraction and a chloroform extraction.

e. The aqueous phase is run over a G-50 column in a short Pasteur pipet and 100 μl fractions are collected. The 500 μls containing the cDNA is collected and pooled, and butanol extracted down to a volume of ~50 μl. The cDNA is precipitated by adding 10 μl of 10M NH$_4$OAc plus two volumes of ethanol.

f. The 0.5 μl samples taken at time 0 and 20 minutes are run on a 1.5% agarose mini-gel, which is subsequently photographed, dried, and placed under film.

4. Addition of EcoRI Adapters (for Insertion into Lambda gt11)

a. Oligos are synthesized having the following sequences:
20 mer: 5'-CCATGGTACCTTCGTTGACG-3'
24 mer: 3'-GGTACCATGGAAGCAACTGCTTAA-5' b. The 20 mer is phosphorylated by combining the following reagents and incubated at 37° C. for 15 minutes.:

| 225 pmoles 20 mer | + |
|---|---|
| water | 6.8 μl |
| 10X kinase buffer | 1.2 μl |
| $^{32}$P-gammaATP (7000 Ci/mmole) | 1.0 μl |
| kinase (2 U/μl) | 1.0 μl |
|  | 10 μl | c. The following two reagents are added to above mixture and it is incubated at 37° C. for 30 minutes:

| 10 mM ATP | 1 μl |
|---|---|
| kinase (2 U/ml) | 1 μl |
|  | 12 μl (total b + c) | d. The enzyme is then inactivated by boiling for minutes.

e. The 24 mer is hybridized to the phosphorylated 20 mer by addition of 225 pmoles of the 24 mer (plus water to bring volume to 15 μl), and incubation at 65° C. for 5 minutes. The reaction is then allowed to slow cool to room temperature.

The adapters are now present at a concentration of 15 pmoles/μl , and are ready for cDNA-vector ligation.

f. Combine the following:

| cDNA | + |
|---|---|
| hybridized adapters (15 pmol/μl) | 50-fold molar excess over cDNA |
| water | 16 μl |
| 10x ligase butter | 2 μl |
| ligase (10 U/μl) | 2 μl |
|  | 20 μl |

5. Phosphorylation of cDNA a. The ligase is inactivated by heating the mixture to 72° C. for 15 minutes.

b. The following reagents are added to the cDNA ligation reaction and it is heated at 37° C. for 30 minutes:

| cDNA ligation reaction | 20 μl |
|---|---|
| water | 24 μl |
| 10X kinase buffer | 3 μl |
| 10 mM ATP | 1 μl |
| kinase (2 U/μl) | 2 μl |
|  | 50 μl | c. The reaction is stopped by the addition of 2 μl 0.5M EDTA, followed by one phenol/chloroform extraction and one chloroform extraction.

6. Purification and Size-Selection of cDNA a. The cDNA is run over a BIO-GEL A-50 column that has been washed with ≧5 ml of TE buffer. The column has 0.8 ml bed resin in a 0.2 cm (inner diameter)×30 cm siliconized glass tube with a glass wool plug in a yellow pipet tip at the bottom.

b. The cDNA is dried down in a speed vac to ~20 μl. 2.5 μl of gel loading dye is added and the cDNA is run over the column. The counts begin coming off after. running 200–250 μl TE buffer through the column. 5 minute fractions (~30 μl) are collected and counted in a scintillation counter. Free adapters may begin to elute off 350–400 μl after the cDNA starts to elute.

c. 0.5 μl of several of the collected fractions are run on a 1.5% agarose minigel. The gel is photographed, dried down, and placed under film.

7. Ligation of cDNA to Lambda gt11 vector a. The fractions containing cDNA are pooled, butanol extracted down to 20–30 μl, and 5 μl of 10M NH₄OAc plus two volumes of ethanol is added to precipitate the cDNA. It is spun in a microfuge for 15 minutes, and then subjected to a 95% ethanol wash and dry.

b. The pellet is counted, and the mass of cDNA is calculated relative to the mass after the second strand synthesis.

c. The cDNA is resuspended in TE (~0.10 pmol/μl).

d. The ligation reaction contains the following, which is incubated at 14°–16° C. overnight:

| (use 1 μg of lambda gt11 vector = 0.035 pmol vector) | |
|---|---|
| lambda gt11 (1 μg/μl) | 1 μl |
| cDNA insert | (2–4 fold molar excess of cDNA over vector) |
| water | to 3 μl |
| 5X ligase buffer | 1 μl |
| ligase (10 U/μl) | 1 μl |
| | 5 μl |

8. Packaging

The vector is packaged using the Gigapack in vitro packaging kit supplied by Strategene, and following the instructions contained therein.

| REAGENTS | |
|---|---|
| 5x RT buffer | |
| 250 mM Tris, pH 7.4 | 250 μl of 1M |
| 375 mM KCl | 375 μl of 1M |
| 15 mM MgCl₂ | 75 μl of 0.2M |
| H₂O | 300 μl |
| | 1000 μl |
| 5X dNTPs | |
| 5 mM dATP | 14.1 μl |
| 3 mM dCTP | 9.1 μl |
| 5 mM dGTP | 13.6 μl |
| 5 mM dTTP | 13.3 μl |
| | 50 μl |
| 5X 2nd Strand Buffer | |
| 100 mM Tris, pH 7.5 | 100 μl of 1M |
| 500 mM KCl | 500 μl of 1M |
| 50 mM (NH₄)₂SO₄ | 50 μl of 1M |
| 25 mM MgCl₂ | 125 μl of 0.2M |
| 250 μg/ml BSA | 5 μl of 50 mg/ml |
| water | 220 μl |
| | 1000 μl |
| 10X T4 buffer | |
| 670 mM Tris, pH 8.0 | 670 μl of 1M |
| 167 mM (NH₄)₂SO₄ | 167 μl of 1M |
| 67 mM MgCl₂ | 67 μl of 1M |
| H₂O | 96 μl |
| | 1000 μl |

EXAMPLE 3

Screening cDNA Library with Antibody

Plate lambda gt11 library on Y1090 in LB agar and 50 μg/ml ampicillin. Grow overnight in 15 ml of LB, 0.2% maltose and 50 μg/ml ampicillin. Pellet the cells and resuspend in 3 ml of 10 mM MgSO₄. Plate four plates at 250,000 plaques/plate using 25 μl of phage (10,000/μl) and 300 μl of said 3 ml solution of cells in 10 ml soft agar containing 50 μg/ml ampicillin.

Grow at 42° C. for 2.5 hours and overlay IPTG-treated filters which were soaked in 10 mM IPTG (Boehringer Mannheim Biochemicals, Indianapolis, Ind.). Dry filters until just moist, lay them in the plates and incubate overnight at 37° C.

Orient the plates and spot 0.5 μl of purified DHP receptor on one plate as a positive control. Wash the filters for 10 min at room temperature TBS (50 mM TRIS, 150 mM NaCl, pH 8.0). Wash filters in TBS, 20% FCS (filtered) for 30 min at room temp.

Incubate the filters for 2 hours in TBS, 20% FCS, anti-DHS-receptor antibody (monoclonal or polyclonal). Wash for 10 min in TBS. Transfer filters to new plates and wash for 1 min in TBS, 0.1% NP40. Wash for 10 min in TBS and transfer to new plates.

Incubate for at least 1 hour with TBS, 20% FCS containing an appropriate second antiboby (e.g. HRP-Protein A; or HRP-goat anti-mouse IgG).

Wash filters as described above for the first antibody.

Develop the positive clones using about 40 ml/plate of 4-chloro-1-naphthol reagent which is made by dissolving 60 mg of said developer in 20 ml of ice cold MeOH and mixing 4-chloro-1-naphthol (Aldrich Chemical Company, Milwaukee, Wis.) into 100 ml of TBS containing 60 μl of 30% H₂O₂.

EXAMPLE 4

An Human Neuronal Calcium Channel (Alpha)₂-Subunit- Encoding cDNA

Because of the indications, mentioned supra, that human calcium channel (alpha)₂-subunit genes had diverged somewhat from rabbit calcium channel (alpha)₂-subunit genes, human (alpha)₂-subunit- encoding fragments were isolated to use as probes to screen human brain cDNA libraries under high stringency conditions.

Thus, an EcoRI-digested human genomic Southern blot was probed under both low and high stringency conditions with a fragment of rabbit (alpha)₂-subunit-encoding cDNA (the fragment from nucleotide 43 to nucleotide 272 indicated in a FIGS. 2a–2f). Under low stringency conditions, two genomic fragments were identified, of 3.0 kbp and 3.5 kbp in size. Under high stringency conditions, only the 3.5 kbp fragment maintained a stable hybrid. These two fragments were cloned into lambda-gt11. The 3.5 kbp fragment includes a small PstI-XbaI fragment, of about 300 bp, which includes an 82 bp exon with 96.4% homology to nucleotides 102 to 183 of the sequence in FIGS. 2a–2f. This exon is preceded by the dinucleotide AG (splice donor) and followed by the dinucleotide GT (splice acceptor), as understood in the art. The 3.0 kbp fragment includes an XbaI-BglII fragment, of about 585 bp, which includes 104 bp of an exon (which includes the BglII site at its downstream end) which, in the 104 bp, has 93.3% homology to nucleotides 184 to 287 of the sequence in FIGS. 2a–2f. Both the 300 bp, PstI-XbaI fragment and the 585 bp, XbaI-BglII fragments were used to probe duplicate lifts of a human basal ganglia cDNA library in lambda-gt11 (the library having been obtained from the American Type Culture Collection, Rockville, Md., USA, and containing about 10⁶ independent recombinants with an average insert size of 800–1000 bp). Three positive clones were identified which hybridized to both probes under high stringency conditions, one with an insert size of about 1150 bp, another with an insert size of about 790 bp, and the third with an insert size of about 670 bp. The 1150 bp insert in the one clone extended into the coding region from about nucleotide 200 in the coding region and was found to have a sequence more than 90% homologous to that of the corresponding segment of the cDNA whose sequence is presented in FIGS. 2a–2f. Using the lambda genome with the 1150 bp insert as probe, an human brain stem cDNA library (also purchased from the American Type Culture Collection, and having about $4 \times 10^6$ independent recombinants with an average insert size of 800–1000 bp) was probed under high stringency conditions. In this probing, four positive clones were identified, with inserts of about 950 bp, 1120 bp, 3000 bp and 2500 bp. Most of the 1120 bp insert overlapped the 1150 bp insert of the DNA used as probe but extended somewhat upstream from the upstream end of the 1150 bp insert. The 2500 bp insert extended downstream from about 650 bp from the 5'-end of the 1120 bp insert. The DNA with the 2500 bp insert was used to again probe the brain stem library, and a clone with a 2750 bp insert was found. The 2750 bp insert was found by restriction analysis and sequencing to extend in the 3'-direction beyond the translational stop signal of a reading frame that was found to begin in the 1120 bp insert described above. The 2750 bp insert and 1120 bp insert have a PvuII site in common and have been ligated using the PvuII site to provide a cDNA that encodes a human neuronal calcium channel $(alpha)_2$-subunit. The 5'-1560 bp of this cDNA have been sequenced and, as illustrated in FIGS. 3a–3d, found to be 91.2% homologous with the corresponding 1575 bp segment indicated in FIGS. 2a–2f.

The human $(alpha)_2$-subunit-encoding cDNA will be subcloned into the mammalian expression vector pSV2DHFR, which is available in the art, for expression in mammalian tissue culture cells.

We obtained the human neuroblastoma cell line IMR32 from the American Type Culture Collection (accession no. CCL127). A northern blot analysis was carried out on poly $A^+$ RNA from this cell line using the full-length human $(alpha)_2$-subunit-encoding cDNA. Under low stringency washing, a single 8.2 kb fragment was found. The rabbit skeletal muscle $(alpha)_2$-encoding messenger RNA also had a size similar to 8.2 kb. While the invention has been described herein with some specificity, the ordinarily skilled in the art will recognize numerous variations and modifications, in what is described, that are within the spirit of the invention. Such variations and modifications are within the scope of the invention as described in the claims herein.

Various features of the invention are also described in the following.

---

What is claimed is:

1. An isolated single-stranded nucleic acid having a sequence which is:
   (a) a fragment of the sequence shown in SEQ ID NO: 2 comprising at least 12 contiguous bases of the sequence from nucleotides 282 to 3627 of SEQ ID NO: 2, or
   (b) the complement of the sequence of (a).

2. An isolated single-stranded nucleic acid having a sequence which is:
   (a) a fragment of the sequence shown in SEQ ID NO: 3 comprising at least 12 contiguous bases of SEQ ID NO: 3, or
   (b) the complement of the sequence of (a).

3. An isolated single-stranded nucleic acid comprising a sequence which is:
   (a) a fragment of the sequence shown in SEQ ID NO: 2 comprising at least 30 contiguous bases of the sequence from nucleotides 71 to 3802 of SEQ ID NO: 2, or
   (b) the complement of the sequence of (a).

4. An isolated single-stranded nucleic acid comprising a sequence which is:
   (a) a fragment of the sequence shown in SEQ ID NO: 3 comprising at least 30 contiguous bases of SEQ ID NO: 3, or
   (b) the complement of the sequence of (a).

5. A nucleic acid of claim 1 that is detectably labeled.
6. A nucleic acid of claim 2 that is detectably labeled.
7. A nucleic acid of claim 3 that is detectably labeled.
8. A nucleic acid of claim 4 that is detectably labeled.
9. A nucleic acid of claim 5 that is labeled with $^{32}P$.
10. A nucleic acid of claim 6 that is labeled with $^{32}P$.
11. A nucleic acid of claim 7 that is labeled with $^{32}P$.
12. A nucleic acid of claim 8 that is labeled with $^{32}P$.
13. A method for identifying a nucleic acid encoding all or part of a calcium channel $\alpha_2$ subunit, comprising the steps of
   contacting a sample of DNA or RNA with the nucleic acid of claim 1, and
   identifying DNA or RNA present in the sample which hybridizes under conditions of high or low stringency with the nucleic acid.
14. A method for identifying a nucleic acid encoding all or part of a calcium channel $\alpha_2$ subunit, comprising the steps of
   contacting a sample of DNA or RNA with the nucleic acid of claim 2, and
   identifying DNA or RNA present in the sample which hybridizes under conditions of high or low stringency with the nucleic acid.
15. A method for identifying a nucleic acid encoding all or part of a calcium channel $\alpha_2$ subunit, comprising the steps of contacting a sample of DNA or RNA with the nucleic acid of claim 3, and identifying DNA or RNA present in the sample which hybridizes under conditions of high or low stringency with the nucleic acid.

16. A method for identifying a nucleic acid encoding all or part of a calcium channel $\alpha_2$ subunit, comprising the steps of contacting a sample of DNA or RNA with the nucleic acid of claim 4, and identifying DNA or RNA present in the sample which hybridizes under conditions of high or low stringency with the nucleic acid.

17. An isolated nucleic acid molecule comprising at least 30 contiguous base pairs of the sequence set forth in SEQ ID No. 2 between nucleotides 71–3802.

18. An isolated nucleic acid molecule comprising at least 30 contiguous base pairs of the sequence set forth in SEQ ID No. 3.

* * * * *

UNITED STATES PATENT AND TRADEMARK OFFICE
CERTIFICATE OF CORRECTION

PATENT NO. : 5,686,241
DATED : November 11, 1997
INVENTOR(S) : Steven B. Ellis, et al It is certified that error appears in the above-identified patent and that said Letters Patent is hereby corrected as shown below:

On the title page, item [62]
IN THE RELATED U.S. APPLICATIONS:
  at lines 1-5, "Division of Ser. No. 914,231, Jul. 13, 1992, Pat. No. 5,407,820 which is a continuation of Ser. No. 603,751, filed as PCT/US89/01408, Apr. 4, 1989, abandoned, which is a continuation-in-part of Ser. No. 176,899, Apr. 4, 1988, abandoned." should read
  —Division of Ser. No. 914,231, Jul. 13, 1992, Pat. No. 5,407,820 which is a continuation of Ser. No. 603,751, filed Nov. 8, 1990, abandoned, which is a continuation-in-part of Ser. No. 176,899, Apr. 4, 1988, abandoned, U.S. application Ser. No. 07/603,751 was filed as International PCT application PCT/US89/01408, Apr. 4, 1989.— column 2, lines 33 and 37, "cDNA's" should read -- cDNAs--;
  column 2, line 34, "DNA's" should read -- cDNAs --;
  column 3, line 3, "As" should read —is—;
  column 3, line 28, "convened" should read —converted—;
  column 5, line 64, "agohist" should read —agonist—;
  column 7, line 60, "en" should read —an—;
  column 8, line 21, "Piscathaway" should read —Piscataway—;
  column 8, line 67, column 9, line 39, and column 10, line 12, "Ash", each occurrence, should read —Asn—;
  column 9, line 1, "Set" should read —Ser—;
  column 9, lines 31 and 32, "Mr" should read —$M_r$—;
  column 10, line 46, column 15, line 7, and column 17, line 11, each occurrence, "eDNA" should read —cDNA—;
  column 11, line 30, "0.1" should read —0.1M—;

UNITED STATES PATENT AND TRADEMARK OFFICE
CERTIFICATE OF CORRECTION

PATENT NO. : 5,686,241

DATED : November 11, 1997

INVENTOR(S) : Steven B. Ellis, et al

It is certified that error appears in the above-identified patent and that said Letters Patent is hereby corrected as shown below:

column 11, line 33, "3.2" should read —3.2M—;
column 14, line 67, "elude" should read —elute—;

column 16, line 8, "Mannhelm" should read —Mannheim—.

Signed and Sealed this

Thirteenth Day of October 1998

*Attest:*

BRUCE LEHMAN

*Attesting Officer*  Commissioner of Patents and Trademarks

UNITED STATES PATENT AND TRADEMARK OFFICE
CERTIFICATE OF CORRECTION

Page 1 of 2

PATENT NO. : 5,686,241
DATED : November 11, 1997
INVENTOR(S) : Ellis, et. al.

It is certified that error appears in the above-identified patent and that said Letters Patent is hereby corrected as shown below:

At column 8, line 54, please insert the following pages which were omitted —As pertains to the (alpha)$_2$-subunit, in an initial screen with the guinea pig (alpha)$_2$-specific polyclonal anti-sera, three cDNA clones were isolated and shown to be related to each other but not any (alpha)$_1$ cDNA sequences by cross-hybridization. Two of these cDNA clones were used to rescreen the lambda gt11 cDNA library to isolate overlapping cDNA clones. The cDNA clones were analyzed to establish the coding DNA sequence of the (alpha)$_2$-subunit of the calcium channel and a restriction map was made. Approximately 7,850 nucleotides of (alpha)$_2$ cDNA was cloned, which is consistent with an ~8,000 nucleotide (alpha)$_2$ mRNA.

An oligo-dT-primed expression cDNA library was constructed in lambda gt11, using young adult rabbit back skeletal muscle poly (A+) RNA as described for the (alpha)$_1$-subunit. Double-stranded cDNA fragments > 1500 bp were ligated in lamda gt11 and a primary plating of $1 \times 10^6$ recombinants was screened with guinea pig anti-160 Kd (alpha)$_2$ polyclonal anti-sera. Three positive plaques were visualized by binding HRP-Protein A, followed by color development with 4-chloro-1-napthol. Two clones, (2.5 Kb and 3.6 Kb) overlapped to encode 4.75 Kb of an ~8 Kb transcript identified by Northern analysis. (alpha)$_2$ cDNA clones extending in the 5' and 3' direction (oriented by DNA sequencing and identification of a long open reading frame) wre isolated by rescreening the same lambda gt11 cDNA library with the (EcoRI) - HindIII fragment of one clone (nts 43-272, 5' proximal; EcoRI site from adapter) or the EcoRI - (EcoRI) fragment of a second clone (~1.0 Kb in the 3' untranslated region). A total of 14 clones were isolated, seven from each end, of which an overlapping pair of clones (one extending ~2,750 nts 3' and the other extending 350 nts 5') encoded ~7,850 nts of the (alpha)$_2$ transcript; 308 nts of 5' untranslated sequence, 3,318 nts of coding sequence, and ~4,224 of 3' untranslated sequence. Only 176 nts of 3' untranslated sequence was confirmed in both directions and is reported.

UNITED STATES PATENT AND TRADEMARK OFFICE
CERTIFICATE OF CORRECTION

PATENT NO. : 5,686,241
DATED : November 11, 1997
INVENTOR(S) : Ellis, et. al.

It is certified that error appears in the above-identified patent and that said Letters Patent is hereby corrected as shown below:

FIGS. 2a-2f represent the 3,802 nucleotides of the cDNA sequence encoding the (alpha)$_2$-subunit and its precursor, including 308 nucleotides of 5' untranslated sequence, a 3,318 open reading frame, and 176 nucleotides of 3' untranslated sequence.—

Signed and Sealed this

Eleventh Day of April, 2000

Q. TODD DICKINSON

*Attest:*

*Attesting Officer*            *Director of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 5975 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: Coding Sequence
( B ) LOCATION: 79...5700
( D ) OTHER INFORMATION:

( x i ) SEQUENCE DESCRIPTION: SEQ ID NO:1:

```
GCGGGGAACA  CTGGGGACGC  AGGGAAGAGA  GGGCCGCGGG  GTGGGGGAGC  AGCAGGAAGC       60

GCCGTGGCCA  GGGAAGCC   ATG  GAG  CCA  TCC  TCA  CCC  CAG  GAT  GAG  GGC  CTG    111
                      Met  Glu  Pro  Ser  Ser  Pro  Gln  Asp  Glu  Gly  Leu
                       1         5                              10

AGG  AAG  AAA  CAG  CCC  AAG  AAG  CCC  CTG  CCC  GAG  GTC  CTG  CCC  AGG  CCG  159
Arg  Lys  Lys  Gln  Pro  Lys  Lys  Pro  Leu  Pro  Glu  Val  Leu  Pro  Arg  Pro
              15                   20                        25

CCG  CGG  GCT  CTG  TTC  TGC  CTG  ACC  CTG  CAG  AAC  CCG  CTG  AGG  AAG  GCG  207
Pro  Arg  Ala  Leu  Phe  Cys  Leu  Thr  Leu  Gln  Asn  Pro  Leu  Arg  Lys  Ala
          30                   35                   40

TGC  ATC  AGC  ATC  GTG  GAA  TGG  AAA  CCC  TTC  GAG  ACC  ATC  ATC  CTG  CTC  255
Cys  Ile  Ser  Ile  Val  Glu  Trp  Lys  Pro  Phe  Glu  Thr  Ile  Ile  Leu  Leu
         45                   50                        55

ACC  ATC  TTT  GCC  AAC  TGT  GTG  GCC  CTG  GCC  GTG  TAC  CTG  CCC  ATG  CCC  303
Thr  Ile  Phe  Ala  Asn  Cys  Val  Ala  Leu  Ala  Val  Tyr  Leu  Pro  Met  Pro
```

-continued

| | | | | | | | | | | | | | | | | |
|---|---|---|---|---|---|---|---|---|---|---|---|---|---|---|---|---|
| 60 | | | | | 65 | | | | | 70 | | | | | 75 | |
| GAG | GAT | GAC | AAC | AAC | TCC | CTG | AAC | CTG | GGC | CTG | GAG | AAG | CTG | GAG | TAC | 351 |
| Glu | Asp | Asp | Asn | Asn 80 | Ser | Leu | Asn | Leu 85 | Gly | Leu | Glu | Lys | Leu 90 | Glu | Tyr | |
| TTC | TTC | CTC | ACC | GTC | TTC | TCC | ATC | GAA | GCC | GCC | ATG | AAG | ATC | ATC | GCC | 399 |
| Phe | Phe | Leu | Thr 95 | Val | Phe | Ser | Ile | Glu 100 | Ala | Ala | Met | Lys | Ile 105 | Ile | Ala | |
| TAC | GGC | TTC | CTG | TTC | CAC | CAG | GAC | GCC | TAC | CTG | CGC | AGC | GGC | TGG | AAC | 447 |
| Tyr | Gly | Phe 110 | Leu | Phe | His | Gln | Asp 115 | Ala | Tyr | Leu | Arg | Ser 120 | Gly | Trp | Asn | |
| GTG | CTG | GAC | TTC | ATC | ATC | GTC | TTC | CTG | GGG | GTC | TTC | ACG | GCG | ATT | CTG | 495 |
| Val | Leu 125 | Asp | Phe | Ile | Ile 130 | Val | Phe | Leu | Gly | Val 135 | Phe | Thr | Ala | Ile | Leu | |
| GAA | CAG | GTC | AAC | GTC | ATC | CAG | AGC | AAC | ACG | GCC | CCG | ATG | AGC | AGC | AAA | 543 |
| Glu 140 | Gln | Val | Asn | Val 145 | Ile | Gln | Ser | Asn | Thr 150 | Ala | Pro | Met | Ser | Ser 155 | Lys | |
| GGA | GCC | GGC | CTG | GAC | GTC | AAG | GCC | CTG | AGG | GCC | TTC | CGT | GTG | CTC | AGA | 591 |
| Gly | Ala | Gly | Leu | Asp 160 | Val | Lys | Ala | Leu | Arg 165 | Ala | Phe | Arg | Val | Leu 170 | Arg | |
| CCC | CTC | CGG | CTG | GTG | TCG | GGG | GTG | CCT | AGT | TTG | CAG | GTG | GTC | CTC | AAC | 639 |
| Pro | Leu | Arg | Leu 175 | Val | Ser | Gly | Val | Pro 180 | Ser | Leu | Gln | Val | Val 185 | Leu | Asn | |
| TCC | ATC | TTC | AAG | GCC | ATG | CTC | CCC | CTG | TTC | CAC | ATC | GCC | CTG | CTC | GTC | 687 |
| Ser | Ile | Phe 190 | Lys | Ala | Met | Leu | Pro 195 | Leu | Phe | His | Ile | Ala 200 | Leu | Leu | Val | |
| CTC | TTC | ATG | GTC | ATC | ATC | TAC | GCC | ATC | ATC | GGG | CTG | GAG | CTC | TTC | AAG | 735 |
| Leu | Phe 205 | Met | Val | Ile | Ile | Tyr 210 | Ala | Ile | Ile | Gly | Leu 215 | Glu | Leu | Phe | Lys | |
| GGC | AAG | ATG | CAC | AAG | ACC | TGC | TAC | TAC | ATC | GGG | ACA | GAC | ATC | GTG | GCC | 783 |
| Gly 220 | Lys | Met | His | Lys | Thr 225 | Cys | Tyr | Tyr | Ile | Gly 230 | Thr | Asp | Ile | Val | Ala 235 | |
| ACA | GTG | GAG | AAT | GAG | AAG | CCC | TCG | CCC | TGC | GCT | AGG | ACG | GGC | TCG | GGG | 831 |
| Thr | Val | Glu | Asn | Glu 240 | Lys | Pro | Ser | Pro | Cys 245 | Ala | Arg | Thr | Gly | Ser 250 | Gly | |
| CGC | CCC | TGC | ACC | ATC | AAC | GGC | AGC | GAG | TGC | CGG | GGC | GGC | TGG | CCG | GGG | 879 |
| Arg | Pro | Cys | Thr 255 | Ile | Asn | Gly | Ser | Glu 260 | Cys | Arg | Gly | Gly | Trp 265 | Pro | Gly | |
| CCC | AAC | CAC | GGC | ATC | ACG | CAC | TTC | GAC | AAC | TTC | GGC | TTC | TCC | ATG | CTC | 927 |
| Pro | Asn | His 270 | Gly | Ile | Thr | His | Phe 275 | Asp | Asn | Phe | Gly | Phe 280 | Ser | Met | Leu | |
| ACC | GTG | TAC | CAG | TGC | ATC | ACC | ATG | GAG | GGC | TGG | ACA | GAT | GTC | CTC | TAC | 975 |
| Thr | Val | Tyr 285 | Gln | Cys | Ile | Thr | Met 290 | Glu | Gly | Trp | Thr | Asp 295 | Val | Leu | Tyr | |
| TGG | GTC | AAC | GAT | GCC | ATC | GGG | AAC | GAG | TGG | CCC | TGG | ATC | TAC | TTT | GTC | 1023 |
| Trp | Val 300 | Asn | Asp | Ala | Ile | Gly 305 | Asn | Glu | Trp | Pro | Trp 310 | Ile | Tyr | Phe | Val 315 | |
| ACT | CTC | ATC | CTG | CTG | GGG | TCC | TTC | TTC | ATC | CTC | AAC | CTG | GTG | CTG | GGC | 1071 |
| Thr | Leu | Ile | Leu | Leu 320 | Gly | Ser | Phe | Phe | Ile 325 | Leu | Asn | Leu | Val | Leu 330 | Gly | |
| GTC | CTG | AGT | GGG | GAA | TTC | ACC | AAG | GAG | CGG | GAG | AAG | GCC | AAG | TCC | AGG | 1119 |
| Val | Leu | Ser | Gly 335 | Glu | Phe | Thr | Lys | Glu 340 | Arg | Glu | Lys | Ala | Lys 345 | Ser | Arg | |
| GGA | ACC | TTC | CAG | AAG | CTG | CGG | GAG | AAG | CAG | CAG | CTG | GAG | GAG | GAC | CTT | 1167 |
| Gly | Thr | Phe 350 | Gln | Lys | Leu | Arg | Glu 355 | Lys | Gln | Gln | Leu | Glu 360 | Glu | Asp | Leu | |
| CGG | GGC | TAC | ATG | AGC | TGG | ATC | ACG | CAG | GGC | GAG | GTC | ATG | GAC | GTG | GAG | 1215 |
| Arg | Gly | Tyr 365 | Met | Ser | Trp | Ile | Thr 370 | Gln | Gly | Glu | Val | Met 375 | Asp | Val | Glu | |
| GAC | CTG | AGA | GAA | GGA | AAG | CTG | TCC | TTG | GAA | GAG | GGA | GGC | TCC | GAC | ACG | 1263 |
| Asp | Leu | Arg | Glu | Gly | Lys | Leu | Ser | Leu | Glu | Glu | Gly | Gly | Ser | Asp | Thr | |

|     |     |     |     |     | 380 |     |     |     |     | 385 |     |     |     |     | 390 |     |     |     |     | 395 |      |
|-----|-----|-----|-----|-----|-----|-----|-----|-----|-----|-----|-----|-----|-----|-----|-----|-----|-----|-----|-----|-----|------|
| GAA | AGC | CTG | TAC | GAA | ATC | GAG | GGC | TTG | AAC | AAA | ATC | ATC | CAG | TTC | ATC | | | | | | 1311 |
| Glu | Ser | Leu | Tyr | Glu | Ile | Glu | Gly | Leu | Asn | Lys | Ile | Ile | Gln | Phe | Ile | | | | | | |
|     |     |     |     | 400 |     |     |     | 405 |     |     |     |     | 410 |     |     | | | | | | |

| CGA | CAC | TGG | AGG | CAG | TGG | AAC | CGT | GTC | TTT | CGC | TGG | AAG | TGC | CAT | GAC | 1359 |
|-----|-----|-----|-----|-----|-----|-----|-----|-----|-----|-----|-----|-----|-----|-----|-----|------|
| Arg | His | Trp | Arg | Gln | Trp | Asn | Arg | Val | Phe | Arg | Trp | Lys | Cys | His | Asp | |
|     |     |     | 415 |     |     |     |     | 420 |     |     |     |     | 425 |     |     | |

| CTG | GTG | AAG | TCG | AGA | GTC | TTC | TAC | TGG | CTG | GTC | ATC | CTG | ATC | GTG | GCC | 1407 |
| Leu | Val | Lys | Ser | Arg | Val | Phe | Tyr | Trp | Leu | Val | Ile | Leu | Ile | Val | Ala | |
|     |     | 430 |     |     |     |     | 435 |     |     |     |     | 440 |     |     |     | |

| CTC | AAC | ACC | CTG | TCC | ATC | GCC | TCG | GAG | CAC | CAC | AAC | CAG | CCG | CTC | TGG | 1455 |
| Leu | Asn | Thr | Leu | Ser | Ile | Ala | Ser | Glu | His | His | Asn | Gln | Pro | Leu | Trp | |
|     | 445 |     |     |     |     | 450 |     |     |     |     | 455 |     |     |     |     | |

| CTG | ACC | CAC | TTG | CAA | GAC | ATC | GCC | AAT | CGA | GTG | CTG | CTG | TCA | CTC | TTC | 1503 |
| Leu | Thr | His | Leu | Gln | Asp | Ile | Ala | Asn | Arg | Val | Leu | Leu | Ser | Leu | Phe | |
| 460 |     |     |     |     | 465 |     |     |     |     | 470 |     |     |     |     | 475 | |

| ACC | ATC | GAG | ATG | CTG | CTG | AAG | ATG | TAC | GGG | CTG | GGC | CTG | CGC | CAG | TAC | 1551 |
| Thr | Ile | Glu | Met | Leu | Leu | Lys | Met | Tyr | Gly | Leu | Gly | Leu | Arg | Gln | Tyr | |
|     |     |     |     | 480 |     |     |     |     | 485 |     |     |     |     | 490 |     | |

| TTC | ATG | TCC | ATC | TTC | AAC | CGC | TTC | GAC | TGC | TTC | GTG | GTG | TGC | AGC | GGC | 1599 |
| Phe | Met | Ser | Ile | Phe | Asn | Arg | Phe | Asp | Cys | Phe | Val | Val | Cys | Ser | Gly | |
|     |     |     | 495 |     |     |     |     | 500 |     |     |     |     | 505 |     |     | |

| ATC | CTG | GAG | CTG | CTG | CTG | GTG | GAG | TCG | GGC | GCC | ATG | ACG | CCG | CTG | GGC | 1647 |
| Ile | Leu | Glu | Leu | Leu | Leu | Val | Glu | Ser | Gly | Ala | Met | Thr | Pro | Leu | Gly | |
|     |     | 510 |     |     |     |     | 515 |     |     |     |     | 520 |     |     |     | |

| ATC | TCC | GTG | TTG | CGC | TGC | ATC | CGC | CTC | CTG | AGG | CTC | TTC | AAG | ATC | ACC | 1695 |
| Ile | Ser | Val | Leu | Arg | Cys | Ile | Arg | Leu | Leu | Arg | Leu | Phe | Lys | Ile | Thr | |
|     | 525 |     |     |     |     | 530 |     |     |     |     | 535 |     |     |     |     | |

| AAG | TAC | TGG | ACG | TCG | CTC | AGC | AAC | CTG | GTG | GCC | TCC | CTG | CTC | AAC | TCC | 1743 |
| Lys | Tyr | Trp | Thr | Ser | Leu | Ser | Asn | Leu | Val | Ala | Ser | Leu | Leu | Asn | Ser | |
| 540 |     |     |     |     | 545 |     |     |     |     | 550 |     |     |     |     | 555 | |

| ATC | CGC | TCC | ATC | GCC | TCG | CTG | CTG | CTG | CTC | TTC | CTC | TTC | ATC | ATC | | 1791 |
| Ile | Arg | Ser | Ile | Ala | Ser | Leu | Leu | Leu | Leu | Phe | Leu | Phe | Ile | Ile | | |
|     |     |     |     | 560 |     |     |     |     | 565 |     |     |     |     | 570 | | |

| ATC | TTC | GCC | CTG | CTG | GGC | ATG | CAG | CTC | TTC | GGG | GGG | CGG | TAC | GAC | TTC | 1839 |
| Ile | Phe | Ala | Leu | Leu | Gly | Met | Gln | Leu | Phe | Gly | Gly | Arg | Tyr | Asp | Phe | |
|     |     |     | 575 |     |     |     |     | 580 |     |     |     |     | 585 |     |     | |

| GAG | GAC | ACG | GAA | GTG | CGA | CGC | AGC | AAC | TTC | GAC | AAC | TTC | CCC | CAG | GCC | 1887 |
| Glu | Asp | Thr | Glu | Val | Arg | Arg | Ser | Asn | Phe | Asp | Asn | Phe | Pro | Gln | Ala | |
|     |     | 590 |     |     |     |     | 595 |     |     |     |     | 600 |     |     |     | |

| CTC | ATC | AGC | GTC | TTC | CAG | GTG | CTG | ACG | GGT | GAG | GAC | TGG | AAC | TCC | GTG | 1935 |
| Leu | Ile | Ser | Val | Phe | Gln | Val | Leu | Thr | Gly | Glu | Asp | Trp | Asn | Ser | Val | |
|     | 605 |     |     |     |     | 610 |     |     |     |     | 615 |     |     |     |     | |

| ATG | TAC | AAC | GGG | ATC | ATG | GCC | TAC | GGA | GGC | CCG | TCC | TAC | CCG | GGC | GTT | 1983 |
| Met | Tyr | Asn | Gly | Ile | Met | Ala | Tyr | Gly | Gly | Pro | Ser | Tyr | Pro | Gly | Val | |
| 620 |     |     |     |     | 625 |     |     |     |     | 630 |     |     |     |     | 635 | |

| CTC | GTG | TGC | ATC | TAT | TTC | ATC | ATC | CTT | TTT | GTC | TGC | GGC | AAC | TAT | ATC | 2031 |
| Leu | Val | Cys | Ile | Tyr | Phe | Ile | Ile | Leu | Phe | Val | Cys | Gly | Asn | Tyr | Ile | |
|     |     |     |     | 640 |     |     |     |     | 645 |     |     |     |     | 650 |     | |

| CTG | CTG | AAT | GTC | TTC | CTG | GCC | ATC | GCC | GTG | GAC | AAC | CTG | GCC | GAG | GCC | 2079 |
| Leu | Leu | Asn | Val | Phe | Leu | Ala | Ile | Ala | Val | Asp | Asn | Leu | Ala | Glu | Ala | |
|     |     |     | 655 |     |     |     |     | 660 |     |     |     |     | 665 |     |     | |

| GAG | AGC | CTG | ACT | TCC | GCG | CAA | AAG | GCC | AAG | GCC | GAG | GAG | AGG | AAA | CGT | 2127 |
| Glu | Ser | Leu | Thr | Ser | Ala | Gln | Lys | Ala | Lys | Ala | Glu | Glu | Arg | Lys | Arg | |
|     |     | 670 |     |     |     |     | 675 |     |     |     |     | 680 |     |     |     | |

| AGG | AAG | ATG | TCC | AGG | GGT | CTC | CCT | GAC | AAG | ACG | GAG | GAG | GAG | AAG | TCT | 2175 |
| Arg | Lys | Met | Ser | Arg | Gly | Leu | Pro | Asp | Lys | Thr | Glu | Glu | Glu | Lys | Ser | |
|     | 685 |     |     |     |     | 690 |     |     |     |     | 695 |     |     |     |     | |

| GTG | ATG | GCC | AAG | AAG | CTG | GAG | CAG | AAG | CCC | AAG | GGG | GAG | GGC | ATC | CCC | 2223 |
| Val | Met | Ala | Lys | Lys | Leu | Glu | Gln | Lys | Pro | Lys | Gly | Glu | Gly | Ile | Pro | |

-continued

| | | | | | | | | | | | | | | | | |
|---|---|---|---|---|---|---|---|---|---|---|---|---|---|---|---|---|
| | 700 | | | | 705 | | | | 710 | | | | 715 | | | |
| ACC | ACT | GCC | AAG | CTC | AAG | GTC | GAT | GAG | TTC | GAA | TCT | AAC | GTC | AAC | GAG | 2271 |
| Thr | Thr | Ala | Lys | Leu | Lys | Val | Asp | Glu | Phe | Glu | Ser | Asn | Val | Asn | Glu | |
| | | | | 720 | | | | 725 | | | | | 730 | | | |
| GTG | AAG | GAC | CCC | TAC | CCT | TCA | GCT | GAC | TTC | CCA | GGG | GAT | GAT | GAG | GAG | 2319 |
| Val | Lys | Asp | Pro | Tyr | Pro | Ser | Ala | Asp | Phe | Pro | Gly | Asp | Asp | Glu | Glu | |
| | | | 735 | | | | 740 | | | | | 745 | | | | |
| GAC | GAG | CCT | GAG | ATC | CCA | GTG | AGC | CCC | CGA | CCG | CGC | CCG | CTG | GCC | GAG | 2367 |
| Asp | Glu | Pro | Glu | Ile | Pro | Val | Ser | Pro | Arg | Pro | Arg | Pro | Leu | Ala | Glu | |
| | | 750 | | | | 755 | | | | | 760 | | | | | |
| CTG | CAG | CTC | AAA | GAG | AAG | GCA | GTG | CCC | ATC | CCG | GAA | GCC | AGC | TCC | TTC | 2415 |
| Leu | Gln | Leu | Lys | Glu | Lys | Ala | Val | Pro | Ile | Pro | Glu | Ala | Ser | Ser | Phe | |
| | 765 | | | | 770 | | | | | 775 | | | | | | |
| TTC | ATC | TTC | AGT | CCC | ACC | AAT | AAG | GTC | CGT | GTC | CTG | TGT | CAC | CGC | ATC | 2463 |
| Phe | Ile | Phe | Ser | Pro | Thr | Asn | Lys | Val | Arg | Val | Leu | Cys | His | Arg | Ile | |
| 780 | | | | | 785 | | | | | 790 | | | | | 795 | |
| GTC | AAC | GCC | ACC | TGG | TTC | ACC | AAC | TTC | ATC | CTG | CTC | TTC | ATC | CTG | CTC | 2511 |
| Val | Asn | Ala | Thr | Trp | Phe | Thr | Asn | Phe | Ile | Leu | Leu | Phe | Ile | Leu | Leu | |
| | | | | 800 | | | | | 805 | | | | | 810 | | |
| AGC | AGT | GCT | GCG | CTG | GCC | GCC | GAG | GAC | CCC | ATC | CGG | GCG | GAG | TCC | GTG | 2559 |
| Ser | Ser | Ala | Ala | Leu | Ala | Ala | Glu | Asp | Pro | Ile | Arg | Ala | Glu | Ser | Val | |
| | | | 815 | | | | | 820 | | | | | 825 | | | |
| AGG | AAT | CAG | ATC | CTT | GGA | TAT | TTT | GAT | ATT | GCC | TTC | ACC | TCT | GTC | TTC | 2607 |
| Arg | Asn | Gln | Ile | Leu | Gly | Tyr | Phe | Asp | Ile | Ala | Phe | Thr | Ser | Val | Phe | |
| | | 830 | | | | | 835 | | | | | 840 | | | | |
| ACT | GTG | GAG | ATT | GTC | CTC | AAG | ATG | ACA | ACC | TAC | GGC | GCC | TTC | CTG | CAC | 2655 |
| Thr | Val | Glu | Ile | Val | Leu | Lys | Met | Thr | Thr | Tyr | Gly | Ala | Phe | Leu | His | |
| | 845 | | | | | 850 | | | | | 855 | | | | | |
| AAG | GGC | TCC | TTC | TGC | CGC | AAC | TAC | TTC | AAC | ATC | CTG | GAC | CTG | CTG | GTG | 2703 |
| Lys | Gly | Ser | Phe | Cys | Arg | Asn | Tyr | Phe | Asn | Ile | Leu | Asp | Leu | Leu | Val | |
| 860 | | | | | 865 | | | | | 870 | | | | | 875 | |
| GTG | GCC | GTG | TCT | CTC | ATC | TCC | ATG | GGT | CTC | GAG | TCC | AGC | ACC | ATC | TCC | 2751 |
| Val | Ala | Val | Ser | Leu | Ile | Ser | Met | Gly | Leu | Glu | Ser | Ser | Thr | Ile | Ser | |
| | | | | 880 | | | | | 885 | | | | | 890 | | |
| GTG | GTA | AAG | ATC | CTG | AGA | GTG | CTA | AGG | GTG | CTC | CGG | CCC | CTG | CGA | GCC | 2799 |
| Val | Val | Lys | Ile | Leu | Arg | Val | Leu | Arg | Val | Leu | Arg | Pro | Leu | Arg | Ala | |
| | | | 895 | | | | | 900 | | | | | 905 | | | |
| ATC | AAC | AGA | GCC | AAA | GGG | TTG | AAG | CAC | GTG | GTC | CAG | TGC | GTG | TTC | GTG | 2847 |
| Ile | Asn | Arg | Ala | Lys | Gly | Leu | Lys | His | Val | Val | Gln | Cys | Val | Phe | Val | |
| | | 910 | | | | | 915 | | | | | 920 | | | | |
| GCC | ATC | CGC | ACC | ATC | GGG | AAC | ATC | GTC | CTG | GTC | ACC | ACG | CTC | CTG | CAG | 2895 |
| Ala | Ile | Arg | Thr | Ile | Gly | Asn | Ile | Val | Leu | Val | Thr | Thr | Leu | Leu | Gln | |
| | 925 | | | | | 930 | | | | | 935 | | | | | |
| TTC | ATG | TTC | GCC | TGC | ATC | GGT | GTC | CAG | CTC | TTC | AAG | GGC | AAG | TTC | TTC | 2943 |
| Phe | Met | Phe | Ala | Cys | Ile | Gly | Val | Gln | Leu | Phe | Lys | Gly | Lys | Phe | Phe | |
| 940 | | | | | 945 | | | | | 950 | | | | | 955 | |
| AGC | TGC | AAT | GAC | CTA | TCC | AAG | ATG | ACA | GAA | GAG | GAG | TGC | AGG | GGC | TAC | 2991 |
| Ser | Cys | Asn | Asp | Leu | Ser | Lys | Met | Thr | Glu | Glu | Glu | Cys | Arg | Gly | Tyr | |
| | | | | 960 | | | | | 965 | | | | | 970 | | |
| TAC | TAT | GTG | TAC | AAG | GAC | GGG | GAC | CCC | ACG | CAG | ATG | GAG | CTG | CGC | CCC | 3039 |
| Tyr | Tyr | Val | Tyr | Lys | Asp | Gly | Asp | Pro | Thr | Gln | Met | Glu | Leu | Arg | Pro | |
| | | | 975 | | | | 980 | | | | | 985 | | | | |
| CGC | CAG | TGG | ATA | CAC | AAT | GAC | TTC | CAC | TTT | GAC | AAC | GTG | CTG | TCG | GCC | 3087 |
| Arg | Gln | Trp | Ile | His | Asn | Asp | Phe | His | Phe | Asp | Asn | Val | Leu | Ser | Ala | |
| | | 990 | | | | 995 | | | | | 1000 | | | | | |
| ATG | ATG | TCG | CTC | TTC | ACG | GTG | TCC | ACC | TTC | GAG | GGA | TGG | CCC | CAG | CTG | 3135 |
| Met | Met | Ser | Leu | Phe | Thr | Val | Ser | Thr | Phe | Glu | Gly | Trp | Pro | Gln | Leu | |
| | 1005 | | | | 1010 | | | | | 1015 | | | | | | |
| CTG | TAC | AGG | GCC | ATA | GAC | TCC | AAC | GAG | GAG | GAC | ATG | GGC | CCC | GTT | TAC | 3183 |
| Leu | Tyr | Arg | Ala | Ile | Asp | Ser | Asn | Glu | Glu | Asp | Met | Gly | Pro | Val | Tyr | |

-continued

| | | | | |
|---|---|---|---|---|
| 1020 | 1025 | 1030 | 1035 | |

AAC AAC CGA GTG GAG ATG GCC ATC TTC TTC ATC ATC TAC ATC ATC CTC  3231
Asn Asn Arg Val Glu Met Ala Ile Phe Phe Ile Ile Tyr Ile Ile Leu
            1040                1045                1050

ATT GCC TTC TTC ATG ATG AAC ATC TTT GTG GGC TTT GTC ATC GTC ACC  3279
Ile Ala Phe Phe Met Met Asn Ile Phe Val Gly Phe Val Ile Val Thr
        1055                1060                1065

TTC CAG GAG CAG GGG GAG ACG GAG TAC AAG AAC TGC GAG CTG GAC AAG  3327
Phe Gln Glu Gln Gly Glu Thr Glu Tyr Lys Asn Cys Glu Leu Asp Lys
        1070                1075                1080

AAC CAG CGC CAG TGT GTG CAG TAT GCC CTG AAG GCC CGC CCA CTT CGG  3375
Asn Gln Arg Gln Cys Val Gln Tyr Ala Leu Lys Ala Arg Pro Leu Arg
        1085                1090                1095

TGC TAC ATC CCC AAG AAC CCA TAC CAG TAC CAG GTG TGG TAC GTC GTC  3423
Cys Tyr Ile Pro Lys Asn Pro Tyr Gln Tyr Gln Val Trp Tyr Val Val
    1100                1105                1110                1115

ACC TCC TCC TAC TTT GAA TAC CTG ATG TTC GCC CTC ATC ATG CTC AAC  3471
Thr Ser Ser Tyr Phe Glu Tyr Leu Met Phe Ala Leu Ile Met Leu Asn
        1120                1125                1130

ACC ATC TGC CTG GGC ATG CAG CAC TAC CAC CAG TCG GAG GAG ATG AAC  3519
Thr Ile Cys Leu Gly Met Gln His Tyr His Gln Ser Glu Glu Met Asn
    1135                1140                1145

CAC ATC TCA GAC ATC CTC AAT GTG GCC TTC ACC ATC ATC TTC ACG CTG  3567
His Ile Ser Asp Ile Leu Asn Val Ala Phe Thr Ile Ile Phe Thr Leu
    1150                1155                1160

GAG ATG ATT CTC AAG CTC TTG GCG TTC AAG GCC AGG GGC TAT TTC GGA  3615
Glu Met Ile Leu Lys Leu Leu Ala Phe Lys Ala Arg Gly Tyr Phe Gly
    1165                1170                1175

GAC CCC TGG AAT GTG TTC GAC TTC CTG ATC GTC ATC GGC AGC ATC ATT  3663
Asp Pro Trp Asn Val Phe Asp Phe Leu Ile Val Ile Gly Ser Ile Ile
1180                1185                1190                1195

GAC GTC ATC CTC AGC GAG ATC GAC ACT TTC CTG GCC TCC AGC GGG GGA  3711
Asp Val Ile Leu Ser Glu Ile Asp Thr Phe Leu Ala Ser Ser Gly Gly
            1200                1205                1210

CTG TAT TGC CTG GGT GGC GGC TGC GGG AAC GTT GAC CCA GAC GAG AGC  3759
Leu Tyr Cys Leu Gly Gly Gly Cys Gly Asn Val Asp Pro Asp Glu Ser
        1215                1220                1225

GCC CGC ATC TCC AGT GCC TTC TTC CGC CTG TTC CGG GTT ATG AGG CTG  3807
Ala Arg Ile Ser Ser Ala Phe Phe Arg Leu Phe Arg Val Met Arg Leu
    1230                1235                1240

ATC AAG CTG CTG AGT CGG GCC GAG GGC GTG CGC ACG CTG CTG TGG ACG  3855
Ile Lys Leu Leu Ser Arg Ala Glu Gly Val Arg Thr Leu Leu Trp Thr
    1245                1250                1255

TTC ATC AAG TCC TTC CAG GCC CTG CCC TAC GTG GCC CTG CTC ATC GTC  3903
Phe Ile Lys Ser Phe Gln Ala Leu Pro Tyr Val Ala Leu Leu Ile Val
1260                1265                1270                1275

ATG CTG TTC TTC ATC TAC GCC GTC ATC GGC ATG CAG ATG TTT GGA AAG  3951
Met Leu Phe Phe Ile Tyr Ala Val Ile Gly Met Gln Met Phe Gly Lys
        1280                1285                1290

ATC GCC CTG GTG GAC GGG ACC CAG ATC AAC CGC AAC AAC AAC TTC CAG  3999
Ile Ala Leu Val Asp Gly Thr Gln Ile Asn Arg Asn Asn Asn Phe Gln
        1295                1300                1305

ACC TTC CCG CAG GCC GTG CTG CTG CTC TTC AGG TGT GCG ACA GGG GAG  4047
Thr Phe Pro Gln Ala Val Leu Leu Leu Phe Arg Cys Ala Thr Gly Glu
    1310                1315                1320

GCG TGG CAA GAG ATC CTG CTG GCC TGC AGC TAC GGG AAG TTG TGC GAC  4095
Ala Trp Gln Glu Ile Leu Leu Ala Cys Ser Tyr Gly Lys Leu Cys Asp
    1325                1330                1335

CCA GAG TCA GAC TAC GCC CCG GGC GAG GAG TAC ACG TGT GGC ACC AAC  4143
Pro Glu Ser Asp Tyr Ala Pro Gly Glu Glu Tyr Thr Cys Gly Thr Asn

| | | | | | | | | | | | | | | | | |
|---|---|---|---|---|---|---|---|---|---|---|---|---|---|---|---|---|
| 1340 | | | | | 1345 | | | | | 1350 | | | | | 1355 | |
| TTC | GCC | TAC | TAC | TAC | TTC | ATC | AGC | TTC | TAC | ATG | CTC | TGC | GCC | TTC | CTG | 4191 |
| Phe | Ala | Tyr | Tyr | Tyr | Phe | Ile | Ser | Phe | Tyr | Met | Leu | Cys | Ala | Phe | Leu | |
| | | | 1360 | | | | | 1365 | | | | | 1370 | | | |
| ATC | ATC | AAC | CTC | TTC | GTG | GCT | GTC | ATC | ATG | GAC | AAC | TTT | GAC | TAC | CTG | 4239 |
| Ile | Ile | Asn | Leu | Phe | Val | Ala | Val | Ile | Met | Asp | Asn | Phe | Asp | Tyr | Leu | |
| | | | 1375 | | | | | 1380 | | | | | 1385 | | | |
| ACA | CGC | GAC | TGG | TCC | ATC | CTG | GGC | CCT | CAC | CAC | CTG | GAC | GAG | TTC | AAG | 4287 |
| Thr | Arg | Asp | Trp | Ser | Ile | Leu | Gly | Pro | His | His | Leu | Asp | Glu | Phe | Lys | |
| | | | 1390 | | | | | 1395 | | | | | 1400 | | | |
| GCC | ATC | TGG | GCA | GAG | TAT | GAC | CCA | GAG | GCC | AAG | GGG | CGA | ATC | AAG | CAC | 4335 |
| Ala | Ile | Trp | Ala | Glu | Tyr | Asp | Pro | Glu | Ala | Lys | Gly | Arg | Ile | Lys | His | |
| | | | 1405 | | | | | 1410 | | | | | 1415 | | | |
| CTG | GAC | GTG | GTG | ACC | CTG | CTG | AGA | AGG | ATC | CAG | CCC | CCT | CTG | GGC | TTC | 4383 |
| Leu | Asp | Val | Val | Thr | Leu | Leu | Arg | Arg | Ile | Gln | Pro | Pro | Leu | Gly | Phe | |
| 1420 | | | | | 1425 | | | | | 1430 | | | | | 1435 | |
| GGG | AAG | TTC | TGT | CCA | CAC | CGG | GTG | GCC | TGT | AAG | CGC | CTG | GTG | GGC | ATG | 4431 |
| Gly | Lys | Phe | Cys | Pro | His | Arg | Val | Ala | Cys | Lys | Arg | Leu | Val | Gly | Met | |
| | | | 1440 | | | | | 1445 | | | | | 1450 | | | |
| AAC | ATG | CCC | CTG | AAC | AGT | GAC | GGC | ACG | GTC | ACC | TTC | AAT | GCC | ACG | CTC | 4479 |
| Asn | Met | Pro | Leu | Asn | Ser | Asp | Gly | Thr | Val | Thr | Phe | Asn | Ala | Thr | Leu | |
| | | | 1455 | | | | | 1460 | | | | | 1465 | | | |
| TTT | GCC | CTG | GTG | CGC | ACG | GCC | CTC | AAG | ATC | AAG | ACA | GAA | GGT | AAC | TTC | 4527 |
| Phe | Ala | Leu | Val | Arg | Thr | Ala | Leu | Lys | Ile | Lys | Thr | Glu | Gly | Asn | Phe | |
| | | | 1470 | | | | | 1475 | | | | | 1480 | | | |
| GAG | CAG | GCC | AAC | GAG | GAG | CTG | AGG | GCC | ATC | ATC | AAG | AAG | ATC | TGG | AAG | 4575 |
| Glu | Gln | Ala | Asn | Glu | Glu | Leu | Arg | Ala | Ile | Ile | Lys | Lys | Ile | Trp | Lys | |
| | | | 1485 | | | | | 1490 | | | | | 1495 | | | |
| AGA | ACC | AGC | ATG | AAG | CTA | CTG | GAC | CAG | GTC | ATC | CCT | CCC | ATA | GGA | GAT | 4623 |
| Arg | Thr | Ser | Met | Lys | Leu | Leu | Asp | Gln | Val | Ile | Pro | Pro | Ile | Gly | Asp | |
| 1500 | | | | | 1505 | | | | | 1510 | | | | | 1515 | |
| GAC | GAG | GTG | ACC | GTG | GGG | AAG | TTC | TAC | GCC | ACA | TTC | CTC | ATC | CAG | GAG | 4671 |
| Asp | Glu | Val | Thr | Val | Gly | Lys | Phe | Tyr | Ala | Thr | Phe | Leu | Ile | Gln | Glu | |
| | | | 1520 | | | | | 1525 | | | | | 1530 | | | |
| CAC | TTC | CGG | AAG | TTC | ATG | AAG | CGC | CAG | GAG | GAA | TAT | TAT | GGG | TAT | CGG | 4719 |
| His | Phe | Arg | Lys | Phe | Met | Lys | Arg | Gln | Glu | Glu | Tyr | Tyr | Gly | Tyr | Arg | |
| | | | 1535 | | | | | 1540 | | | | | 1545 | | | |
| CCC | AAG | AAG | GAC | ACC | GTG | CAG | ATC | CAG | GCT | GGG | CTG | CGG | ACC | ATA | GAG | 4767 |
| Pro | Lys | Lys | Asp | Thr | Val | Gln | Ile | Gln | Ala | Gly | Leu | Arg | Thr | Ile | Glu | |
| | | | 1550 | | | | | 1555 | | | | | 1560 | | | |
| GAG | GAG | GCG | GCC | CCT | GAG | ATC | CGC | CGC | ACC | ATC | TCA | GGA | GAC | CTG | ACC | 4815 |
| Glu | Glu | Ala | Ala | Pro | Glu | Ile | Arg | Arg | Thr | Ile | Ser | Gly | Asp | Leu | Thr | |
| | | | 1565 | | | | | 1570 | | | | | 1575 | | | |
| GCC | GAG | GAG | GAG | CTG | GAG | AGA | GCC | ATG | GTG | GAG | GCT | GCG | ATG | GAG | GAG | 4863 |
| Ala | Glu | Glu | Glu | Leu | Glu | Arg | Ala | Met | Val | Glu | Ala | Ala | Met | Glu | Glu | |
| 1580 | | | | | 1585 | | | | | 1590 | | | | | 1595 | |
| AGG | ATC | TTC | CGG | AGG | ACC | GGA | GGC | CTG | TTT | GGC | CAG | GTG | GAC | ACC | TTC | 4911 |
| Arg | Ile | Phe | Arg | Arg | Thr | Gly | Gly | Leu | Phe | Gly | Gln | Val | Asp | Thr | Phe | |
| | | | 1600 | | | | | 1605 | | | | | 1610 | | | |
| CTG | GAA | AGG | ACC | AAC | TCC | CTA | CCC | CCG | GTG | ATG | GCC | AAC | CAA | AGA | CCG | 4959 |
| Leu | Glu | Arg | Thr | Asn | Ser | Leu | Pro | Pro | Val | Met | Ala | Asn | Gln | Arg | Pro | |
| | | | 1615 | | | | | 1620 | | | | | 1625 | | | |
| CTC | CAG | TTT | GCT | GAG | ATA | GAA | ATG | GAA | GAG | CTT | GAG | TCG | CCT | GTC | TTC | 5007 |
| Leu | Gln | Phe | Ala | Glu | Ile | Glu | Met | Glu | Glu | Leu | Glu | Ser | Pro | Val | Phe | |
| | | | 1630 | | | | | 1635 | | | | | 1640 | | | |
| TTG | GAG | GAC | TTC | CCT | CAA | GAC | GCA | AGA | ACC | AAC | CCT | CTC | GCT | CGT | GCC | 5055 |
| Leu | Glu | Asp | Phe | Pro | Gln | Asp | Ala | Arg | Thr | Asn | Pro | Leu | Ala | Arg | Ala | |
| | | | 1645 | | | | | 1650 | | | | | 1655 | | | |
| AAT | ACC | AAC | AAC | GCC | AAT | GCC | AAT | GTT | GCC | TAT | GGC | AAC | AGC | AAC | CAT | 5103 |
| Asn | Thr | Asn | Asn | Ala | Asn | Ala | Asn | Val | Ala | Tyr | Gly | Asn | Ser | Asn | His | |

-continued

| | | | |
|---|---|---|---|
| 1660 | 1665 | 1670 | 1675 |

AGC AAC AAC CAG ATG TTT TCC AGC GTC CAC TGT GAA AGG GAG TTC CCG   5151
Ser Asn Asn Gln Met Phe Ser Ser Val His Cys Glu Arg Glu Phe Pro
         1680              1685              1690

GGA GAG GCG GAG ACA CCG GCT GCC GGA CGA GGA GCC CTC AGC CAC TCC   5199
Gly Glu Ala Glu Thr Pro Ala Ala Gly Arg Gly Ala Leu Ser His Ser
         1695              1700              1705

CAC AGG GCC CTG GGA CCT CAC AGC AAG CCC TGT GCT GGA AAA CTG AAT   5247
His Arg Ala Leu Gly Pro His Ser Lys Pro Cys Ala Gly Lys Leu Asn
         1710              1715              1720

GGG CAG CTG GTC CAG CCG GGA ATG CCC ATC AAC CAG GCA CCT CCT GCC   5295
Gly Gln Leu Val Gln Pro Gly Met Pro Ile Asn Gln Ala Pro Pro Ala
         1725              1730              1735

CCC TGC CAG CAG CCT AGC ACA GAT CCC CCA GAG CGC GGG CAG AGG AGG   5343
Pro Cys Gln Gln Pro Ser Thr Asp Pro Pro Glu Arg Gly Gln Arg Arg
1740              1745              1750              1755

ACC TCC CTG ACA GGG TCT CTG CAA GAC GAA GCA CCC CAG AGG AGG AGC   5391
Thr Ser Leu Thr Gly Ser Leu Gln Asp Glu Ala Pro Gln Arg Arg Ser
         1760              1765              1770

TCC GAG GGG AGC ACC CCC AGG CGC CCG GCT CCT GCT ACA GCT CTG CTG   5439
Ser Glu Gly Ser Thr Pro Arg Arg Pro Ala Pro Ala Thr Ala Leu Leu
         1775              1780              1785

ATC CAA GAG GCT CTG GTT CGA GGG GGC CTG GAC ACC TTG GCA GCT GAT   5487
Ile Gln Glu Ala Leu Val Arg Gly Gly Leu Asp Thr Leu Ala Ala Asp
         1790              1795              1800

GCT GGC TTC GTC ATG GCA ACA AGC CAG GCC CTG GTA GAC GCC TGT CAG   5535
Ala Gly Phe Val Met Ala Thr Ser Gln Ala Leu Val Asp Ala Cys Gln
         1805              1810              1815

ATG GAA CCG GAG GAA GTA GAG GTC GCA GCC ACA GAG CTA CTG AAA GAG   5583
Met Glu Pro Glu Glu Val Glu Val Ala Ala Thr Glu Leu Leu Lys Glu
1820              1825              1830              1835

CGA GAG TCC GTC CAG GGC ATG GCC AGT GTC CCG GGA AGC CTG AGC CGC   5631
Arg Glu Ser Val Gln Gly Met Ala Ser Val Pro Gly Ser Leu Ser Arg
         1840              1845              1850

AGG TCC TCC CTG GGC AGC CTT GAC CAG GTC CAG GGC TCC CAG GAA ACC   5679
Arg Ser Ser Leu Gly Ser Leu Asp Gln Val Gln Gly Ser Gln Glu Thr
         1855              1860              1865

CTT ATT CCT CCC AGG CCG TGA TGGCTGTGCA GTGTCCACAT GACCAAGGCG AGGGG   5735
Leu Ile Pro Pro Arg Pro *
         1870

GACAGTGCGT GCAGAAGCTC AGCCCTGCAT GGCAGCCTCC CTCTGTCTCA GCCCTCCTGC   5795

TGAGCTGGGG CGGTCTGGAA CCGACCAGGA AGCCAGGAGC CTCCCCTGGC CAGCAAGAGG   5855

CATGATTCTA AAGCATCCAG AAAGGCCTGG TCAGTGCCAC TCCCCAGCAG GACATTAAAG   5915

TCTCTAGGTC TGTGGCAAAA AAAAAAAAAA AAAAAAAAAA AAAAAAAAAA AAAAAAAAAA   5975

( 2 ) INFORMATION FOR SEQ ID NO:2:

( i ) SEQUENCE CHARACTERISTICS:
      ( A ) LENGTH: 3802 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: Coding Sequence
      ( B ) LOCATION: 309...3630
      ( A ) NAME/KEY: mat_peptide
      ( B ) LOCATION: 387...3626
      ( D ) OTHER INFORMATION:

( x i ) SEQUENCE DESCRIPTION: SEQ ID NO:2:

| | | | | | | | |
|---|---|---|---|---|---|---|---|
| AGAAGGGAGG | GCGAGCGTGG | TGTGTGCGCG | CTCGGGCGCC | GGCGGCACCG | CCGAGGTCTG | | 60 |
| TTGGCAAAAG | TCGCCCTTGA | TGGCGGCGGA | GGCGAGGCAG | CCGCGGCGCC | GAACAGCCGA | | 120 |
| CGCGCGCTAG | CGGGGTCCGC | CGCCCCTTT | CCCAGAGCCC | AGCGCCGCCG | TTCGCCGCCG | | 180 |
| CCGCCGCCCG | CCCGCGCGCC | GTTCGCCGCC | GCCGCCGCCC | GCGGGTGGCA | GCGCCGCTCG | | 240 |
| GTCCCCGGCC | CCGGGGCCGG | CTGGGGGGCG | GTCGGGGCGT | GTGAGGGGCT | TGCTCCCAGC | | 300 |

```
TCGCGAAG ATG GCT GCG GGC CGC CCG CTG GCC TGG ACG CTG ACA CTT TGG        350
         Met Ala Ala Gly Arg Pro Leu Ala Trp Thr Leu Thr Leu Trp
         -26 -25              -20                    -15

CAG GCG TGG CTG ATC CTG ATC GGG CCC TCG TCG GAG GAG CCG TTC CCT        398
Gln Ala Trp Leu Ile Leu Ile Gly Pro Ser Ser Glu Glu Pro Phe Pro
        -10                  -5                    -1   1

TCA GCC GTC ACT ATC AAG TCA TGG GTG GAT AAG ATG CAA GAA GAC CTG        446
Ser Ala Val Thr Ile Lys Ser Trp Val Asp Lys Met Gln Glu Asp Leu
 5                    10                  15                  20

GTC ACA CTG GCA AAA ACA GCA AGT GGA GTC AAT CAG CTT GTT GAT ATT        494
Val Thr Leu Ala Lys Thr Ala Ser Gly Val Asn Gln Leu Val Asp Ile
                  25              30                  35

TAT GAG AAA TAT CAA GAT TTG TAT ACT GTG GAA CCA AAT AAT GCA CGT        542
Tyr Glu Lys Tyr Gln Asp Leu Tyr Thr Val Glu Pro Asn Asn Ala Arg
              40                  45                  50

CAG CTG GTG GAA ATT GCA GCC AGA GAC ATT GAG AAG CTT CTC AGC AAC        590
Gln Leu Val Glu Ile Ala Ala Arg Asp Ile Glu Lys Leu Leu Ser Asn
          55                  60                  65

AGA TCT AAA GCC CTG GTG CGC CTG GCT TTG GAA GCA GAG AAA GTT CAA        638
Arg Ser Lys Ala Leu Val Arg Leu Ala Leu Glu Ala Glu Lys Val Gln
     70                  75                  80

GCA GCC CAC CAA TGG AGG GAA GAT TTT GCA AGC AAT GAA GTT GTC TAC        686
Ala Ala His Gln Trp Arg Glu Asp Phe Ala Ser Asn Glu Val Val Tyr
 85                  90                  95                 100

TAT AAC GCG AAG GAT GAT CTT GAT CCT GAA AAA AAT GAC AGT GAA CCA        734
Tyr Asn Ala Lys Asp Asp Leu Asp Pro Glu Lys Asn Asp Ser Glu Pro
                 105                 110                 115

GGC AGC CAG AGG ATC AAA CCT GTT TTC ATT GAC GAT GCT AAC TTT AGA        782
Gly Ser Gln Arg Ile Lys Pro Val Phe Ile Asp Asp Ala Asn Phe Arg
             120                 125                 130

AGA CAA GTA TCC TAT CAG CAC GCA GCT GTC CAT ATC CCC ACT GAC ATC        830
Arg Gln Val Ser Tyr Gln His Ala Ala Val His Ile Pro Thr Asp Ile
         135                 140                 145

TAT GAA GGA TCG ACA ATC GTG TTA AAC GAA CTC AAC TGG ACA AGT GCC        878
Tyr Glu Gly Ser Thr Ile Val Leu Asn Glu Leu Asn Trp Thr Ser Ala
150                 155                 160

TTA GAT GAC GTT TTC AAA AAA AAT CGA GAG GAA GAC CCT TCA CTG TTG        926
Leu Asp Asp Val Phe Lys Lys Asn Arg Glu Glu Asp Pro Ser Leu Leu
165                 170                 175                 180

TGG CAG GTG TTT GGC AGT GCC ACT GGC CTG GCC CGG TAT TAC CCA GCT        974
Trp Gln Val Phe Gly Ser Ala Thr Gly Leu Ala Arg Tyr Tyr Pro Ala
                185                 190                 195

TCT CCA TGG GTT GAT AAT AGC CGA ACC CCA AAC AAG ATT GAT CTT TAT       1022
Ser Pro Trp Val Asp Asn Ser Arg Thr Pro Asn Lys Ile Asp Leu Tyr
            200                 205                 210

GAT GTA CGC AGA AGA CCA TGG TAC ATC CAA GGT GCT GCA TCC CCT AAA       1070
Asp Val Arg Arg Arg Pro Trp Tyr Ile Gln Gly Ala Ala Ser Pro Lys
        215                 220                 225

GAT ATG CTT ATT CTG GTG GAT GTG AGT GGA AGC GTT AGT GGA CTG ACA       1118
Asp Met Leu Ile Leu Val Asp Val Ser Gly Ser Val Ser Gly Leu Thr
    230                 235                 240
```

```
CTC AAA CTC ATC CGG ACA TCC GTC TCC GAA ATG TTG GAA ACC CTC TCA    1166
Leu Lys Leu Ile Arg Thr Ser Val Ser Glu Met Leu Glu Thr Leu Ser
245             250                 255                 260

GAT GAT GAT TTT GTG AAC GTG GCT TCA TTT AAC AGC AAT GCT CAG GAT    1214
Asp Asp Asp Phe Val Asn Val Ala Ser Phe Asn Ser Asn Ala Gln Asp
                265                 270                 275

GTA AGC TGC TTT CAG CAC CTT GTC CAA GCA AAT GTA AGA AAT AAG AAA    1262
Val Ser Cys Phe Gln His Leu Val Gln Ala Asn Val Arg Asn Lys Lys
            280                 285                 290

GTG TTG AAA GAT GCA GTG AAT AAT ATC ACA GCA AAA GGA ATC ACA GAT    1310
Val Leu Lys Asp Ala Val Asn Asn Ile Thr Ala Lys Gly Ile Thr Asp
        295                 300                 305

TAT AAG AAG GGC TTT AGT TTT GCT TTT GAG CAG CTG CTT AAT TAT AAT    1358
Tyr Lys Lys Gly Phe Ser Phe Ala Phe Glu Gln Leu Leu Asn Tyr Asn
    310                 315                 320

GTA TCC AGA GCC AAC TGC AAT AAG ATT ATC ATG TTG TTC ACG GAC GGA    1406
Val Ser Arg Ala Asn Cys Asn Lys Ile Ile Met Leu Phe Thr Asp Gly
325                 330                 335                 340

GGA GAA GAG AGA GCC CAG GAG ATA TTT GCC AAA TAC AAT AAA GAC AAG    1454
Gly Glu Glu Arg Ala Gln Glu Ile Phe Ala Lys Tyr Asn Lys Asp Lys
                345                 350                 355

AAA GTA CGT GTA TTC ACA TTC TCA GTT GGC CAA CAT AAT TAC GAC AGA    1502
Lys Val Arg Val Phe Thr Phe Ser Val Gly Gln His Asn Tyr Asp Arg
            360                 365                 370

GGA CCT ATT CAG TGG ATG GCT TGC GAA AAT AAA GGT TAT TAT TAT GAA    1550
Gly Pro Ile Gln Trp Met Ala Cys Glu Asn Lys Gly Tyr Tyr Tyr Glu
        375                 380                 385

ATT CCA TCC ATT GGA GCC ATA AGA ATT AAT ACT CAG GAA TAC CTA GAT    1598
Ile Pro Ser Ile Gly Ala Ile Arg Ile Asn Thr Gln Glu Tyr Leu Asp
    390                 395                 400

GTT CTG GGA AGA CCG ATG GTT TTA GCA GGA GAC AAA GCT AAG CAA GTC    1646
Val Leu Gly Arg Pro Met Val Leu Ala Gly Asp Lys Ala Lys Gln Val
405                 410                 415                 420

CAA TGG ACA AAT GTG TAC CTG GAT GCA CTG GAA CTG GGA CTT GTC ATT    1694
Gln Trp Thr Asn Val Tyr Leu Asp Ala Leu Glu Leu Gly Leu Val Ile
                425                 430                 435

ACT GGA ACT CTT CCG GTC TTC AAC ATA ACT GGC CAA TTT GAA AAT AAG    1742
Thr Gly Thr Leu Pro Val Phe Asn Ile Thr Gly Gln Phe Glu Asn Lys
            440                 445                 450

ACA AAC TTA AAG AAC CAG CTG ATT CTT GGA GTG ATG GGA GTT GAT GTG    1790
Thr Asn Leu Lys Asn Gln Leu Ile Leu Gly Val Met Gly Val Asp Val
        455                 460                 465

TCT TTG GAA GAT ATT AAA AGA CTG ACA CCA CGT TTT ACA CTC TGC CCC    1838
Ser Leu Glu Asp Ile Lys Arg Leu Thr Pro Arg Phe Thr Leu Cys Pro
    470                 475                 480

AAT GGC TAC TAT TTT GCA ATT GAT CCT AAT GGT TAT GTG TTA TTA CAT    1886
Asn Gly Tyr Tyr Phe Ala Ile Asp Pro Asn Gly Tyr Val Leu Leu His
485                 490                 495                 500

CCA AAT CTT CAG CCA AAG CCT ATT GGT GTA GGT ATA CCA ACA ATT AAT    1934
Pro Asn Leu Gln Pro Lys Pro Ile Gly Val Gly Ile Pro Thr Ile Asn
                505                 510                 515

TTG AGA AAA AGG AGA CCC AAT GTT CAG AAC CCC AAA TCT CAG GAG CCA    1982
Leu Arg Lys Arg Arg Pro Asn Val Gln Asn Pro Lys Ser Gln Glu Pro
            520                 525                 530

GTG ACA TTG GAT TTC CTC GAT GCA GAG TTG GAG AAT GAC ATT AAA GTG    2030
Val Thr Leu Asp Phe Leu Asp Ala Glu Leu Glu Asn Asp Ile Lys Val
        535                 540                 545

GAG ATT CGA AAT AAA ATG ATC GAT GGA GAA AGT GGA GAA AAA ACA TTC    2078
Glu Ile Arg Asn Lys Met Ile Asp Gly Glu Ser Gly Glu Lys Thr Phe
    550                 555                 560
```

-continued

| | | | | | | | | | | | | | | | | |
|---|---|---|---|---|---|---|---|---|---|---|---|---|---|---|---|---|
| AGA | ACT | CTG | GTT | AAA | TCT | CAA | GAT | GAG | AGA | TAT | ATT | GAC | AAA | GGA | AAC | 2126 |
| Arg | Thr | Leu | Val | Lys | Ser | Gln | Asp | Glu | Arg | Tyr | Ile | Asp | Lys | Gly | Asn | |
| 565 | | | | 570 | | | | | 575 | | | | | 580 | | |
| AGG | ACA | TAC | ACG | TGG | ACT | CCT | GTC | AAC | GGC | ACA | GAT | TAT | AGC | AGT | TTG | 2174 |
| Arg | Thr | Tyr | Thr | Trp | Thr | Pro | Val | Asn | Gly | Thr | Asp | Tyr | Ser | Ser | Leu | |
| | | | | 585 | | | | 590 | | | | | 595 | | | |
| GCC | TTG | GTA | TTA | CCA | ACC | TAC | AGT | TTT | TAC | TAT | ATA | AAA | GCC | AAA | ATA | 2222 |
| Ala | Leu | Val | Leu | Pro | Thr | Tyr | Ser | Phe | Tyr | Tyr | Ile | Lys | Ala | Lys | Ile | |
| | | | 600 | | | | 605 | | | | | 610 | | | | |
| GAA | GAG | ACA | ATA | ACT | CAG | GCC | AGA | TAT | TCA | GAA | ACA | CTG | AAA | CCG | GAT | 2270 |
| Glu | Glu | Thr | Ile | Thr | Gln | Ala | Arg | Tyr | Ser | Glu | Thr | Leu | Lys | Pro | Asp | |
| | | 615 | | | | 620 | | | | | 625 | | | | | |
| AAT | TTT | GAA | GAA | TCT | GGC | TAC | ACA | TTC | CTA | GCA | CCA | AGA | GAT | TAC | TGC | 2318 |
| Asn | Phe | Glu | Glu | Ser | Gly | Tyr | Thr | Phe | Leu | Ala | Pro | Arg | Asp | Tyr | Cys | |
| | 630 | | | | 635 | | | | | 640 | | | | | | |
| AGT | GAC | CTT | AAA | CCT | TCA | GAT | AAT | AAC | ACT | GAA | TTT | CTT | TTA | AAT | TTC | 2366 |
| Ser | Asp | Leu | Lys | Pro | Ser | Asp | Asn | Asn | Thr | Glu | Phe | Leu | Leu | Asn | Phe | |
| 645 | | | | 650 | | | | | 655 | | | | | 660 | | |
| AAT | GAG | TTT | ATT | GAT | AGA | AAA | ACT | CCA | AAC | AAC | CCA | TCC | TGT | AAT | ACA | 2414 |
| Asn | Glu | Phe | Ile | Asp | Arg | Lys | Thr | Pro | Asn | Asn | Pro | Ser | Cys | Asn | Thr | |
| | | | | 665 | | | | | 670 | | | | | 675 | | |
| GAC | TTG | ATT | AAT | AGA | GTC | TTG | CTG | GAT | GCA | GGC | TTT | ACA | AAT | GAA | CTT | 2462 |
| Asp | Leu | Ile | Asn | Arg | Val | Leu | Leu | Asp | Ala | Gly | Phe | Thr | Asn | Glu | Leu | |
| | | | 680 | | | | | 685 | | | | | 690 | | | |
| GTT | CAA | AAT | TAC | TGG | AGT | AAG | CAG | AAG | AAT | ATC | AAG | GGA | GTG | AAA | GCA | 2510 |
| Val | Gln | Asn | Tyr | Trp | Ser | Lys | Gln | Lys | Asn | Ile | Lys | Gly | Val | Lys | Ala | |
| | | 695 | | | | | 700 | | | | | 705 | | | | |
| CGG | TTT | GTT | GTG | ACT | GAT | GGT | GGG | ATT | ACC | AGA | GTT | TAT | CCC | AAA | GAG | 2558 |
| Arg | Phe | Val | Val | Thr | Asp | Gly | Gly | Ile | Thr | Arg | Val | Tyr | Pro | Lys | Glu | |
| 710 | | | | | 715 | | | | | 720 | | | | | | |
| GCT | GGA | GAA | AAT | TGG | CAG | GAA | AAC | CCA | GAG | ACA | TAT | GAA | GAC | AGC | TTC | 2606 |
| Ala | Gly | Glu | Asn | Trp | Gln | Glu | Asn | Pro | Glu | Thr | Tyr | Glu | Asp | Ser | Phe | |
| 725 | | | | | 730 | | | | | 735 | | | | | 740 | |
| TAT | AAA | AGG | AGC | CTC | GAT | AAT | GAT | AAC | TAC | GTT | TTC | ACT | GCT | CCC | TAC | 2654 |
| Tyr | Lys | Arg | Ser | Leu | Asp | Asn | Asp | Asn | Tyr | Val | Phe | Thr | Ala | Pro | Tyr | |
| | | | | 745 | | | | | 750 | | | | | 755 | | |
| TTT | AAC | AAA | AGT | GGA | CCT | GGG | GCC | TAT | GAG | TCA | GGC | ATT | ATG | GTA | AGC | 2702 |
| Phe | Asn | Lys | Ser | Gly | Pro | Gly | Ala | Tyr | Glu | Ser | Gly | Ile | Met | Val | Ser | |
| | | | 760 | | | | | 765 | | | | | 770 | | | |
| AAA | GCT | GTA | GAA | ATA | TAT | ATC | CAA | GGA | AAA | CTT | CTT | AAA | CCT | GCA | GTT | 2750 |
| Lys | Ala | Val | Glu | Ile | Tyr | Ile | Gln | Gly | Lys | Leu | Leu | Lys | Pro | Ala | Val | |
| | | 775 | | | | | 780 | | | | | 785 | | | | |
| GTT | GGA | ATT | AAA | ATT | GAT | GTA | AAT | TCT | TGG | ATA | GAG | AAT | TTC | ACC | AAA | 2798 |
| Val | Gly | Ile | Lys | Ile | Asp | Val | Asn | Ser | Trp | Ile | Glu | Asn | Phe | Thr | Lys | |
| 790 | | | | | 795 | | | | | 800 | | | | | | |
| ACT | TCA | ATC | AGG | GAT | CCG | TGT | GCT | GGT | CCA | GTT | TGT | GAC | TGC | AAA | CGA | 2846 |
| Thr | Ser | Ile | Arg | Asp | Pro | Cys | Ala | Gly | Pro | Val | Cys | Asp | Cys | Lys | Arg | |
| 805 | | | | | 810 | | | | | 815 | | | | | 820 | |
| AAC | AGT | GAT | GTA | ATG | GAT | TGT | GTG | ATT | CTA | GAT | GAC | GGT | GGG | TTT | CTT | 2894 |
| Asn | Ser | Asp | Val | Met | Asp | Cys | Val | Ile | Leu | Asp | Asp | Gly | Gly | Phe | Leu | |
| | | | | 825 | | | | | 830 | | | | | 835 | | |
| TTG | ATG | GCC | AAC | CAT | GAT | GAT | TAT | ACC | AAT | CAG | ATT | GGA | AGA | TTC | TTT | 2942 |
| Leu | Met | Ala | Asn | His | Asp | Asp | Tyr | Thr | Asn | Gln | Ile | Gly | Arg | Phe | Phe | |
| | | | 840 | | | | 845 | | | | | 850 | | | | |
| GGA | GAG | ATT | GAT | CCA | AGC | TTG | ATG | AGA | CAC | CTG | GTC | AAT | ATA | TCA | GTT | 2990 |
| Gly | Glu | Ile | Asp | Pro | Ser | Leu | Met | Arg | His | Leu | Val | Asn | Ile | Ser | Val | |
| | | 855 | | | | | 860 | | | | | 865 | | | | |
| TAT | GCC | TTT | AAC | AAA | TCT | TAT | GAT | TAT | CAG | TCG | GTG | TGT | GAA | CCT | GGT | 3038 |
| Tyr | Ala | Phe | Asn | Lys | Ser | Tyr | Asp | Tyr | Gln | Ser | Val | Cys | Glu | Pro | Gly | |
| | 870 | | | | | 875 | | | | | 880 | | | | | |

-continued

| | | | | | | | | | | | | | | | | |
|---|---|---|---|---|---|---|---|---|---|---|---|---|---|---|---|---|
| GCT | GCG | CCA | AAG | CAG | GGA | GCA | GGG | CAC | CGC | TCG | GCT | TAT | GTG | CCA | TCA | 3086 |
| Ala | Ala | Pro | Lys | Gln | Gly | Ala | Gly | His | Arg | Ser | Ala | Tyr | Val | Pro | Ser | |
| 885 | | | | 890 | | | | | 895 | | | | | 900 | | |
| ATA | GCA | GAC | ATA | CTG | CAG | ATT | GGA | TGG | TGG | GCC | ACT | GCT | GCT | GCC | TGG | 3134 |
| Ile | Ala | Asp | Ile | Leu | Gln | Ile | Gly | Trp | Trp | Ala | Thr | Ala | Ala | Ala | Trp | |
| | | | 905 | | | | | 910 | | | | | 915 | | | |
| TCT | ATT | CTT | CAG | CAG | TTT | CTG | TTG | AGT | TTG | ACT | TTT | CCA | CGG | CTC | CTT | 3182 |
| Ser | Ile | Leu | Gln | Gln | Phe | Leu | Leu | Ser | Leu | Thr | Phe | Pro | Arg | Leu | Leu | |
| | | | 920 | | | | | 925 | | | | | 930 | | | |
| GAG | GCA | GCT | GAT | ATG | GAG | GAT | GAC | GAC | TTC | ACT | GCC | TCC | ATG | TCA | AAG | 3230 |
| Glu | Ala | Ala | Asp | Met | Glu | Asp | Asp | Asp | Phe | Thr | Ala | Ser | Met | Ser | Lys | |
| | | 935 | | | | | 940 | | | | | 945 | | | | |
| CAG | AGC | TGC | ATC | ACT | GAG | CAA | ACC | CAG | TAT | TTC | TTC | GAT | AAT | GAC | AGC | 3278 |
| Gln | Ser | Cys | Ile | Thr | Glu | Gln | Thr | Gln | Tyr | Phe | Phe | Asp | Asn | Asp | Ser | |
| | 950 | | | | | 955 | | | | | 960 | | | | | |
| AAA | TCG | TTC | AGT | GGG | GTA | TTA | GAC | TGT | GGG | AAT | TGT | TCC | AGA | ATC | TTT | 3326 |
| Lys | Ser | Phe | Ser | Gly | Val | Leu | Asp | Cys | Gly | Asn | Cys | Ser | Arg | Ile | Phe | |
| 965 | | | | 970 | | | | | 975 | | | | | 980 | | |
| CAT | GTA | GAA | AAG | CTC | ATG | AAC | ACC | AAT | TTA | ATA | TTC | ATA | ATG | GTA | GAG | 3374 |
| His | Val | Glu | Lys | Leu | Met | Asn | Thr | Asn | Leu | Ile | Phe | Ile | Met | Val | Glu | |
| | | | | 985 | | | | 990 | | | | | 995 | | | |
| AGC | AAG | GGG | ACA | TGT | CCC | TGT | GAC | ACA | CGG | CTG | CTC | ATA | CAA | GCA | GAG | 3422 |
| Ser | Lys | Gly | Thr | Cys | Pro | Cys | Asp | Thr | Arg | Leu | Leu | Ile | Gln | Ala | Glu | |
| | | | 1000 | | | | 1005 | | | | | 1010 | | | | |
| CAA | ACT | TCT | GAT | GGA | CCA | GAT | CCT | TGT | GAT | ATG | GTT | AAG | CAA | CCC | AGA | 3470 |
| Gln | Thr | Ser | Asp | Gly | Pro | Asp | Pro | Cys | Asp | Met | Val | Lys | Gln | Pro | Arg | |
| | | 1015 | | | | | 1020 | | | | | 1025 | | | | |
| TAT | CGA | AAA | GGG | CCA | GAT | GTC | TGC | TTT | GAC | AAC | AAT | GTC | CTG | GAG | GAT | 3518 |
| Tyr | Arg | Lys | Gly | Pro | Asp | Val | Cys | Phe | Asp | Asn | Asn | Val | Leu | Glu | Asp | |
| | 1030 | | | | | 1035 | | | | | 1040 | | | | | |
| TAT | ACT | GAC | TGC | GGT | GGG | GTC | TCT | GGA | TTA | AAT | CCT | TCC | CTG | TGG | TCC | 3566 |
| Tyr | Thr | Asp | Cys | Gly | Gly | Val | Ser | Gly | Leu | Asn | Pro | Ser | Leu | Trp | Ser | |
| 1045 | | | | 1050 | | | | | 1055 | | | | | 1060 | | |
| ATC | ATC | GGG | ATA | CAG | TTT | GTA | CTG | CTT | TGG | CTG | GTT | TCT | GGC | AGC | AGA | 3614 |
| Ile | Ile | Gly | Ile | Gln | Phe | Val | Leu | Leu | Trp | Leu | Val | Ser | Gly | Ser | Arg | |
| | | | | 1065 | | | | 1070 | | | | | 1075 | | | |
| CAC | TGC | CTG | TTA | TGA | C CTTCTAAAAC | CAAATCTCCA | TAATTAAACT | CCAGACCCTG | 3670 |
| His | Cys | Leu | Leu | * | | | | | |
| | | | 1080 | | | | | | |

CCACAACATG ATCCCTCCGT TATGTTAAAG TAGGGTCAAC TGTTAAATCA GAACATTAGC    3730

TGGGCCTCTG CCATGGCAGA GCCCTAAGGC GCAGACTCAT CAGGCACCCA CTGGCTGCAT    3790

GTCAGGGTGT CC    3802

( 2 ) INFORMATION FOR SEQ ID NO:3:

( i ) SEQUENCE CHARACTERISTICS:
        ( A ) LENGTH: 1560 base pairs
        ( B ) TYPE: nucleic acid
        ( C ) STRANDEDNESS: single
        ( D ) TOPOLOGY: unknown ( i i ) MOLECULE TYPE: Genomic DNA ( i x ) FEATURE:
        ( A ) NAME/KEY: Coding Sequence
        ( B ) LOCATION: 35...1558

( x i ) SEQUENCE DESCRIPTION: SEQ ID NO:3:

| | | | | | | | | | | |
|---|---|---|---|---|---|---|---|---|---|---|
| GGGCGGGGGA | GGGGGATTGA | TCTTCGATCG | CAAG | ATG | GCT | GCT | GGC | TGC | CTG | CTG | 55 |
| | | | | Met | Ala | Ala | Gly | Cys | Leu | Leu | |
| | | | | 1 | | | | 5 | | | |

| | | | | | | | | | | | | | | | |
|---|---|---|---|---|---|---|---|---|---|---|---|---|---|---|---|
| GCC | TTG | ACT | CTG | ACA | CTT | TTC | CAA | TCT | TTG | CTC | ATC | GGC | CCC | TCG | TCG | 103 |

-continued

```
                    Ala Leu Thr Leu Thr Leu Phe Gln Ser Leu Leu Ile Gly Pro Ser Ser
                             10                  15                  20

GAG GAG CCG TTC CCT TCG GCC GTC ACT ATC AAA TCA TGG GTG GAT AAG                151
Glu Glu Pro Phe Pro Ser Ala Val Thr Ile Lys Ser Trp Val Asp Lys
     25              30                  35

ATG CAA GAA GAC CTT GTC ACA CTG GCA AAA ACA GCA AGT GGA GTC AAT                199
Met Gln Glu Asp Leu Val Thr Leu Ala Lys Thr Ala Ser Gly Val Asn
40                  45              50                  55

CAG CTT GTT GAT ATT TAT GAG AAA TAT CAA GAT TTG TAT ACT GTG GAA                247
Gln Leu Val Asp Ile Tyr Glu Lys Tyr Gln Asp Leu Tyr Thr Val Glu
                    60                  65                  70

CCA AAT AAT GCA CGC CAG CTG GTA GAA ATT GCA GCC AGG GAT ATT GAG                295
Pro Asn Asn Ala Arg Gln Leu Val Glu Ile Ala Ala Arg Asp Ile Glu
             75                  80                  85

AAA CTT CTG AGC AAC AGA TCT AAA GCC CTG GTG AGC CTG GCA TTG GAA                343
Lys Leu Leu Ser Asn Arg Ser Lys Ala Leu Val Ser Leu Ala Leu Glu
         90                  95                  100

GCG GAG AAA GTT CAA GCA GCT CAC CAG TGG AGA GAA GAT TTT GCA AGC                391
Ala Glu Lys Val Gln Ala Ala His Gln Trp Arg Glu Asp Phe Ala Ser
    105                 110                 115

AAT GAA GTT GTC TAC TAC AAT GCA AAG GAT GAT CTC GAT CCT GAG AAA                439
Asn Glu Val Val Tyr Tyr Asn Ala Lys Asp Asp Leu Asp Pro Glu Lys
120                 125                 130                 135

AAT GAC AGT GAG CCA GGC AGC CAG AGG ATA AAA CCT GTT TTC ATT GAA                487
Asn Asp Ser Glu Pro Gly Ser Gln Arg Ile Lys Pro Val Phe Ile Glu
                140                 145                 150

GAT GCT AAT TTT GGA CGA CAA ATA TCT TAT CAG CAC GCA GCA GTC CAT                535
Asp Ala Asn Phe Gly Arg Gln Ile Ser Tyr Gln His Ala Ala Val His
             155                 160                 165

ATT CCT ACT GAC ATC TAT GAG GGC TCA ACA ATT GTG TTA AAT GAA CTC                583
Ile Pro Thr Asp Ile Tyr Glu Gly Ser Thr Ile Val Leu Asn Glu Leu
        170                 175                 180

AAC TGG ACA AGT GCC TTA GAT GAA GTT TTC AAA AAG AAT CGC GAG GAA                631
Asn Trp Thr Ser Ala Leu Asp Glu Val Phe Lys Lys Asn Arg Glu Glu
    185                 190                 195

GAC CCT TCA TTA TTG TGG CAG GTT TTT GGC AGT GCC ACT GGC CTA GCT                679
Asp Pro Ser Leu Leu Trp Gln Val Phe Gly Ser Ala Thr Gly Leu Ala
200                 205                 210                 215

CGA TAT TAT CCA GCT TCA CCA TGG GTT GAT AAT GGT AGA ACT CCA AAT                727
Arg Tyr Tyr Pro Ala Ser Pro Trp Val Asp Asn Gly Arg Thr Pro Asn
                220                 225                 230

ATG ATT GAC CTT TAT GAT GTA CGC AGA AGA CCA TGG TAC ATC CAA GGA                775
Met Ile Asp Leu Tyr Asp Val Arg Arg Arg Pro Trp Tyr Ile Gln Gly
             235                 240                 245

GCT GCA TCT CCT AAA GAC ATG CTT ATT CTG GTG GAT GTG AGT GGA AGT                823
Ala Ala Ser Pro Lys Asp Met Leu Ile Leu Val Asp Val Ser Gly Ser
        250                 255                 260

GTT AGT GGA TTG ACA CTT AAA CTG ATC CGA ACA TCT GTC TCC GAA ATG                871
Val Ser Gly Leu Thr Leu Lys Leu Ile Arg Thr Ser Val Ser Glu Met
    265                 270                 275

TTA GAA ACC CTC TCA GAT GAT GAT TTC GTG AAT GTA GCT TCA TTT AAC                919
Leu Glu Thr Leu Ser Asp Asp Asp Phe Val Asn Val Ala Ser Phe Asn
280                 285                                 295

AGC AAT GCT CAG GAT GTA AGC TGT TTT CAG CAC CTT GTC CAA GCA AAT                967
Ser Asn Ala Gln Asp Val Ser Cys Phe Gln His Leu Val Gln Ala Asn
                300                 305                 310

GTA AGA AAT AAA AAA GTG TTG AAA GAC GCG GTG AAT AAT ATC ACA GCC                1015
Val Arg Asn Lys Lys Val Leu Lys Asp Ala Val Asn Asn Ile Thr Ala
             315                 320                 325

AAA GGA ATT ACA GAT TAT AAG AAG GGC TTT AGT TTT GCT TTT GAA CAG                1063
```

| | | | | | | | | | | | | | | | |
|---|---|---|---|---|---|---|---|---|---|---|---|---|---|---|---|
| Lys | Gly | Ile | Thr | Asp | Tyr | Lys | Lys | Gly | Phe | Ser | Phe | Ala | Phe | Glu | Gln |
| | | 330 | | | | | 335 | | | | | 340 | | | |
| CTG | CTT | AAT | TAT | AAT | GTT | TCC | AGA | GCA | AAC | TGC | AAT | AAG | ATT | ATT | ATG | 1111 |
| Leu | Leu | Asn | Tyr | Asn | Val | Ser | Arg | Ala | Asn | Cys | Asn | Lys | Ile | Ile | Met |
| | 345 | | | | | 350 | | | | | 355 | | | | |
| CTA | TTC | ACG | GAT | GGA | GAA | GAG | AGA | GCC | CAG | GAG | ATA | TTT | AAC | AAA | TAC | 1159 |
| Leu | Phe | Thr | Asp | Gly | Glu | Glu | Arg | Ala | Gln | Glu | Ile | Phe | Asn | Lys | Tyr |
| 360 | | | | | 365 | | | | | 370 | | | | | 375 |
| AAT | AAA | GAT | AAA | AAA | CTA | CCT | GTA | TTC | ACC | TTC | TCA | GTT | GGT | CAA | CAC | 1207 |
| Asn | Lys | Asp | Lys | Lys | Leu | Pro | Val | Phe | Thr | Phe | Ser | Val | Gly | Gln | His |
| | | | | 380 | | | | | 385 | | | | | 390 | |
| AAT | TAT | GAC | AGA | GGA | CCT | ATT | CAG | TGG | ATG | GCC | TGT | GAA | AAC | AAA | GGT | 1255 |
| Asn | Tyr | Asp | Arg | Gly | Pro | Ile | Gln | Trp | Met | Ala | Cys | Glu | Asn | Lys | Gly |
| | | | 395 | | | | | 400 | | | | | 405 | | |
| TAT | TAT | TAT | GAA | ATT | CCT | TCC | ATT | GGT | GCA | ATA | AGA | ATC | AAT | ACT | CAG | 1303 |
| Tyr | Tyr | Tyr | Glu | Ile | Pro | Ser | Ile | Gly | Ala | Ile | Arg | Ile | Asn | Thr | Gln |
| | | 410 | | | | | 415 | | | | | 420 | | | |
| GAA | TAT | TTG | GAT | GTT | TTG | GGA | AGA | CCA | ATG | GTT | TTA | GCA | GGA | GAC | AAA | 1351 |
| Glu | Tyr | Leu | Asp | Val | Leu | Gly | Arg | Pro | Met | Val | Leu | Ala | Gly | Asp | Lys |
| | 425 | | | | | 430 | | | | | 435 | | | | |
| GCT | AAG | CAA | GTC | CAA | TGG | ACA | AAT | GTG | TAC | CTG | GAT | GCA | TTG | GAA | CTG | 1399 |
| Ala | Lys | Gln | Val | Gln | Trp | Thr | Asn | Val | Tyr | Leu | Asp | Ala | Leu | Glu | Leu |
| 440 | | | | | 445 | | | | | 450 | | | | | 455 |
| GGA | CTT | GTC | ATT | ACT | GGA | ACT | CTT | CCG | GTC | TTC | AAC | ATA | ACC | GGC | CAA | 1447 |
| Gly | Leu | Val | Ile | Thr | Gly | Thr | Leu | Pro | Val | Phe | Asn | Ile | Thr | Gly | Gln |
| | | | | 460 | | | | | 465 | | | | | 470 | |
| TTT | GAA | AAT | AAG | ACA | AAC | TTA | AAG | AAC | CAG | CTG | ATT | CTT | GGT | GTG | ATG | 1495 |
| Phe | Glu | Asn | Lys | Thr | Asn | Leu | Lys | Asn | Gln | Leu | Ile | Leu | Gly | Val | Met |
| | | | 475 | | | | | 480 | | | | | 485 | | |
| GGA | GTA | GAT | GTG | TCT | TTG | GAA | GAT | ATT | AAA | AGA | CTG | ACA | CCA | CGT | TTT | 1543 |
| Gly | Val | Asp | Val | Ser | Leu | Glu | Asp | Ile | Lys | Arg | Leu | Thr | Pro | Arg | Phe |
| | | 490 | | | | | 495 | | | | | 500 | | | |
| ACA | CTG | TGC | CCC | AAT | GG | | | | | | | | | | | 1560 |
| Thr | Leu | Cys | Pro | Asn | | | | | | | | | | | |
| | 505 | | | | | | | | | | | | | | |